(12) United States Patent
Bremner et al.

(10) Patent No.: US 7,160,854 B2
(45) Date of Patent: Jan. 9, 2007

(54) PEPTOID COMPOUNDS

(75) Inventors: John Bremner, Wollongong (AU); Stephen Pyne, Wollongong (AU); Paul Keller, Wollongong (AU); Dan Coghlan, Wollongong (AU); Adel Garas, Wollongong (AU); Helen Witchhard, Wollongong (AU); Tim Boyle, Wollongong (AU); Jonathan Coates, Richmond (AU)

(73) Assignee: University of Wollongong, Wollongong (AU)

( * ) Notice: Subject to any disclaimer, the term of this patent is extended or adjusted under 35 U.S.C. 154(b) by 0 days.

(21) Appl. No.: 10/481,663

(22) PCT Filed: Jun. 28, 2002

(86) PCT No.: PCT/AU02/00850

§ 371 (c)(1),
(2), (4) Date: Oct. 25, 2004

(87) PCT Pub. No.: WO03/002545

PCT Pub. Date: Jan. 9, 2003

(65) Prior Publication Data

US 2005/0043509 A1    Feb. 24, 2005

(30) Foreign Application Priority Data

Jun. 29, 2001    (AU) ..................... PR6044

(51) Int. Cl.
*A61K 38/02* (2006.01)
(52) U.S. Cl. .......................................................... 514/2
(58) Field of Classification Search ................... None
See application file for complete search history.

(56) References Cited

OTHER PUBLICATIONS

Chin et al. "Characterization of Solubilization of the FMRFamide Receptor of Squid," Biol. Bull. 187:185-199 (Oct. 1994).*
Sogah et al. "De novo design and synthesis of protein-based hybrid polymers," Polymer Preprints, 1993, 34(1), 108-9.*
Bremner, J., et al., "The Synthesis of a Novel Carbazole-linked Cyclic Peptoid with Antibacterial Activity," *Synlett*, No. 2:219-222, 2002.
Ezaki, M., et al., "Biphenomycin C, a Precursor of Biphenomycin A in Mixed Culture," *J. Antibiot* (Tokyo). 46(1):135-140, Jan. 1993.
Popieniek, P., et al., "A Fluorescent Ligand for Binding Studies with Glycopeptide Antibiotics of the Vancomycin Class," *Anal Biochem.* 165(1):108-13, Aug. 15, 1987.
Uchida, I., et al., "Biphenomycins A and B, Novel Peptide Antibiotics. II. Structural Elucidation of Biphenomycins A and B," *J. Antibiot* (Tokyo) 38(11):1462-8, Nov. 1985.

* cited by examiner

*Primary Examiner*—Cecilia J. Tsang
*Assistant Examiner*—Christina Bradley
(74) *Attorney, Agent, or Firm*—Seed IP Law Group PLLC

(57) ABSTRACT

The invention relates to new peptoid compounds of formula (I), as well as their use in the treatment of bacterial infections, such as those caused by vancomycin resistant microorganisms, and to compositions thereof.

20 Claims, No Drawings

PEPTOID COMPOUNDS

This invention relates to novel peptoid compounds, methods for preparing them and their use as antibiotics.

The death rate from infectious diseases in the developed world has increased over the last decade. This has been due to a number of factors, including increasing mobility of people from developed countries to less developed countries, increasing age of the general population, increasing numbers of transplant, cancer and AIDS patients who have lowered immunities to bacterial infections and the increasing numbers of bacterial species that have become multiply resistant to antibacterial drugs.[1-3]

The vancomycin group of antibiotics represent one of the last lines of defence against methicillin-resistant *Staphylococcus aureus* and other Gram-positive microorganisms.[4-6] These antibiotics interfere with cell-wall biosynthesis by binding to the D-Ala-D-Ala terminus of the disaccharyl pentapeptide of the peptidoglycan of the bacterial cell wall, resulting in cell death.[4-6] Recently vancomycin resistant bacteria have appeared. These bacteria have been identified as having a D-Ala-D-lactate terminus rather than a D-Ala-D-Ala terminus of the peptidoglycan. Vancomycin has a much lower affinity (ca. 1000 fold decrease in affinity) for the D-Ala-D-lactate terminus in vancomycin resistant bacteria and consequently it is much less effective as an antibiotic.[4-6]

The binding sites of vancomycin to the D-Ala-D-Ala terminus of bacterial cells have been well characterised. The D-O-E ring moiety of the vancomycin molecule is critical for binding to the D-Ala-D-Ala terminus of bacterial cells and the binding includes a number of hydrogen bonding interactions.[4-6] The more complex left-hand side of the vancomycin molecule has recently been shown to be critical for conformational control of the peptide moiety binding side.[7]

Biphenomycin A and B[8,9] have also been found to be potent antibiotics and are particularly active against Gram-positive bacteria Biphenomycin A has also been found to have low toxicity in mice.[8] The biphenomycins are structurally much simpler than vancomycin, The biphenomycins have a biphenyl group instead of a diphenyl ether as found in vancomycin, and have only one cyclic polypeptide ring and no sugar moieties. The biphenomycins also inhibit cell wall synthesis but, unlike vancomycin, not through binding to the D-Ala-D-Ala terminus of the disaccharyl pentapeptide of the peptidoglycan of the bacterial cell wall.[9]

There is a need for new compounds which are useful in the treatment of bacterial infections, especially those caused by vancomycin resistant microorganisms.

According to one aspect of the invention there is provided a compound of the formula (I):

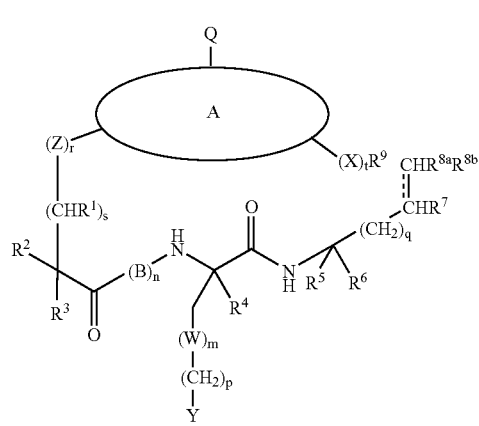

(I)

wherein
A is an aromatic or heteroaromatic ring system or partially or fully reduced derivatives thereof;
Q is hydrogen, $C_1-C_{12}$ straight chain, branched or cyclic alkyl substituted with one or more hydroxy groups, or a mono- or di-saccharide moiety;
Z is $-CR^{10}R^{11}-$, $-NR^{12}-$, $-C(O)O-$, $-C(O)NR^{12}-$ or $-O-$, where $R^{10}$ and $R^{11}$ are independently selected from hydrogen, hydroxy, $C_1-C_6$ alkyl, $C_6-C_{10}$ aryl, $C_1-C_6$ alkoxy and $-N(R^{13})_2$ and where each $R^{13}$ is independently selected from hydrogen and $C_1-C_6$ alkyl, and where $R^{12}$ is selected from hydrogen and $C_1-C_6$ alkyl;
$R^1$ is selected from hydrogen, hydroxy, $C_1-C_6$ alkyl, $C_1-C_6$ alkoxy, $-N(R^{13})_2$ and $-N(R^{12})-COR^{14}$; where $R^{12}$ and $R^{13}$ are as defined above, and where $R^{14}$ is selected from hydrogen, hydroxy, $C_1-C_6$ alkyl, $C_1-C_6$ alkoxy and $-NR^{12}$;
$R^2$ is independently selected from hydrogen, hydroxy, $C_1-C_6$ alkyl, $C_1-C_6$ alkoxy, $-N(R^{13})_2$ and $-N(R^{12})-COCHR^{2a}R^{2b}$; where $R^{2a}$ and $R^{2b}$ are independently selected from hydrogen, hydroxy, $C_1-C_6$ alkyl, $C_1-C_6$ alkoxy, $-N(R^{13})_2$ and $-N(R^{12})-COR^{14}$ where $R^{12}$, $R^{13}$ and $R^{14}$ are as defined above;
$R^3$, $R^4$ and $R^5$ are independently selected from hydrogen, $C_1-C_6$ alkyl and α side chains of α-amino acids or their enantiomers or their derivatives;
$R^6$ is $-CO_2R^{15}$, $-CONHR^{16}$, $-CONHOR^{16}$, $-CONHNHR^{16}$, $-SO_2N(R^{16})_2$, $-SO_2R^{17}$ or $-P(O)(OR^{18})(OR^{18})$ where each $R^{15}$, $R^{16}$, $R^{17}$ and $R^{18}$ is independently selected from hydrogen, $C_1-C_6$ alkyl, $C_3-C_7$ cycloalkyl, $C_6-C_{10}$ aryl and $C_7-C_{10}$ arylalkyl;
B is an α-amino acid residue, a β-amino acid residue or an α,α-disubstituted amino acid residue, such residue forming amide linkages with the adjacent molecules;
W is $-O-$ or $CR^{10}R^{11}$ where $R^{10}$ and $R^{11}$ are as defined above;
Y is an optionally substituted amino group, a moiety containing an optionally substituted amino group or a salt thereof;

----- is a single or double bond;
$R^7$ and $R^{8a}$ are hydrogen or are absent if

----- is a double bond; and
$R^{8b}$ and $R^9$ are hydrogen, and X is selected from $(CR^{10}R^{11})_u$, $-(CR^{10}R^{11})_u-CH=CH-$, $-NR^{12}(CR^{10}R^{11})_u-$, $-(CR^{10}R^{11})_u NR^{12}-$, $-O(CR^{10}R^{11})_u-$ or $-(CR^{10}R^{11})_u O-$, where $R^{10}$, $R^{11}$ and $R^{12}$ are as defined above; or
$R^{8b}$ and $R^9$ together form a covalent bond between X and the carbon to which $R^{8b}$ is attached, and X is selected from $(CR^{10}R^{11})_x$, $-NR^{12}(CR^{10}R^{11})_x-$, $-(CR^{10}R^{11})_x NR^{12}-$, $-O(CR^{10}R^{11})_x-$, $-O(CR^{10}R^{11})_x CH=CH-$ or $-(CR^{10}R^{11})_x O-$, where $R^{10}$, $R^{11}$ and $R^{12}$ are as defined above;
n, m, r and t are independently selected from 0 or 1;
s is an integer selected from 0 to 3;

p is an integer selected from 0 to 6, provided that when W is —O—, p is at least 1; and u, x and q are independently selected from 0 to 4;

and salts and pharmaceutically acceptable derivatives thereof.

The term "aromatic or heteroaromatic ring system" as used herein refers to a monoaryl, monoheteroaryl, or bridged, bonded or fused di- or poly-aryl or heteroaryl group and their atropisomers and to which X and Z may be attached at any ring position. Examples of fused di- or poly-aryl or heteroaryl groups include naphthene, fluorene, phenanthrene, indole, indazole, benzimidazole, carbazole, quinoline and isoquinoline, dibenzazepine and dibenzazocine.

Examples of bridged or bonded di- or poly-aryl or heteroaryl group include groups consisting of two or more aromatic carbocyclic or heterocyclic systems, such as benzene, naphthene, pyridine, pyrimidine, quinoline, isoquinoline, indole, indazole, and benzimidazole, or the like, joined by a covalent bond, and/or bridging group or groups, of one or more atoms such as —O—, —CH$_2$—, —NH—, —SO$_2$—. Examples of bonded di- or poly-aryl or heteroaryl systems include biphenyl, binaphthyl, biquinolyl, bi-isoquinolyl, bi-indole, bi-benzimidazole, phenyl-isoquinolyl, phenyl-quinolyl, phenyl-naphthyl, phenyl-indole, phenyl-benzimidazole, phenyl-indazole, phenyl-pyridine, phenyl-pyrimidine, naphthyl-pyridine, naphthyl-pyrimidine, naphthyl-isoquinolyl, naphthyl-quinolyl, naphthyl-indole, naphthyl-benzimidazole, naphthyl-indazole, quinolyl-isoquinolyl, quinolyl-indole, quinolyl-indazole, quinolyl-benzimidazole, indole-indazole, indole-benzimidazole, indazole-benzimidazole and the like, and their atropisomers. The two aryl or heteroaryl groups may be linked at any position.

The aromatic or heteroaromatic groups or partially or fully reduced derivatives thereof may optionally be substituted with one or more $C_1$–$C_6$ alkyl, $C_1$–$C_6$ thioalkoxy, hydroxy, $C_1$–$C_6$ alkoxy, amino, $C_1$–$C_6$ alkylamino, $C_1$–$C_6$ dialkylamino, halo, nitro, nitrile, sulphonylsulphonamide or alkyl- or aryl-sulphonyl, $C_1$–$C_6$ haloalkyl (for example trifluoromethyl) or carboxy groups. Preferably, the aromatic or heteroaromatic groups or partially or fully reduced derivatives are unsubstituted or have from one to four substituents selected from methyl, hydroxy, methoxy, amino, halo, or trifluoromethyl. Any nitrogen atoms in the heteroaromatic groups may be protected by protecting groups such as t-butoxycarbonyl (BOC), 2,2,5,7,8-pentamethylchroman-6-sulfonyl (Pmc), benzyl, acetyl, carbobenzyloxy and the like (see "Protective Groups in Organic Synthesis" Theodora Greene and Peter Wuts, third edition, Wiley Interscience, 1999).

Preferred aromatic and heteroaromatic ring systems include 1,1'-binaphthyl, especially where the binaphthyl is substituted at the 2 and 2' positions with substituents selected from $C_1$–$C_3$ alkyl, $C_1$–$C_3$ alkoxy, or arylalkyl, indole, phenyl, and N-protected or unprotected carbazole. Particularly preferred aromatic ring systems are 3,3'-linked 1,1'-binaphthyl, where substitution of X and Z are at the 3 and 3'-positions respectively ("3,3'-linked binaphthyl compounds") particularly those which are 2,2'-$C_1$–$C_3$ alkoxy substituted, 2,2'-linked 1,1'-binaphthyl where substitution of X and Z are at the 2 and 2' positions ("2,2'-linked binaphthyl compounds"), 3,6-linked 9H-carbazole ("3,6-linked 9H-carbazole compounds"), 1,3-linked indole ("1,3-linked indole compounds") and 1,4-linked phenyl ("1,4-linked phenyl compounds")systems.

As used herein the term "atropisomer" refers to an enantiomer of a compound that exhibits conformational axial chirality.

As used herein the term "monosaccharide moiety" refers to a simple sugar substituent derived from a monosaccharide or a derivative thereof. The monosaccharide may be a naturally occurring monosaccharide moiety, or may be a substituted, protected or otherwise derivatised analogue of a naturally occurring monosaccharide. The monosaccharide may be mono, di- or triphosphated, and may be in its fully oxygenated form, or a deoxy form. Examples of monosaccharides from which the monosaccharide moiety may be derived include, but are not limited to abequose, iduronic acid, allose, lyxose, altrose, mannose, apiose, muramic acid, arabinose, neuraminic acid, arabinitol, N-acetylneuraminic acid, 2-deoxyribose, N-acetyl-2-deoxyneur-2-enaminic acid, fructose, N-glycoloylneuraminic acid, fucose, 3-deoxy-D-manno-oct-2-ulosonic acid, fucitol, rhamnose, galactose, 3,4-di-O-methylrhamnose, galactosamine, psicose, N-acetylgalactosamine, quinovose, β-D-galactopyranose 4-sulfate, ribose, glucose, ribose 5-phosphate, glucosamine, ribulose, 2,3-diamino-2,3-dideoxy-D-glucose, sorbose, glucitol, tagatose, N-acetylglucosamine, talose, glucuronic acid, xylose, ethyl glucopyranuronate, xylulose, gulose, 2-C-methylxylose, and idose.

As used herein the term "disaccharide moiety" refers to a sugar substitient composed of two glycosidically linked monosaccharides, or derivatives thereof. Examples of suitable disaccharide moieties include, but are not limited to, sucrose, lactose and maltose.

As used herein the term "optionally substituted amino group" refers to an unsubstituted amino group (NH$_2$) or an amino group substituted on the nitrogen atom with up to two substituents and salts thereof. The term "moiety containing an optionally substituted amino group" refers to groups that contain an amino group (NH$_2$) or an amino group substituted on the nitrogen atom with up to two substituents. Examples of optional substituents include $C_1$–$C_6$ alkyl, $C_3$–$C_7$ cycloalkyl, $C_6$–$C_{10}$ aryl and suitable nitrogen protecting groups (see "Protective Groups in Organic Synthesis" Theodora Greene and Peter Wuts, third edition, Wiley Interscience, 1999). Preferably, the amino group is capable of carrying a positive charge at biological pH. In a preferred form of the invention, Y is selected from a group consisting of: —N(R$^{13}$)$_2$, —N(R$^{12}$)—COR$^{14}$, —NR$^{13}$C(=NR$^{13}$)N(R$^{13}$)$_2$, —C(=NR$^{13}$)N(R$^{13}$)$_2$, —NR$^{13}$C(=O)N(R$^{13}$)$_2$, —N=NC(=NR$^{13}$)N(R$^{13}$)$_2$, NR$^{13}$NR$^{13}$C(=O)NHN(R$^{13}$)$_2$, —NR$^{13}$C(=)NHN(R$^{13}$)$_2$, wherein R$^{12}$ and each R$^{13}$ is independently selected from hydrogen and $C_1$–$C_6$ alkyl and R$^{14}$ is selected from hydrogen, hydroxy, $C_1$–$C_6$ alkyl, $C_1$–$C_6$ alkoxy and NR$_{12}$; and 3–8-membered N-containing cyclogroup such as piperidinyl, pyrrolidinyl, imidazolidinyl, pyrazolidinyl or piperazinyl, wherein the 3–8-membered N-containing cyclogroup can be attached via a nitrogen or carbon atom. Preferred Y groups include optionally substituted guanidino [—NHC(=NH)NH$_2$], amidino [—C(=NH)NH$_2$], ureido [—NHC(=O)NH$_2$], carbazono [—N=NC(=)NHNH$_2$], carbazido [—NHNHC(=O)NHNH$_2$] and semicarbazido [—NHC(=O)NHNH$_2$] and amino (NH$_2$).

As used herein the term "$C_1$–$C_6$ alkyl" refers to straight chain or branched alkyl groups having from 1 to 6 carbon atoms. Examples of such groups include methyl, ethyl, n-propyl, isopropyl and n-butyl.

As used herein the term "$C_3$–$C_7$ cycloalkyl" refers to cyclic alkyl groups having from 3 to 7 carbon atoms. Examples of such groups include cyclopropyl, cyclobutyl, cyclopentyl or cyclohexyl.

As used herein the term "$C_6$–$C_{10}$ aryl" refers to carbocyclic aromatic systems having from 6 to 10 carbon atoms. Examples of such groups include phenyl and naphthyl.

As used herein the term "$C_7$–$C_{10}$ arylalkyl" refers to carbocyclic aromatic systems having 6 carbon atoms bonded to a $C_1$–$C_4$ alkyl group. An example of an arylalkyl group is a benzyl group.

As used herein the term "$C_1$–$C_6$ alkoxy" refers to straight chain or branched alkoxy groups having from 1 to 6 carbon atoms. Examples of such groups include methoxy, ethoxy, n-propoxy, isopropoxy and different butoxy isomers.

The term α side chain of an α-amino acid includes the α-R group of a naturally occurring α-amino acid and may be selected from —$CH_3$, —$(CH_2)_3NHC(=NH)NH_2$, —$CH_2CONH_2$, —$CH_2CO_2H$, —$CH_2SH$, —$(CH_2)_2CONH_2$, —$(CH_2)_2CO_2H$, —$CH_2$(4-imidazole), —$CH(CH_3)CH_2CH_3$, —$CH_2CH(CH_3)_2$, —$(CH_2)_3NH_2$, —$(CH_2)_4NH_2$, —$(CH_2)_2SCH_3$, —$CH_2Ph$, —$CH_2OH$, —$CH(CH_3)OH$, —$CH_2$(3-indolyl), —$CH_2$(4-hydroxyphenyl) and —$CH(CH_3)_2$. This term also includes the includes α-R groups of non-naturally occurring α-amino acid such as those found in homoarginine, homoserine, homocysteine, norvaline, norleucine or amidino derivatives. For example such α-side chains include —$(CH_2)_4NHC(=NH)NH_2$, —$(CH_2)_2OH$, —$(CH_2)_2SH$, —$CH_2CH_2CH_3$, —$(CH_2)_3CH_3$, or $(CH_2)_vC(=NH)NH_2$ where v is an integer from 1 to 4. Other derivatives may include α-side chains in which hydroxy, thiol or amino groups are protected with suitable hydroxy, thiol or amino protecting groups (see "Protective Groups in Organic Synthesis" Theodora Greene and Peter Wuts, third edition, Wiley Interscience, 1999).

B is an α-amino acid residue, a β-amino acid residue or an α,α-disubstituted amino acid residue. Suitable α-amino acids include those derived from naturally occurring α-amino acids and non-naturally occurring α-amino acids. Examples of suitable α-amino acids include D- and L-α-amino acid residues derived from alanine, arginine, homoarginine, asparagine, aspartic acid, cysteine, homocysteine, glutamine, glutamic acid, glycine, histidine, isoleucine, leucine, norleucine, lysine, methionine, phenylalanine, serine, homoserine, threonine, tryptophan, tyrosine, proline, valine and norvaline. Other suitable α-amino acid residues may have a side chain containing an amidino group, for example, $(CH_2)_vC(=NH)NH_2$ where v is an integer from 1 to 4. D- or L-alanyl, D-lysinyl, D-arginyl and D-homoarginyl residues are particularly preferred. Suitable β-amino acids include $H_2NC(R^1)R^2C(R^3)R^4CO_2H$ where $R^1$, $R^2$, $R^3$, $R^4$ can be H and any of the substituents described above for the α-amino acids, and all possible stereoisomers. Suitable α,α-disubstituted amino acids include any of the above α-amino acids having a further substituent in the α-position. Suitable substituents include $C_1$–$C_6$ alkyl, hydroxy, $C_1$–$C_6$ alkoxy, amino, $C_1$–$C_6$ alkyl amino, $C_1$–$C_6$ dialkylamino, $(CH_2)_vNH_2$, $(CH_2)_vNHC_1$–$C_6$ alkyl, $(CH_2)_vN(C_1$–$C_6$alkyl$)_2$, $(CH_2)_vNHC(=NH)NH_2$, $(CH_2)_vOH$, $(CH_2)_vOC_1$–$C_6$alkyl.

Preferred compounds of the present invention include:
benzyl (aR/S,2S,5R)-8-acetamido-2-allyl-9-{3-[3'-allyl-2,2'-dimethoxy-1,1'-binaphthyl]}-3,6-diaza-5-(4-{[(tert-butoxy)carbonyl]amino}butyl)-4,7-dioxononanoate
(aR/S,7R,10S)-4-acetamido-7-(4-aminobutyl)-6,9-diaza-10-methoxycarbonyl-1(1,3),2(1,3)-di(2-methoxynaphthalena)-5,8-dioxocyclotetradecaphane-12-ene hydrochloride.
(aR/S,7R,10S)-4-acetamido-7-(4-aminobutyl)-6,9-diaza-10-methoxycarbonyl-1(1,3),2(1,3)-di(2-methoxynaphthalena)-5,8-dioxocyclotetradecaphane hydrochloride
(aR/S,7R,10S)-4-acetamido-6,9-diaza-10-benzyloxycarbonyl-7-(4-{[(tert-butoxy)carbonyl]amino}butyl)-1(1,3),2(1,3)-di(2-methoxynaphthalena)-5,8-dioxocyclotetradecaphane-12-ene
methyl (aR/S,2S,5R)-8-acetamido-2-allyl-9-[3-(3'-allyl-2,2'-dimethoxy-1,1'-binaphthyl)]-3,6-diaza-5-(3-guanidinopropyl)-4,7-dioxononanoate hydrochloride
(aR/S,7S,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane-12-ene hydrochloride
(aR/S,7R,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane-12-ene hydrochloride
(aR/S,7R,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane hydrochloride
Methyl (2S,5S,8R/S)-8-acetamido-2-allyl-9-[6-allyl-9-tert-butoxycarbonyl-9H-carbazol-3-yl]-3,6-diaza-5-{3-[(2,2,5,7,8-pentamethylchroman-6-sulfonyl)-guanidino]propyl}-4,7-dioxononanoate
6-Acetamido-8,11-diaza-9-(3-guanidinopropyl)-12-methoxycarbonyl-7,10-dioxo-[12](3,6)-1H-carbazolophane HCl (9S,12S)
6-Acetamido-8,11-diaza-14-ene-9-(3-guanidinopropyl)-12-methoxycarbonyl-7,10-dioxo-[12](3,6)-1H-carbazolophane HCl (9R,12S)
6-Acetamido-8,11-diaza-9-(3-guanidinopropyl)-12-methoxycarbonyl-7,10-dioxo-[12](3,6)-1H-carbazolophane HCl (9R,12S)
6-Acetamido-9-(4-aminobutyl)-8,11-diaza-1-tert-butoxycarbonyl-14-ene-12-methoxycarbonyl-7,10-dioxo-[12](3,6)-1H-carbazolophane HCl (9S,12S)
6-Acetamido-9-(4-aminobutyl)-8,11-diaza-12-methoxycarbonyl-7,10-dioxo-[12](3,6)-1H-carbazolophane HCl (9S,12S)
Methyl (2S,5S,8R/S)-8-Acetamido-5-(4-aminobutyl)-3,6-diaza-9-{9-[(4-methoxyphenyl)methyl]-6-propyl-9H-carbazol-3-yl}-4,7-dioxo-2-propylnonanoate hydrochloride
6-Acetamido-9-(4-aminobutyl)-8,11-diaza-12-methoxycarbonyl-7,10-dioxo-[12](3,6)-1H-carbazolophane HCl (9R,12S)
methyl (aR/S,2S,5R)-2-allyl-5-[2-({[(2'-allyloxy-1,1'-binaphthoxymethyl]carbonyl}amino)-3-aza-9-guanidino-4-oxononanoate hydrochloride
(aR,S,7R,10S)-6,9-diaza-3,15-dioxa-5,8-dioxo-7-(4-guanidinobutyl)-10-methoxycarbonyl-1(1,2),2(1,2)-dinaphthalenacyclopentadecaphane-12-ene hydrochloride
methyl (aS/R,2S,5R)-2-allyl-10-(2'-allyloxy-1,1'-binaphth-2-oxy)-5-(4-aminobutyl)-3,6-diaza-4,7-dioxodecanoate hydrochloride
methyl (aS/R,2S,5R)-2-allyl-10-(2'-allyloxy-1,1'-binaphth-2-oxy)-3,6-diaza-5-(4-guanidinobutyl)-4,7-dioxodecanoate hydrochloride
(aR/S,9R,12S)-8,1-diaza-9-(4-guanidinobutyl)-12-methoxycarbonyl-1(1,2),2(1,2)-dinaphthalena-3,17-dioxa-7,10-dioxoheptadecaphane-15-ene hydrochloride It will be appreciated that the compounds of the present invention have more than one asymmetric centre, and therefore are capable of existing in more than one stereoisomeric form. Some of the compounds may also exist as geometric isomers. Furthermore, some compounds of the invention may also have conformational axial chirality resulting in atropisomers. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates, reagents or catalysts.

The salts of the compound of formula (I) are preferably pharmaceutically acceptable, but it will be appreciated that non-pharmaceutically acceptable salts also fall within the scope of the present invention, since these are useful as intermediates in the preparation of pharmaceutically acceptable salts. The pharmaceutically acceptable salts may include conventional non-toxic salts or quaternary ammonium salts of these compounds, which may be formed, e.g. from organic or inorganic acids or bases. Examples of such acid addition salts include, but are not limited to, those formed with pharmaceutically acceptable acids such as acetic, propionic, citric, lactic, methanesulphonic, toluenesulphonic, benzenesulphonic, salicyclic, ascorbic, hydrochloric, orthophosphoric, sulphuric and hydrobromic acids. Base salts includes, but is not limited to, those formed with pharmaceutically acceptable cations, such as sodium, potassium, lithium, calcium magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

Pharmaceutically acceptable derivatives may include any pharmaceutically acceptable salt, hydrate, prodrug, or any other compound which, upon administration to a subject, is capable of providing (directly or indirectly) a compound of formula (I) or an antibacterially active metabolite or residue thereof. For example, compounds where a hydroxy group on the Q moiety has been replaced with a phosphate ester are within the scope of pharmaceutically acceptable derivatives.

The term "prodrug" is used in its broadest sense and encompasses those derivatives that are converted in vivo to the compounds of the invention. Such derivatives would readily occur to those skilled in the art, and include N-α-acyloxy amides, N-(acyloxyalkoxy carbonyl) amine derivatives and α-acyloxyalkyl esters of phenols and alcohols. A prodrug may include modifications to one or more of the functional groups of a compound of the invention.

Throughout this specification the phrase "a group which is capable of being converted in vivo" used in relation to another functional group includes all those functional groups or derivatives of such groups which upon administration into a mammal may be converted into the stated functional group. Those skilled in the art may readily determine whether a group may be capable of being converted in vivo into the stated functional group using routine enzymatic or animal studies.

Preferred compounds of the invention have the formula (IA):

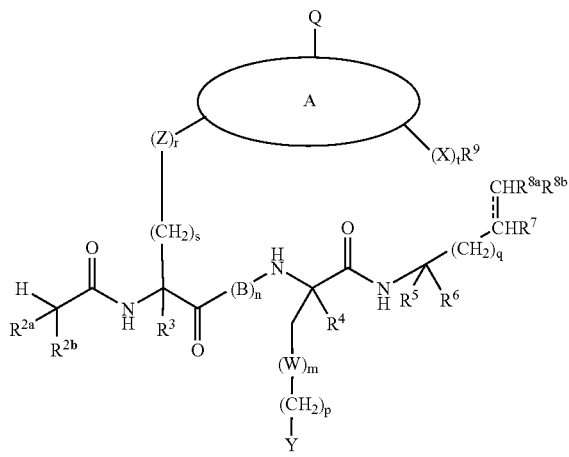

(IA)

wherein A, Q, Z, $R^{2a}$, $R^{2b}$, $R^3$, B, W, Y, $R^4$, $R^5$, $R^6$, $R^7$, $R^{8a}$, $R^{8b}$, $R^9$, X, r, s, n, m, p q and t are as defined above.

Preferably one or more of the following definitions apply to preferred compounds:

Q is hydrogen;
A is 2,2'-linked 1,1'-binaphthyl, 3,3'-linked 2,2'-dimethoxy-1,1'-binaphthyl, phenyl preferably 1,4-linked, indolyl preferably 1,3-linked, fluorenyl or 9H-carbazole preferably 3,6-linked;

Z is —O— or —$CR^{10}R^{11}$—, more preferably —O— or —$CH_2$—;
$R^1$ is hydrogen or hydroxy;
$R_2$ is hydrogen, hydroxy or NHC(=O)$CHR^{2a}R^{2b}$, preferably hydrogen or NHC(=O)$CH_3$;
$R_3$ is hydrogen;
B is absent or a D- or L-alanyl residue, a D- or L-lysinyl, a D- or L-arginyl residue or a D- or L-homoarginyl residue;
W is absent or is $CH_2$;
Y is $NH_2$, NHC(=NH)$NH_2$ or salts thereof;
$R_4$ is hydrogen;
$R_5$ is hydrogen;
$R_6$ is —$CO_2R^{15}$, where $R^{15}$ is $C_1$–$C_6$ alkyl or $C_7$–$C_{10}$ arylalkyl, most preferably $R^{15}$ is methyl or benzyl;
$R^{8b}$ and $R^9$ are hydrogen and X is —$(CR^{10}R^{11})_u$—, —CH=CH— —$O(CR^{10}R^{11})$CH=CH—, or —$CR^{10}R^{11}$—CH=CH— where $R^{10}$ and $R^{11}$ are hydrogen and u is an integer selected from 2 or 3;
$R^{8b}$ and $R^9$ together form a covalent bond between X and the carbon to which $R^{8b}$ is attached and X is —$CR^{10}R^{11}$—, where $R^{10}$ and $R^{11}$ are hydrogen.

Particularly preferred compounds in which A is a carbazole moiety are:
6-acetamido-8,11-diaza-9-(3-guanidinopropyl)-12-methoxycarbonyl-7,10-dioxo-[12](3,6)-1H-carbazolophane HCl (9R,12S),
methyl 8-acetamido-3,6-diaza-5-[3-guanidinopropyl]-4,7-dioxo-2-propyl-9-[3-(6-propyl)-9H-carbazole]nonanoate HCl (2S,5R),
6-acetamido-8,11-diaza-14-ene-9-(3-guanidinopropyl)-12-methoxycarbonyl-7,10-dioxo-[12](3,6)-1H-carbazolophane HCl (9R,12S),
methyl 8-acetamido-5-[4-aminobutyl]-3,6-diaza-4,7-dioxo-2-propyl-9-[3-(6-propyl)-9H-carbazole]nonanoate HCl (2S,5R),
6-acetamido-9-(4-aminobutyl)-8,11-diaza-12-methoxycarbonyl-7,10-dioxo-[12](3,6)-1H-carbazolophane HCl (9S, 12S),
6-acetamido-8,11-diaza-9-(3-guanidinopropyl)-12-methoxycarbonyl-7,10-dioxo-[12](3,6)-1H-carbazolophane HCl (9S,12S),
6-acetamido-9-(4-aminobutyl)-8,11-diaza-14-ene-12-methoxycarbonyl-7,10-dioxo-[12](4,17)-1H-carbazolophane HCl (9R,12S),
6-acetamido-9-(4-aminobutyl)-8,11-diaza-12-methoxycarbonyl-7,10-dioxo-[12](3,6)-1H-carbazolophane HCl (9R, 12S),
6-acetamido-9-(4-aminobutyl)-8,11-diaza-1-tert-butoxycarbonyl-14-ene-12-methoxycarbonyl-7,10-dioxo-[12](3,6)-1H-carbazolophane HCl (9S,12S),
6-acetamido-9-(4-aminobutyl)-8,11-diaza-1-tert-butoxycarbonyl-1 2-methoxycarbonyl-7,10-dioxo-[12](3,6)-1H-carbazolophane HCl (9S,12S),
6-acetamido-9-(4-aminobutyl)-8,11-diaza-12-methoxycarbonyl-1-(4-methoxyphenylmethylene)-7,10-dioxo-[12](3,6)-1H-carbazolophane HCl (9S,12S),
6-acetamido-9-(4-aminobutyl)-8,11-diaza-4-ene-12-methoxycarbonyl-1-(4-methoxyphenylmethylene)-7,10-dioxo-[12](3,6)-1H-carbazolophane HCl (9S,12S),
6-acetamido-9-(4-aminobutyl)-8,11-diaza-14-ene-12-methoxycarbonyl-7,10-dioxo-[12](3,6)-1H-carbazolophane HCl (9S,12S),
6-acetamido-8,11-diaza-14-ene-9-(3-guanidinopropyl)-12-methoxycarbonyl-7,10-dioxo-[12](3,6)-1H-carbazolophane HCl (9S,12S), methyl 8-acetamido-5-[4-aminobutyl]-3,6-diaza-9-[3-(9-methoxyphenylmethylene)-6-propyl-9H-carbazole]-4,7-dioxo-2-propylnonanoate HCl (2S,5S)

Particularly preferred compounds in which A is a 2,2′-disubstituted binaphthyl moiety are the compounds prepared in Examples 15 and 21.

Compounds of formula (I) as described above, may be prepared by reacting a compound of formula (II)

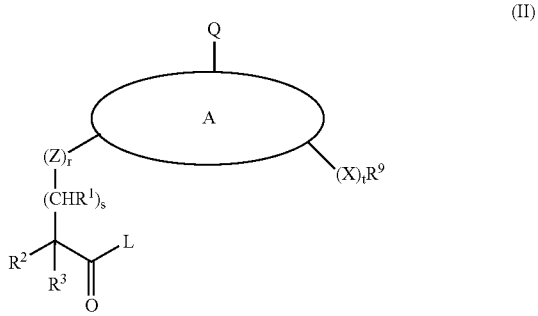

wherein L is OH or an activating group; with a compound of formula (III)

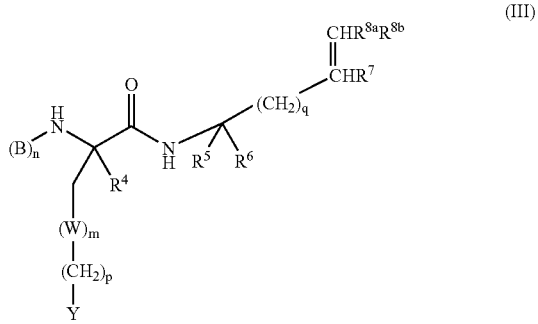

wherein B is either H or an amino acid having a free amino group; under appropriate conditions. Unless otherwise defined, A, Q, X, Z, B, W, Y, $R^1$, $R^2$, $R^3$, $R^4$, $R^5$, $R^6$, $R^7$, $R^{8a}$, $R^{8b}$, $R^9$, n, m, p, q, r, s and t in formulae (II) and (III) are as defined in formula (I).

The compound of formula (I) prepared by the coupling of compounds of formulae (II) and (III) may be further transformed using conventional approaches to provide other compounds of formula (I).

Conveniently, the reaction between compounds of formulae (II) and (III) is based on forming an amide bond and may be conducted using approaches routinely used in peptide synthesis. For example, the coupling reaction of an amine with a carboxylic acid (L=OH) or an activated carbonyl carbon such as an acyl chloride, acyl azide or an anhydride (L=Cl, $N_3$, OC(O)R).

Compounds of formula (II) may be conveniently prepared from an aromatic or heteroaromatic ring system carrying any of:

(a) desired substituents; or
(b) functional groups which may be converted into desired substituents using conventional approaches known to those skilled in the art; or
(c) appropriately activated positions on the nucleus of the ring system such that desired substituents may be placed on the ring system using conventional approaches known to those skilled in the art.

In addition the ring system includes a position that may be converted into the group $—(X)_tR^9$, and a position where the side chain to be reacted with (III) may be formed. These positions may be functional groups or may be appropriately activated positions on the ring system such as to allow conversion into functional groups using conventional approaches known to those skilled in the art. For example, functional groups include halogen, hydroxyl, amino, alkoxycarbonyl, and alkenyl. Examples of suitably activated positions include those which may be halogenated, hydroxylated, oxidised to a carbonyl group, alkylated or acylated.

Suitable aromatic or heteroaromatic ring systems may be commercially available or be readily prepared from commercially available ring systems or ring system precursors.

The side chain to be reacted with a compound of formula (III) may be formed using any suitable approach readily ascertainable to those skilled in the art. Conveniently, a haloalkyl group on the ring system may be alkylated to form the side chain, in some cases after further modification. The side chain includes appropriate functionality to allow for the reaction between compounds of formulae (II) and (III). Preferably, this is based on forming an amide bond and may be conducted using approaches routinely used in peptide synthesis, for example, the reaction of an amine with an appropriately activated carbonyl carbon. Those skilled in the art can readily determine appropriate methodology to build the desired side chain.

Where appropriate, protecting groups may be used to mask certain positions on the compound of formula (II) so as to avoid or limit unwanted side reactions.

Compounds of formula (III) may be prepared using approaches familiar to those skilled in the art of peptide chemistry or simple modifications of those approaches. Those skilled in the art can readily determine appropriate methodology to build the desired compound of formula (III).

Where appropriate protecting groups may be used to mask certain positions on the compound of formula (III) so as to avoid or limit unwanted side reactions.

Preferably, the compound of formula (III) includes a free amino group and the compound of formula (II) includes a free carboxylic acid or an activated carbonyl carbon that may be reacted under appropriate conditions to form an amide bond.

Compounds of formula (I) where $R^{8b}$ and $R^9$ together form a covalent bond between X and the carbon to which $R^{8b}$ is attached are conveniently formed by cyclisation of the corresponding non-cyclised compound. Cyclisation may be achieved using any ring closing reaction known to those skilled in the art. For example, where the bond between $CHR^7$ and $CHR^{8a}R^{8b}$ is a double bond, and $—(X)_tR^9$ includes an alkenyl bond then ring closure may conveniently be performed using a ring closing metathesis reaction. The resulting cyclised alkene may be readily reduced to an alkyl bond using conventional approaches.

Examples of these general approaches are described in more detail in the experimental section.

The compounds of the present invention may be useful in the treatment of bacterial infections in mammals, particularly humans. They are particularly useful for treating infections caused by Gram positive bacteria In particular, the compounds of the invention are useful for treating infections caused by Gram positive bacteria such as *Enterococcus faecium, Staphylococcus aureus, Staphylococcus epidermis, Klebsiella pneumoniae, Streptococcus pneumoniae*, including multiresistant strains such as vancomycin resistant *Staphylococcus aureus* and methicillin-resistant *Staphylococcus aureus*.

Accordingly in a further aspect the invention provides a method for the treatment of bacterial infection in a mammal comprising the step of administering an effective amount of a compound (I).

The invention also provides the use of a compound of formula (I) in the manufacture of a medicament for the treatment or prophylaxis of bacterial infections.

The compounds of the invention are administered to the mammal in a treatment effective amount. As used herein, a treatment effective amount is intended to include at least partially attaining the desired effect, or delaying the onset of, or inhibiting the progression of, or halting or reversing altogether the onset or progression of the bacterial infection.

As used herein, the term "treatment effective amount" relates to an amount of compound which, when administered according to a desired dosing regimen, provides the desired therapeutic activity. Dosing may occur at intervals of minutes, hours, days, weeks, months or years, or continuously over any one of these periods. Suitable dosages lie within the range of about 0.1 ng per kg of body weight to 1 g per kg of body weight per dosage. The dosage is preferably in the range of 1 ng to 1 g per kg of body weight per dosage, such as is in the range of 1 mg to 1 g per kg of body weight per dosage. Suitably, the dosage is in the range of 1 mg to 500 mg per kg of body weight per dosage, such as 1 mg to 200 mg per kg of body weight per dosage, or 1 mg to 100 mg per kg of body weight per dosage. Other suitable dosages may be in the range of 1 mg to 250 mg per kg of body weight, including 1 mg to 10, 20, 50 or 100 mg per kg of body weight per dosage or 10 mg to 100 mg per kg of body weight per dosage. The compounds of the invention may be administered in a single dose or a series of doses.

Suitable dosage amounts and dosing regimens can be determined by the attending physician and may depend on the particular condition being treated, the severity of the condition, as well as the general health, age and weight of the subject being treated.

While it is possible that, for use in therapy, a compound of the invention may be administered as the neat chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers thereof and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Liquids or powders for intranasal administration, tablets or capsules for oral administration and liquids for intravenous administration are preferred compositions.

The invention will now be described with reference to the following examples which illustrate some preferred aspects of the present invention. However, it is to be understood that the particularity of the following description of the invention is not to supersede the generality of the preceding description of the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

General Experimental Information

Melting point (mp) determinations were carried out on a Gallenkamp or Reichert melting point apparatus. Chemical ionisation (CI) and electron impact (EI) mass spectra were obtained on a Shimadzu QP-5000 mass spectrometer by a direct insertion technique with an electron beam energy of 70 eV. Electrospray (ES) mass spectra were obtained on a VG Quattro spectrometer. High-resolution mass spectra (HRMS) were determined on a VG Autospec spectrometer or on a micromass QT°F spectrometer. The m/z values are stated with their peak intensity as a percentage in parentheses. Proton and carbon nuclear magnetic resonance (NMR) spectra were determined with a Varian Unity 300 MHz spectrometer or with a Varian Unity 400 MHz spectrometer where specified. Spectra were recorded in (D)chloroform ($CDCl_3$) using chloroform or TMS as the internal standard, unless specified otherwise. Chemical shifts (δ) in ppm were measured relative to the internal standard. Where samples exhibited several isomers, the chemical shifts for the major form are given since the major and minor isomers could not be separated, and overlapping peaks made it difficult to specify all the chemical shifts for the minor isomer(s). Analytical thin layer chromatography (TLC) was carried out on Merck Kieselgel 60 $F_{254}$ precoated aluminium plates with a thickness of 0.25 mm. All column chromatography was performed under flash conditions on Merck Kieselgel 60 (230–400 mesh). Chromatography solvent mixtures were measured by volume. Organic solvent extracts were dried with anhydrous magnesium sulfate, and the solvent removed under reduced pressure with a Büchi rotary evaporator. Solvents were purified and dried by standard techniques. All compounds were judged to be of greater than 90% purity based upon $^1$H NMR and TLC analysis. Starting materials and reagents were purchased from Sigma-Aldrich Pty Ltd and were used as received. Petroleum spirit refers to the 40–60° C. bp range material. The Grubbs' ruthenium catalyst used was specifically benzylidene-bis(tricyclohexylphosphine)-dichlororuthenium.

| | Abbreviations |
|---|---|
| Ac | acetyl |
| Boc | tert-butyloxycarbonyl |
| DCM | dichloromethane |
| DMF | N,N-dimethylformamide |
| DMSO | dimethyl sulfoxide |
| HCl | hydrochloric acid |
| EtOAc | ethyl acetate |
| MeOH | methanol |
| Pmc | 2,2,5,7,8-pentamethylchroman-6-sulfonyl |
| PS | petroleum spirit |
| TFA | trifluoracetic acid |
| THF | tetrahydrofuran |
| DMAP | 4-dimethylaminopyridine |
| DCC | 1,3-dicyclohexylcarbodiimide |
| HMPA | hexamethylphosphoramide |
| TMEDA | N,N,N',N'-tetramethylethylenediamine |
| Fmoc | 9-fluorenylmethoxycarbonyl |

Example Synthesis of Peptides

Example 1

Protection of the Carboxylic Acid of L-Allylglycine

L-Allylglycine (0.600 g) was dissolved in dry methanol (7 mL) and cooled in an ice bath. Thionyl chloride (2 equivalents) was added dropwise and the reaction warmed to room temperature and left to stir for 3 hours at room temperature after which the solvent was removed by rotary evaporation. The residue was redissolved in methanol and re-evaporated several times to give a 90% yield of a white low melting point solid.

MS ES 130 [$RNH^3$]$^+$. $^1$H NMR 400 MHz ($CDCl_3$) δ8.58, 3H, br s, $NH_3$; 5.8, 1H, br s, H2, 5.32, 1H,d, J=15.6 Hz, H1; 5.26, 1H, d, J=6.8 Hz, H1'; 4.20, 1H, m, H4; 3.80, 3H, s, $OCH_3$; 2.88, 2H, m, H3,H3'. $^{13}$C NMR 75 MHz δ169.2, $CO_2CH_3$; 130.1, C2; 121.5, C1; 53.3, $OCH_3$; 53.0, C4; 34.5, C3.

Example 2

Preparation of Nα-Fmoc-Nε-Boc-D-Lysine-L-Allylglycine Methyl Ester

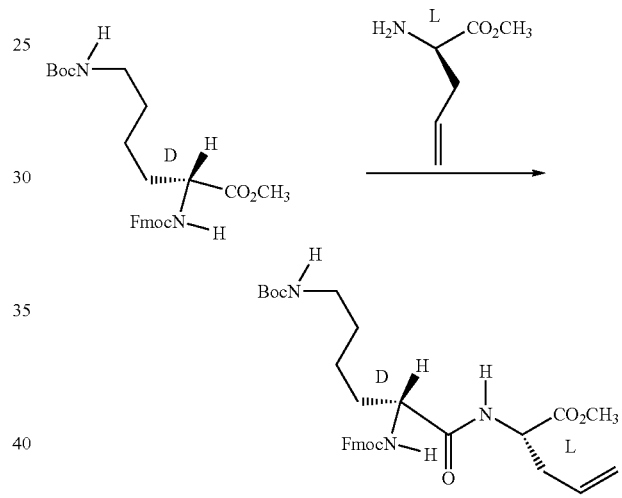

L-Allylglycine methyl ester HCl (0.706 g) was suspended in dry dichloromethane (10 mL) and Fmoc-D-Lysine(BOC) OH (1 equiv.) was added under $N_2$ with stirring, followed by DMAP (0.1 equiv) and diisopropylethyl amine (1.0 equiv). The mixture was cooled to 0° C. and DCC (1.0 equiv) added. The reaction was left to stir at ambient temperature overnight. The suspension was filtered through celite and the solids washed with cold DCM, the filtrate and washings combined and washed twice with water then the solvent was removed by rotary evaporation. The residue was then chromatographed in 2% $CH_3OH/DCM$ to give 76% yield of a pale cream flaky solid.

HRMS Calc. mass 580.3023. Found 580.3018 [M+H], $C_{32}H_{42}N_3O_7$. $^1$H NMR ($CDCl_3$) δ7.76, 2H, d, J=7.5 Hz, H17,17'; 7.59, 2H, d, J=6.9 Hz, H20,20'; 7.40, 2H, t, J=7.2 Hz, H19,19'; 7.31, 2H, ddd, J=9.0, 7.2, 1.2 Hz, H18,18'; 6.7, 1H, br.d, J=6.6 Hz, NH; 5.63, 2H, br. m, NH, H2; 5.10, 1H, d, J=5.4 Hz, H1; 5.05, 1H, s, H1'; 4.65, 2H, H4, NH; 4.38, 2H, d, J=6.6 Hz, H14, H14'; 4.21, 2H, H15, H8; 3.71, 3H, s, $OCH_3$; 3.11, 2H, d, J=6.0 Hz, H12,H12'; 2.52, 2H, m, H3,H3'; 1.85, 2H, m; 1.68, 2H, m; 1.48–1.25, 2H, m; 1.43, 9H, s, t-Bu.

Example 3

Deprotection of the α Amino Group of Nα-Fmoc-Nε-Boc-D-Lysine-L-Allylglycine Methyl Ester

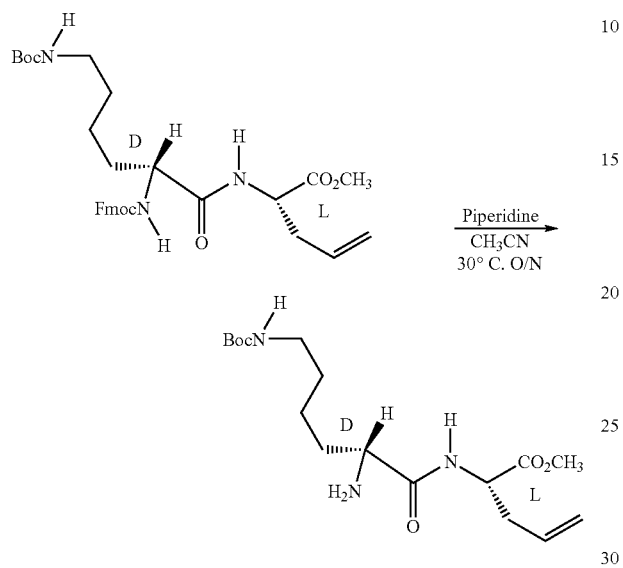

Fmoc-D-Lys(BOC)-L-Allylgly-methyl ester (0.631 g) was dissolved in 10 mL dry acetonitrile and 20 mol % of piperidine in acetonitrile was added. The flask was fitted with a condenser and the reaction stirred under $N_2$ at 30° C. over night. The solvent was then removed to give a pale cream oily semi solid which was chromatographed on silica in 5% methanol in dichloromethane to give the deprotected product (0.389 g (58% yield)) as a cream oil.

MS ES 358.1 [M+H]+ $^1$H NMR 300 MHz (CDCl$_3$) δ7.79, 1H, d, J=8.1 Hz, NH; 5.66, 1H, m, H2; 5.16, 1H, d, J=5.7 Hz, H1; 5.11, 1H, d, J=0.9 Hz, H1'; 4.91, 1H, NH; 4.30, 1H, m, H4; 3.74, 3H, s, OCH$_3$; 3.33, 1H, br s, H8; 3.12, 2H, d, J=6.0 Hz, H12, H12'; 2.56, 2H, m, H3, H3'; 1.87–1.26, 8H, m, H9, H9', H10, H10', H11, H11', NH$_2$; 1.43, 9H, s, 3CH$_3$.

Compounds Based on a 3,3'-Substituted Binaphthyl Nucleus

Example 4

Preparation of (+/−)-2,2'-dimethoxy-1,1'-binaphthyl

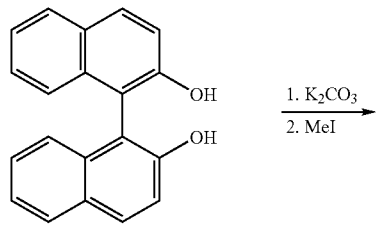

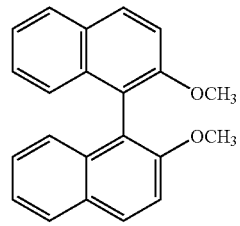

(+/−)-1,1'-Bi-2,2'-naphthol (10.13 g, 35 mmol) was dissolved in acetone (300 mL, 0.12 M). Potassium carbonate (16.69 g, 121 mmol) and methyl iodide (22 mL, 353 mmol) were added and the mixture heated to reflux under nitrogen for 48 h. The cooled reaction mixture was evaporated to dryness, the residue taken up in acetone (60 mL) and water (360 mL) then stirred for 7.5 h. The solid was collected and dried under vacuum at 100° C. overnight yielding (+/−)-2, 2'-dimethoxy-1,1'-binaphthyl as a colourless solid (10.76 g, 97%), (lit.[10] 224–225° C.).

$^1$H NMR δ3.75, s, 6H, OCH$_3$; 7.10, br d, J=8 Hz, 2H; 7.20, dt, J=1.5, 8 Hz, 2H; 7.30, ddd, J=1.5, 7, 8 Hz, 2H; 7.45, d, J=9 Hz, 2H; 7.86, d, J=7.5 Hz, 2H; 7.96, d, J=9 Hz, 2H, ArH.

Example 5

Preparation of (+/−)-3,3'-diiodo-2,2'-dimethoxy-1,1'-binaphthyl

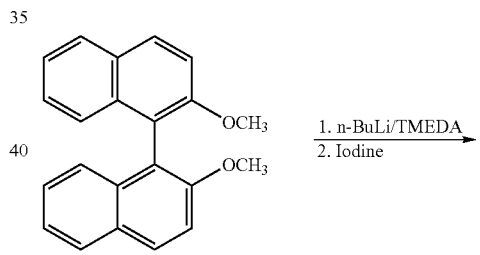

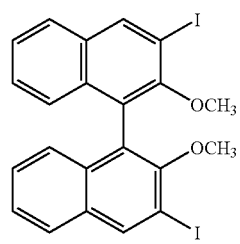

To a solution of TMEDA (1.0 mL, 6.6 mmol) in diethyl ether (50 mL) was added a solution of n-butyl lithium (1.6 M in hexanes, 4.4 mL, 7.0 mmol). The resulting solution was stirred for 15 min at room temperature. (+/−)-2,2'-Dimethoxy-1,1'-binaphthyl (1.038 g, 3.3 mmol) was added as a solid to the reaction mixture which was then stirred for 3 h at room temperature. The reaction mixture was then cooled to −80° C. and iodine (2.8 g, 11.0 mmol) was added over several minutes using an addition tube. The reaction mixture was allowed to gradually warm to room temperature and was stirred overnight. The reaction mixture was stirred with a solution of saturated aqueous sodium sulfite (added cautiously) for 4 h at room temperature. The reaction mixture was partitioned between dichloromethane (200 mL) and water (200 mL). The organic layer was dried (MgSO$_4$/Na$_2$SO$_4$), filtered and the filtrate evaporated to dryness. The resulting deep yellow oil was purified by flash column chromatography (5% ethyl acetate/hexane) to yield (+/−)-3,3'-diiodo-2,2'-dimethoxy-1,1'-binaphthyl as a pale yellow crystalline solid (0.954 g, 51%).

$^1$H NMR δ3.41,s, 6H, 2×OCH$_3$; 7.07, d, J=8 Hz, 2H; 7.26, ddd, J=1.5, 7, 8 Hz, 2H; 7.40, ddd, J=1, 7, 8 Hz, 2H; 7.79, d, J=8 Hz, 2H, ArH; 8.53, s, 2H, ArH4, 4'. $^{13}$C NMR δ61.1, OCH3; 92.3, 125.3, 4° ArC; 125.6, 125.75, 126.9, 127.05, 132.2, 4° ArC; 133.8, 4° ArC; 139.9, 154.5, 4° ArC. m/z (CI, +ve) 567 (100%). C$_{22}$H$_{16}$I$_2$O$_2$+H$^+$ requires 567.

The by-product from this reaction is (+/−)-3-iodo-2,2'-dimethoxy-1,1'-binaphthyl, which is separated from (+/−)-3,3'-diiodo-2,2'-dimethoxy-1,1'-binaphthyl using chromatography.

Example 6

Preparation of (+/−)-3-iodo-2,2'-dimethoxy-3'-methyl-1,1'-binaphthyl

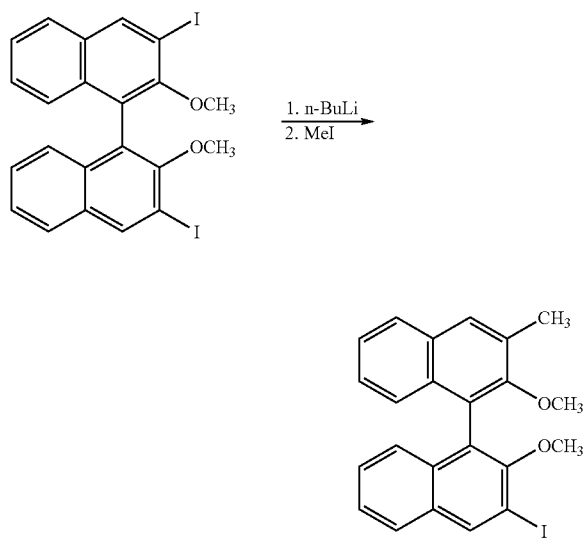

To a −80° C. solution of (+/−)-3,3'-diiodo-2,2'-dimethoxy-1,1'-binaphthyl (2.016 g, 3.6 mmol) in THF (dry, distilled, 80 mL, 0.044 M) was added n-butyl lithium (2.8 mL, 3.9 mmol) dropwise. The reaction mixture turned yellow and was stirred for 1 h before the addition of methyl iodide (dry, distilled, 0.35 mL, 5.6 mmol). The reaction mixture was allowed to gradually warm to room temperature. After stirring for a further 3 h saturated aqueous ammonium chloride solution (4 drops) was added. The reaction mixture was evaporated to dryness, the residue taken up in diethyl ether and washed with water. The organic layer was dried (MgSO$_4$), filtered and the filtrate evaporated to dryness to give a pale yellow solid. Purification of the crude material by flash column chromatography (4% ethyl acetate/hexane) yielded (+/−)-2,2'-dimethoxy-3-iodo-3'-methyl-1,1'-binaphthyl.

$^1$H NMR δ2.55, s, 3H, CH$_3$; 3.36, s, 6H, OCH$_3$; 7.06, d, J=8 Hz, 1H; 7.12, d, J=8 Hz, 1H; 7.16–7.42, m, 2H, ArH; 7.80, t, J=8 Hz, ArH; 7.81, s, 3H,ArH4"; 8.52, s, ArH4.

The product also contained (+/−)-3,3'-diiodo-2,2'-dimethoxy-1,1'-binaphthyl (10%) and (+/−)-2,2'-dimethoxy-3,3'-dimethyl-1,1'-binaphthyl (8%).

Other reaction products seperated by chromatography were (+/−)-2,2'-dimethoxy-3-iodo-1,1'-binaphthyl and (+/−)-2,2'-dimethoxy-3-methyl-1,1'-binaphthyl.

Example 7

Preparation of (+/−)-3-bromomethyl-3'-iodo-2,2'-dimethoxy-1,1'-binaphthyl

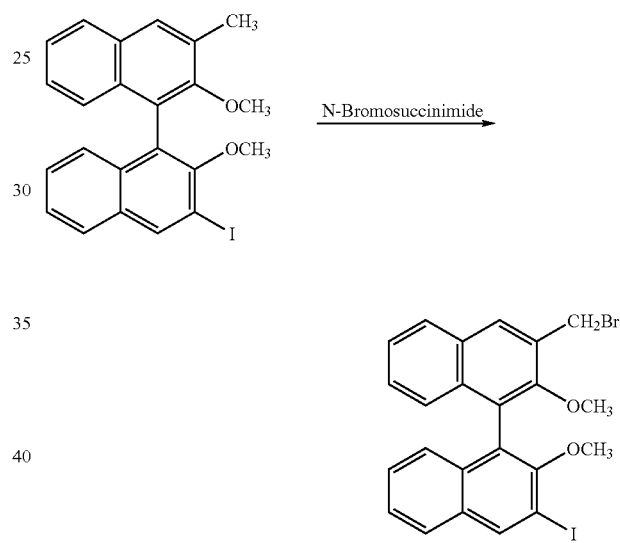

(+/−)-3-Iodo-2,2'-dimethoxy-3'-methyl-1,1'-binaphthyl (1.737 g, 3.8 mmol) was dissolved in carbon tetrachloride (100 mL) and N-bromosuccinimide (1.316 g, 7.4 mmol) was added. The mixture was heated to reflux followed by external irradiation of the pyrex flask with a 500 W mercury lamp for 1 h. The cooled reaction mixture was filtered (to remove succinimide), the filtrate evaporated to dryness to give a red solid. The residue was purified by flash column chromatography (4% ethyl acetate/hexane) to yield a colourless crystalline solid (1.130 g) that was a mixture containing (+/−)-3-bromomethyl-3'-iodo-2,2'-dimethoxy-1,1'-binaphthyl (0.942 g, 46%).

$^1$H NMR δ3.36, s, 3H, OCH$_3$; 3.40, s, 3H, OCH$_3$; 4.72 d, J=9.9 Hz, 1H, CH$_{2,A}$; 4.91, d, J=9.9 Hz, 1H,CH$_{2B}$; 7.08, d, J=8 Hz, 1H; 7.18, d, J=8 Hz, 1H; 7.23–7.44, m, 4H; 7.80, d, J=8 Hz, 1H; 7.88, d, J=8 Hz, 1H, ArH; 8.07, s, 1H, ArH4 and 8.54, s, 1H, ArH4'.

The other component was found to be (+/−)-3-bromo-3'-bromomethyl-2,2'-dimethoxy-1,1'-binaphthyl (0.188 g, 10%).

Example 8

Preparation of ethyl (+/−)-3-[3-(2,2'-dimethoxy-3'-iodo-1,1'-binaphthyl)]-2-[(diphenylmethylene)amino]propanoate

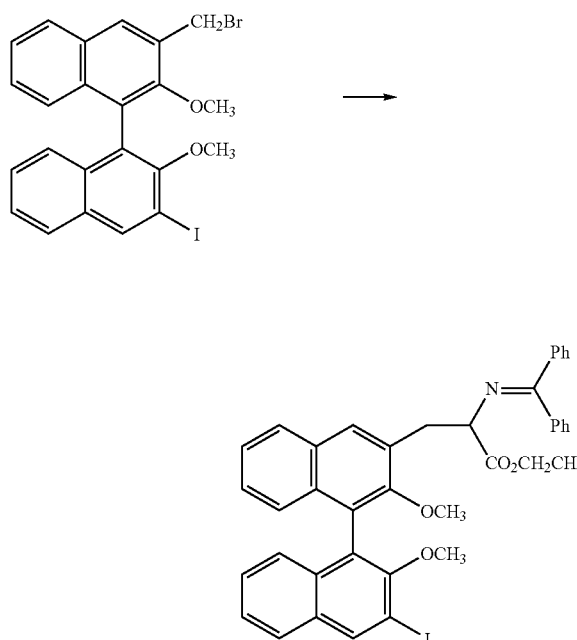

To a −10° C. solution of HMPA (0.7 mL, 4.02 mmol) and diisopropylamine (0.24 mL, 1.71 mmol) in THF (dry, distilled, 40 mL) was added n-butyllithium (1.32 M in hexanes, 1.4 mL, 1.85 mmol). The pale yellow solution was stirred for 10 min then cooled to −78° C.

To this solution was added a solution of ethyl N-(diphenylmethylene)glycinate (0.450 g, 1.68 mmol) in THF (dry, distilled, 20 mL) using a cannula and precooling the addition solution by running the drops down the side of the receiving flask. The resulting mixture was stirred for 30 min then a solution of 3-bromomethyl-2,2'-dimethoxy-3'-iodo-(+/−)-1,1'-binaphthyl (0.895 g, 1.68 mmol) in THF (dry, distilled, 40 mL) was added using a cannula. The reaction mixture was allowed to slowly warm to room temperature and stirred over night. The yellow solution was quenched with aqueous ammonium chloride solution (1 mL). The reaction mixture was evaporated to dryness to give a yellow oil that contained ethyl (+/−)-3-[3-(2,2'-dimethoxy-3'-iodo-1,1'-binaphthyl)]-2-[(diphenylmethylene)amino]propanoate. The residue was used without further purification, due to the presence of HMPA.

$^1$H NMR δ1.21, t, J=5 Hz, 3H, CH$_3$; 3.00, s, 3H, OCH$_3$; 3.20, s, 3H, OCH$_3$; 3.40, dd, J=7, 10 Hz, 1H, CH$_{2A}$; 3.71, dd, J=3, 10 Hz, 1H, CH$_{2B}$; 4.11–4.22, m, 2H, OCH$_2$; 4.50, q, J=3 Hz, 1H, α-CH; 6.82, d, J=5 Hz, 1H, NH; 7.78–6.98, m, 19H, ArH; 8.49, s, 1H, ArH.

Example 9

Preparation of ethyl (+/−)-2-amino-3-[3-(2,2'-dimethoxy-3'-iodo-1,1'-binaphthyl)]propanoate hydrochloride salt

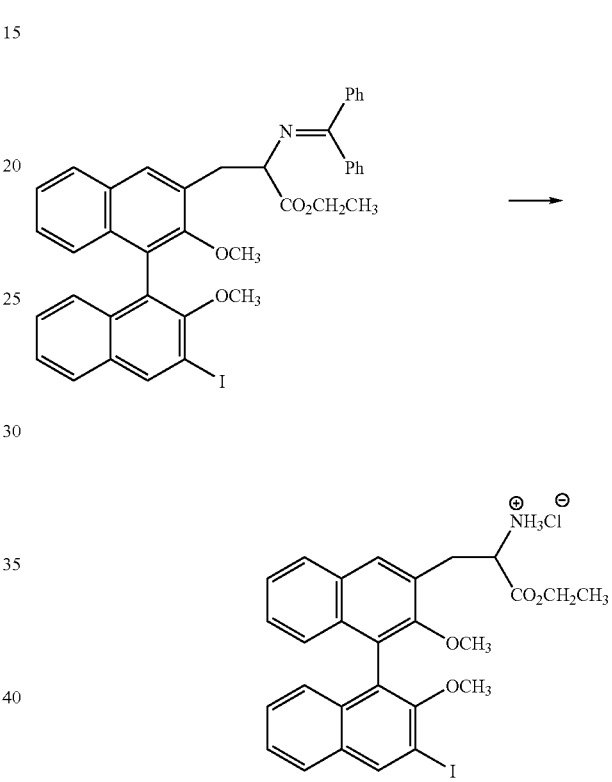

To a solution of the crude alkylated product from Example 8 (1.208 g, 1.68 mmol) in diethyl ether (30 mL) was added 3% aqueous hydrogen chloride solution (15 mL, 4.6 mmol). The mixture was stirred at RT overnight and gave a yellow oil underneath the aqueous layer underneath a yellow organic layer. The mixture was evaporated to dryness, the sticky yellow residue was taken up in ethanol and evaporated to dryness. This was repeated twice more. The final residue was dried under high vacuum then freeze dried. The crude product was used without further purification.

$^{13}$C NMR δ13.8, 13.9, ArCH$_3$; 33.0, 33.6, ArCH$_2$; 53.2, 53.7, OCH$_2$; 61.0, 61.1, 61.2, 62.3, OCH$_3$; 92.3, α-CH; 117.4, 124.1, 124.2, 125.1, 125.3, 125.5, 125.6, 125.8, 126.0, 126.2, 126.5, 126.7, 126.75, 126.9, 127.05, 127.65, 127.85, 128.2, 130.0, 130.4, 131.3, 132.0, 132.1, 132.4, 132.8, 132.9, 133.3, 134.8, 133.9, 134.1, 139.7 (×2), 152.5, 154.4, 154.7, 154.9, ArC; 168.6, 169.0, C═O.

Example 10

Preparation of ethyl (+/−)-2-acetylamino-3-[3-(2,2'-dimethoxy-3'-iodo-1,1'-binaphthyl)]propanoate

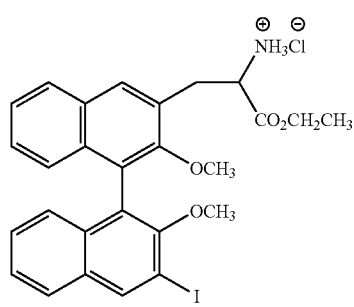

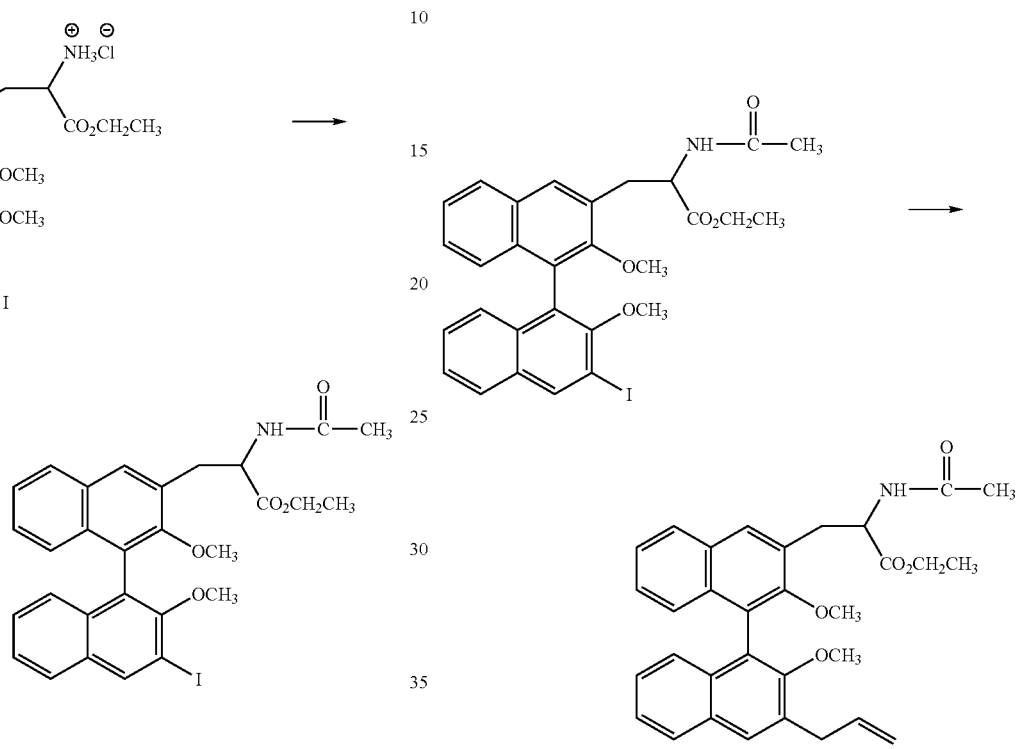

The residue obtained after acid hydrolysis containing the binaphthyl salt obtained in Example 9 (0.993 g, 1.68 mmol) was dissolved in dichloromethane (dry, distilled, 100 mL). The solution was stirred with $MgSO_4$ (anhydrous) briefly then cooled in an ice/salt bath. Triethylamine (0.70 mL, 5.02 mmol) was added, followed by acetic anhydride (0.4 mL, 4.24 mmol) and DMAP, after stirring for 5 min. The reaction mixture was allowed to warm to room temperature and was stirred overnight. To the reaction mixture was added a solution of 3% aqueous hydrochloric acid (50 mL) and dichloromethane (50 mL). The aqueous layer was removed and extracted with dichloromethane. The combined organic layers were washed with a solution of 3% aqueous hydrochloric acid (×1), a solution of 1:1 aqueous saturated lithium chloride and water (×2) then water (×1). The solution was dried ($MgSO_4$) and the filtrate evaporated to dryness to give a yellow liquid. The crude product was purified by squat column chromatography (10% ethyl acetate/hexane→ethyl acetate) to yield ethyl (+/−)-2-acetylamino-3-[3-(2,2'-dimethoxy-3'-iodo-1,1'-binaphthyl)]propanoate as a pale yellow solid (0.75 g, 75% from (+/−)-3-bromomethyl-3'-iodo-2,2'-dimethoxy-1,1'-binaphthyl)(ave. 91% yield per step).

$^1$H NMR δ1.25, t, J=7 Hz, 3H, $CH_3$; 1.98, s, 3H, $COCH_3$; 3.26, s, $OCH_3$; 3.28, s, 3H, $OCH_3$; 3.30–3.42, m, $ArCH_2$; 4.23, m, $OCH_2$; 4.73, q, J=7 Hz, 1H, α-CH; 6.79, d, J=7 Hz, 1H, NH; 7.05–7.82, ArH; 7.86, s, 1H, ArH4; 8.535, s, 1H, ArH4'.

Example 11

Preparation of ethyl (+/−)-2-acetylamino-3-[3-(3'-allyl-2,2'-dimethoxy-1,1'-binaphthyl)]propanoate To a solution of the binaphthyl derivative obtained from Example 10 (0.740 g, 1.24 mmol) in 1,4-dioxane (dry, 40 mL) was added palladium chloride (0.025 g, 0.14 mmol) and triphenylphosphine (0.136 g, 0.52 mmol). The solution was deoxygenated with argon for 10 min then allyltributyltin (0.39 mL, 1.26 mmol) was added. The resulting mixture was heated at reflux for 5 h. After cooling the solution was filtered through celite and evaporated to dryness. The residue was purified by squat column chromatography, to remove stannanes, then flash column chromatography (50% ethyl acetate/hexane) to give a mixture that contained ethyl (+/−)-2-acetylamino-3-[3-(3'-allyl-2,2'-dimethoxy-1,1'-binaphthyl)]propanoate as a clourless oil (0.54 g, 85%).

$^1$H NMR δ0.92, t, J=7 Hz; 1.26, t, J=7 Hz, 3H,$CH_3$; 1.98, s; 2.04, s, 3H; $COCH_3$; 3.17, s, 3H, $OCH_3$; 3.235, s, 3H, $OCH_3$; 3.25–3.33, m, 2H, $CH_2$; 3.58–3.72, br m, 2H, $CH_2$; 4.12, q, J=7 Hz, ($OCH_2$); 4.21, q, J=7 Hz, 2H, $OCH_2$; 4.71, q, J=7 Hz, α-CH; 4.84, q, J=5 Hz, 1H, α-CH; 5.125–5.19, m, 2H, =$CH_2$; 6.08–6.22, m, 1H, CH=; 6.78, d, J=7 Hz; 6.91, d, J=7 Hz, 1H, NH; 7.14–7.26, m, 4H, ArH; 7.35–7.46, m, 2H, ArH; 7.81–7.85, m, 4H, ArH. m/z (CI, +ve) 512 (100%). $C_{32}H_{33}NO_5$+$H^+$ requires 512.

The other product in this mixture is ethyl (+/−)-2-acetylamino-3-[3-(3'-bromo-2,2'-dimethoxy-1,1'-binaphthyl)]propanoate.

Example 12

Preparation of (+/−)-2-acetylamino-3-[3-(3'-allyl-2,2'-dimethoxy-1,1'-binaphthyl)]propanoic acid

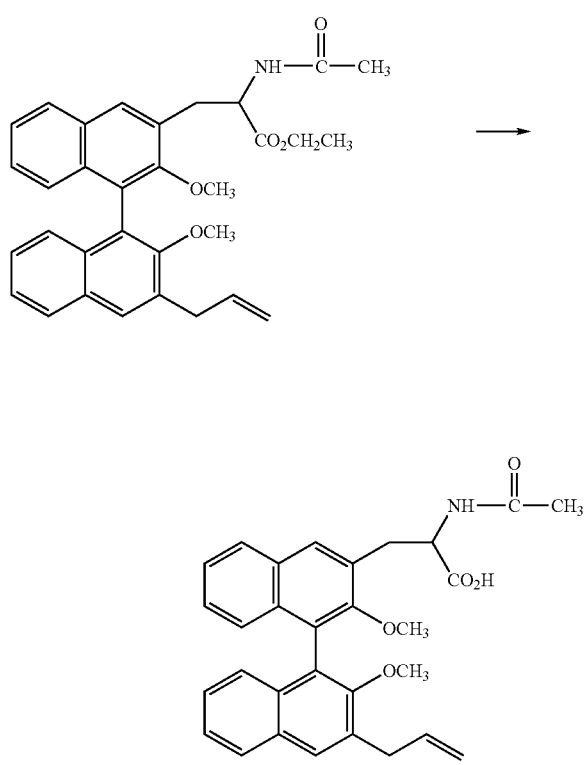

The binaphthyl derivative obtained in Example 11 (0.522 g, 1.02 mmol) was dissolved in THF (22 mL) and cooled in an ice/water bath. To this solution was added a solution of lithium hydroxide monohydrate (0.196 g, 4.67 mmol) in water (9 mL). The mixture was allowed to gradually warm to room temperature and was stirred for 5 h. To the reaction mixture was added diethyl ether, the aqueous layer was washed with ether and the combined ether layers extracted with water (×2). The combined aqueous layers were acidified (3% aq. HCl), extracted with diethyl ether (×3) and dried (MgSO$_4$). The filtrate was evaporated to dryness to give (+/−)-2-acetylamino-3-[3-(3'-allyl-2,2'-dimethoxy-1,1'-binaphthyl)]propanoic acid as a white solid (0.462 g, 94%).

$^1$H NMR δ2.07, s, 3H, COCH$_3$; 3.07, s, 3H, OCH$_3$; 3.20, s, 3H, OCH$_3$; 3.28–3.77, m, 2×CH$_2$; 4.55, 2×t, J=5 Hz, 1H, α-CH; 5.11–5.19, m, 2H, =CH$_2$; 6.07–6.20, m, 1H, CH=; 7.16–7.56, m, 6H, ArH; 7.74, br s, 1H, NH; 7.84, d, J=8 Hz, ArH; 7.88, s, 4H, ArH4, 4'.

Example 13 methyl (aR/S,2S,5R)-8-acetamido-2-allyl-9-{3-[3'-allyl-2,2'-dimethoxy-1,1'-binaphthyl]}-3,6-diaza-5-(4-{[(tert-butoxy)carbonyl]amino}butyl)-4,7-dioxononanoate The binaphthyl derivative obtained from Example 12 (0.258 g, 0.53 mmol) was dissolved in dichloromethane (dry, 3 mL) and a solution of the dipeptide obtained from Example 3 (freshly deprotected) (0.22 g, 0.61 mmol) in dichloromethane (3 mL) was added. To the resulting solution was added 4-dimethylaminopyridine (crystal) and then the solution was cooled in an ice/water bath. To the chilled solution was added 1,3-dicyclohexylcarbodiimide (0.111 g, 0.54 mmol). The reaction mixture was allowed to warm to room temperature and was stirred overnight. To the reaction mixture was added dichloromethane (10 mL) which was then filtered through celite. The filtrate was evaporated to give the amide as a pale yellow crystalline solid (0.404 g, 92%). m/z (ES, +ve) 823 (M+H$^+$, product, 32%), 723 (823-Boc, 8), 565 (11), 428 (19), 358 (21), 302 (26) and 225 (DCU+H$^+$, 100). C$_{47}$H$_{58}$N$_4$O$_9$+H$^+$ requires 823.

Example 13A

Preparation of benzyl (aR/S,2S,5R)-8-acetamido-2-allyl-9-{3-[3'-allyl-2,2'-dimethoxy-1,1'-binaphthyl]}-3,6-diaza-5-(4-{[(tert-butoxy)carbonyl]amino}butyl)-4,7-dioxononanoate The corresponding allylglycine benzyl ester of the compound of Example 13 was prepared by similar methods as described above except that the appropriate benzyl precursor was used. The amino group of the lysine side chain was deprotected according to the procedure of Example 15 to give the target compound.

Example 13B benzyl (aR/S,2S,5R)-8-acetamido-2-allyl-9-{3-[3'-allyl-2,2'-dimethoxy-1,1'-binaphthyl]}-5-(4-aminobutyl)-3,6-diaza-4,7-dioxononanoate hydrochloride

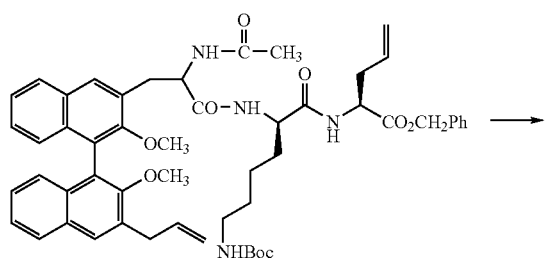

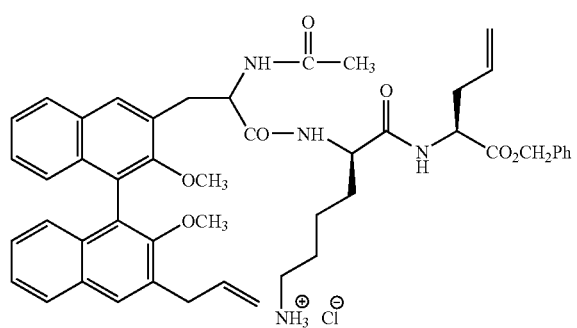

Prepared from the product obtained from Example 13 (0.0226 g, 0.025 mmol) using the method as set out in Example 15. The product was isolated as a pale yellow solid (0.014 g, 67%).

m/z (ES, +ve) 839 (M+CH$_3$CN, 1%), 837 (M+K$^+$, 1), 799 (M+H$^+$, 19), 626 (2), 449 (4), 338 (6) and 225 (DCU+H$^+$, 100).

Example 14

Preparation of (aR/S,7R,10S)-4-acetamido-6,9-diaza-7-(4-{[(tert-butoxy)carbonyl]amino}butyl)-10-methoxycarbonyl-1(1,3),2(1,3)-di(2-methoxynaphthalena)-5,8-dioxocyclotetradecaphane-12-ene

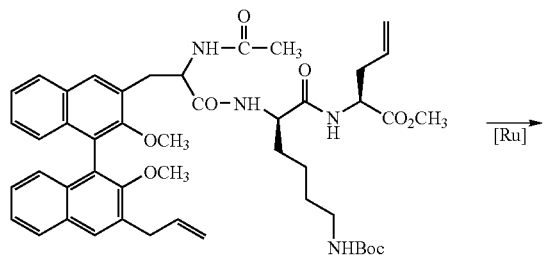

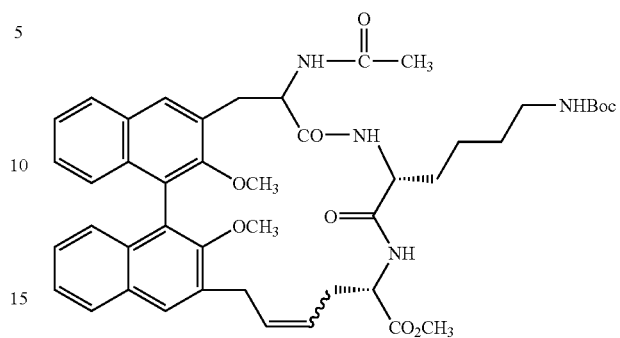

The binaphthyl derivative obtained in Example 13 (0.205 g, 0.25 mmol) was dissolved in dichloromethane (50 mL). The solution was deoxygenated with argon gas for 10 min before the addition of benzylidene-bis(tricyclohexylphosphine)dichlororuthenium (0.022 g, 0.027 mmol). The reaction mixture was heated to reflux for 18 hours. The cooled reaction mixture was evaporated to dryness and the resulting residue purified by flash column chromatography to give three fractions each of which contained different diasteriomeric cyclic products;

1) Pale yellow glass like solid (0.038 g). m/z (ES, +ve) 817 (M+Na$^+$, 4%), 795 (M+H$^+$, 16), 593 (48) and 297 (O=P(C$_6$H$_{11}$)$_3$+H$^+$, 100);

2) Light brown solid (0.041 g). m/z (ES, +ve) 795 (M+H$^+$, 54%), 593 (35), 297 (O=P(C$_6$H$_{11}$)$_3$+H$^+$, 100), 145 (44), 104 (33) and 86 (64);

3) Very pale yellow glass like solid (0.073 g)(Total=0.152 g, 74%). m/z (ES, +ve) 795 (M+H$^+$, 15%), 297 (O=P(C$_6$H$_{11}$)$_3$+H$^+$, 29), 147 (32), 145 (66), 106 (16), 104 (52) and 86 (100). C$_{45}$H$_{54}$N$_4$O$_9$+H$^+$ requires 795.

Example 15

Preparation of (aR/S,7R,10S)-4-acetamido-7-(4-aminobutyl)-6,9-diaza-10-methoxycarbonyl-1(1,3),2(1,3)-di(2-methoxynaphthalena)-5,8-dioxocyclotetradecaphane-12-ene hydrochloride

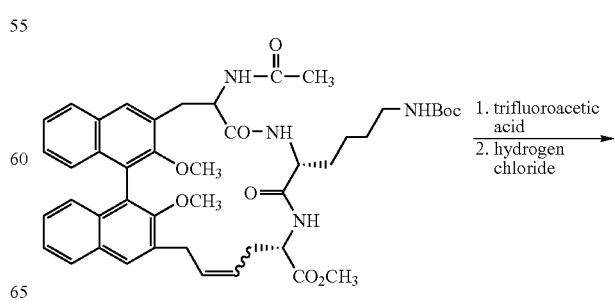

-continued

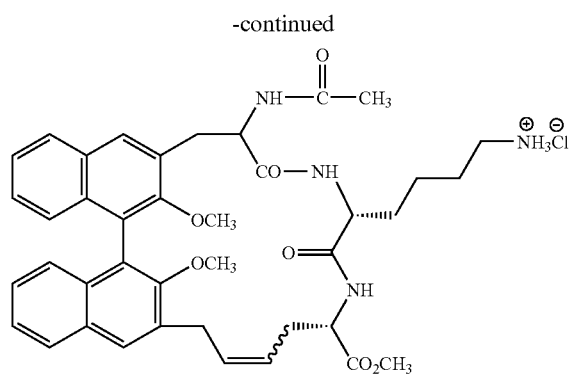

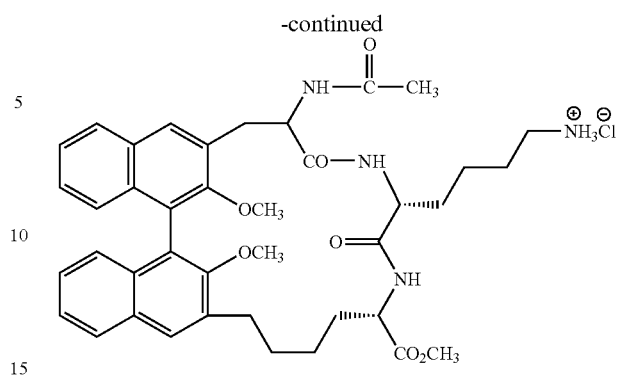

The protected diasteriomeric cyclic peptoids prepared in Example 14 (0.073 g, 0.09 mmol) were dissolved in dichloromethane (2 mL) then trifluoroacetic acid (2 mL) was added. The mixture was stirred at room temperature for 25 min. The mixture was evaporated to dryness, the residue taken up in dichloromethane and evaporated to dryness again. This was repeated twice more. The residue was taken up in dichloromethane (3 mL) and a solution of 1.0 M hydrogen chloride in diethyl ether (1 mL) was added. The resulting mixture was stirred at room temperature for 10 min before being evaporated to dryness. The residue was taken up in dichloromethane and evaporated to dryness again. This was repeated twice more. The deprotected product was crystallised from the residue with diethyl ether and dichloromethane. The product was isolated using centrifugation to yield the deprotected cyclic product as a pale yellow crystalline solid (0.055 g, 82%). m/z (ES, +ve) 696.5 (41%) and 695.8 (53) and 695.4 (M+H$^+$, 73) (aggregates), 111 (48) and 60 (100). $C_{40}H_{46}N_4O_7$+H$^+$ requires m/z 695.3445. Found 695.3400.

Similarly other diastereomers were also obtained—(0.021 g, 60%) m/z (ES, +ve) 697 (32%) and 696 (100) and 695 (M+H$^+$, 96) (aggregates), $C_{40}H_{46}N_4O_7$+H$^+$ requires m/z 695.3445. found 695.3435; and (0.023 g, 60%), m/z (ES, +ve) 696 (9%), 695 (M+H$^+$, 20); 111 (12) and 60 (100); $C_{40}H_{46}N_4O_7$+H$^+$ requires m/z 695.3445. found 695.3427.

Example 15A (aR/S,7R,10S)-4-acetamido-7-(4-aminobutyl)-6,9-diaza-10-methoxycarbonyl-1(1,3),2(1,3)-di(2-methoxynaphthalena)-5,8-dioxocyclotetradecaphane hydrochloride

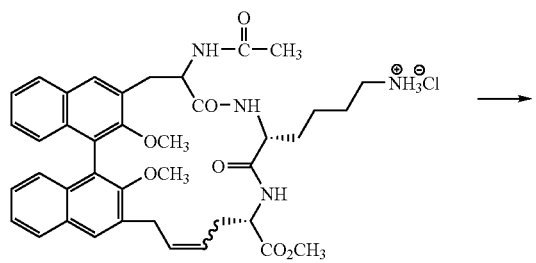

One of the isomers of the deprotected cyclized peptoid obtained from Example 15 was dissolved in a mixture of dichloromethane (0.2 mL), methanol (0.5 mL) and water (0.2 mL). To this solution was added 10% Pd/C (0.001 g, 0.0009 mmol) and the reaction vessel was sealed. The reaction mixture was stirred and the atmosphere inside the reaction vessel removed and replaced with an atmosphere of hydrogen. This procedure was repeat twice. The reaction was stirred at room temperature for several days before removal of all solid material by passing the reaction mixture through a plug of celite (filter aid). The filtrate was evaporated and gave the reduced deprotected cyclized peptoid as a white solid (0.001 g, 33%).

m/z (ES, +ve) 697 (M+H$^+$, 100%); 316 (51), 288 (74).

Example 15B

Preparation of (aR/S,7R,10S)-4-acetamido-6,9-diaza-10-benzyloxycarbonyl-7-(4-{[(tert-butoxy)carbonyl]amino}butyl)-1(1,3),2(1,3)-di(2-methoxynaphthalena)-5,8-dioxocyclotetradecaphane-12-ene

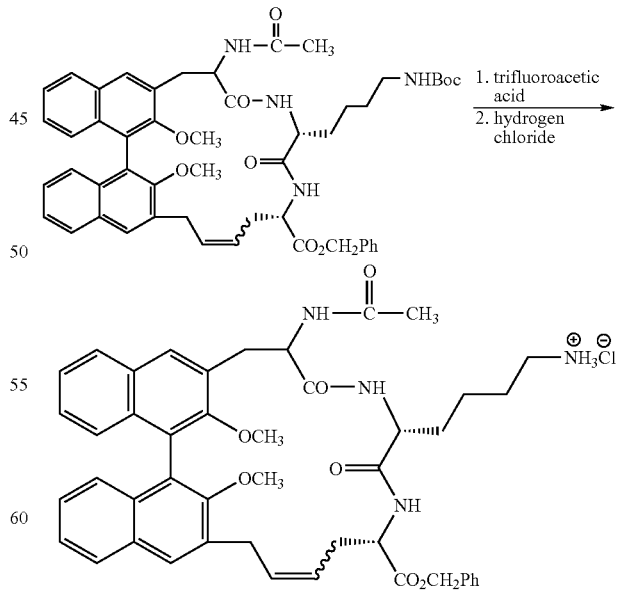

The corresponding benzyl ester of the compound of Example 15 was prepared by similar methods as described above except that the appropriate benzyl precursor was used.

Two isomers were isolated at the protected cyclic peptide stage and these were seperately deprotected to provide the desired products.

m/z (ES, +ve) 771 (M+H$^+$, 100). m/z (ES, +ve) 771 (M+H$^+$, 72%), 699 (7), 59 (100) respectively.

Example 16

Coupling of (+/−)-2-acetylamino-3-[3-(3'-allyl-2,2'-dimethoxy-1,1'-binaphthyl)]propanoic acid with Nε-Fmoc-L-lysine-L-allylglycine methyl ester

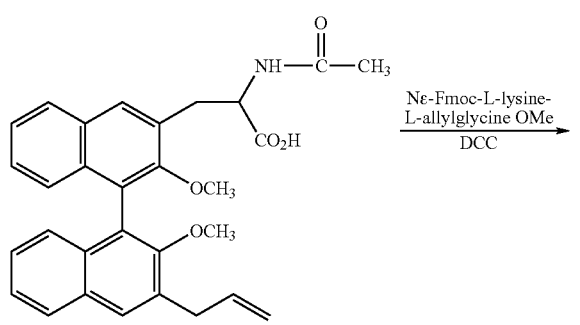

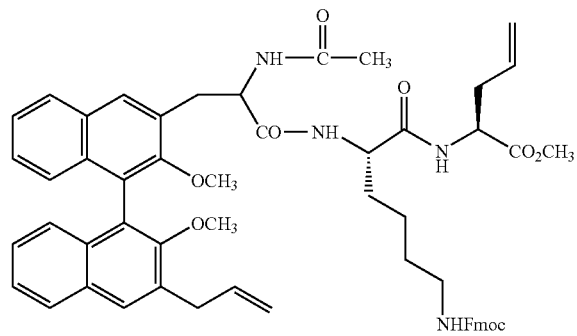

The binaphthyl derivative obtained in Example 12 (0.447 g, 0.92 mmol) was dissolved in dichloromethane (1 mL) and a solution of the Nε-Fmoc-L-lysine-L-allylglycine methyl ester (freshly deprotected) (0.450 g, 0.94 mmol) in dichloromethane (2 mL) was added. To the resulting solution was added 4-dimethylaminopyridine (crystal) and then the solution was cooled in an ice/water bath. To the chilled solution was added 1,3-dicyclohexylcarbodiimide (0.195 g, 0.94 mmol). The reaction mixture was allowed to warm to room temperature and was stirred overnight. To the reaction mixture was added dichloromethane (10 mL) which was then filtered through celite. The filtrate was evaporated to dryness and the residue purified by flash column chromatography to give the coupled product as an off white crystalline solid (0.474 g, 54%).

m/z (ES, +ve) 945 (M+H$^+$, 36%) and 225 (DCU+H$^+$, 100). $C_{57}H_{60}N_4O_9$+H$^+$ requires 945.

Example 17

Preparation of the Protected Cyclic Peptoid

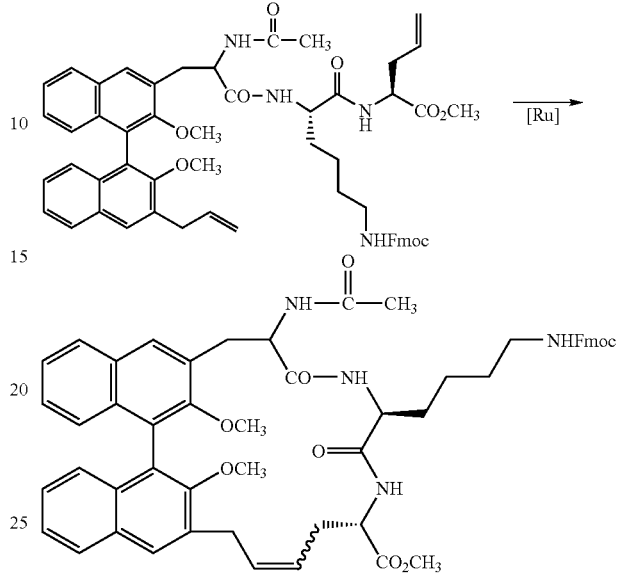

The binaphthyl derivative obtained in Example 16 (0.470 g, 0.50 mmol) was dissolved in dichloromethane (120 mL). The solution was deoxygenated with argon gas for 10 min before the addition of benzylidene-bis(tricyclohexylphosphine)dichlororuthenium (0.022 g, 0.027 mmol). The reaction mixture was heated to reflux for 18 h. The cooled reaction mixture was evaporated to dryness the resulting residue purified by flash column chromatography (4% methanol/dichloromethane) to give the cyclic peptoid product as an off white crystalline solid (0.329 g, 72%).

m/z (ES, +ve) 918 (4%), 917 (M+H$^+$, 5), 593 (9), 522 (3) and 297 (100). $C_{55}H_{56}N_4O_9$+H$^+$ requires 917.

Example 18

Preparation of the Deprotected Cyclic Peptoid

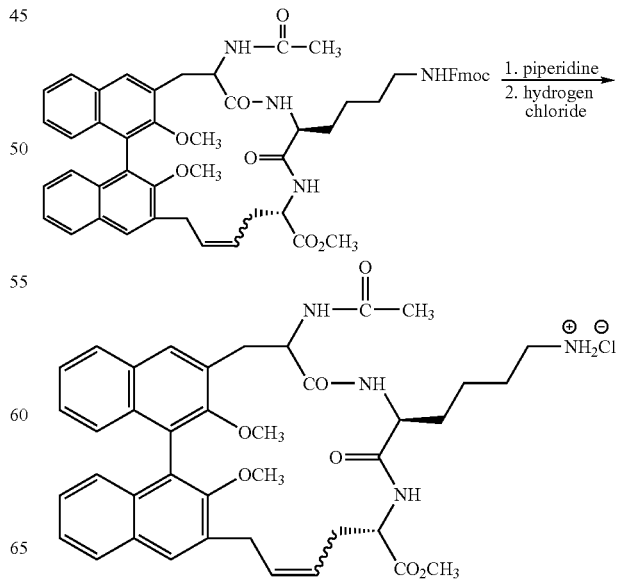

To the protected cyclic peptoid obtained in Example 17 (0.123 g, 0.13 mmol) was added dry acetonitrile (9 mL). The mixture was warmed to 60° C. in a sealed system and a solution of 0.02 M piperidine in acetonitrile (0.54 mL) was added. The reaction mixture was heated at 60° C. for 43 h. The cooled mixture was filtered, and the filtrate evaporated to dryness to give a white solid. The solid was purified by flash column chromatography (10% methanol/dichloromethane, followed by 10% methanol/dichloromethane containing 2% triethylamine). The isolated product was dissolved in dichloromethane (5 mL) and 1.0 M hydrogen chloride in diethyl ether (0.5 mL) was added. The solution was stirred for 10 min then evaporated to dryness and dried under high vacuum to give the deprotected cyclic peptoid product as a pale yellow crystalline solid (0.048, 51%).

m/z (ES, +ve) 729 (30%), 695 (M+H$^+$, 100) and 498 (25). $C_{40}H_{46}N_4O_7$+H$^+$ requires m/z 695.3445. Found 695.3419.

Example 19

Coupling of (+/−)-2-acetylamino-3-[3-(3'-allyl-2,2'-dimethoxy-1,1'-binaphthyl)]propanoic acid with Nω-PMC-L-arginine-L-allylglycine methyl ester were dissolved in dichloromethane (dry, 1.5 mL). To the resulting solution was added 4-dimethylaminopyridine (crystal) and then the solution was cooled in an ice/water bath. To the chilled solution was added 1,3-dicyclohexylcarbodiimide (0.053 g, 0.25 mmol). The reaction mixture was allowed to warm to room temperature and was stirred overnight. To the reaction mixture was added dichloromethane (10 mL) which was then filtered through celite. The filtrate was evaporated to dryness and the residue purified by flash column chromatography (4% methanol/dichloromethane) to give the protected arginine derivative as a colourless solid (0.176 g, 68%).

m/z (ES, +ve) 1056 (M+K$^+$, 4%), 1040 (M+Na$^+$, 16), 1018 (M+H$^+$, 64), 1017 (M$^+$, 100), 920 (13), 624 (14) and 225 (24). $C_{56}H_{68}N_6O_{10}S$ requires 1017.

Example 19A

Preparation of methyl (aR/S,2S,5R)-8-acetamido-2-allyl-9-[3-(3'-allyl-2,2'-dimethoxy-1,1'-binaphthyl)]-3,6-diaza-5-(3-guanidinopropyl)-4,7-dioxononanoate hydrochloride

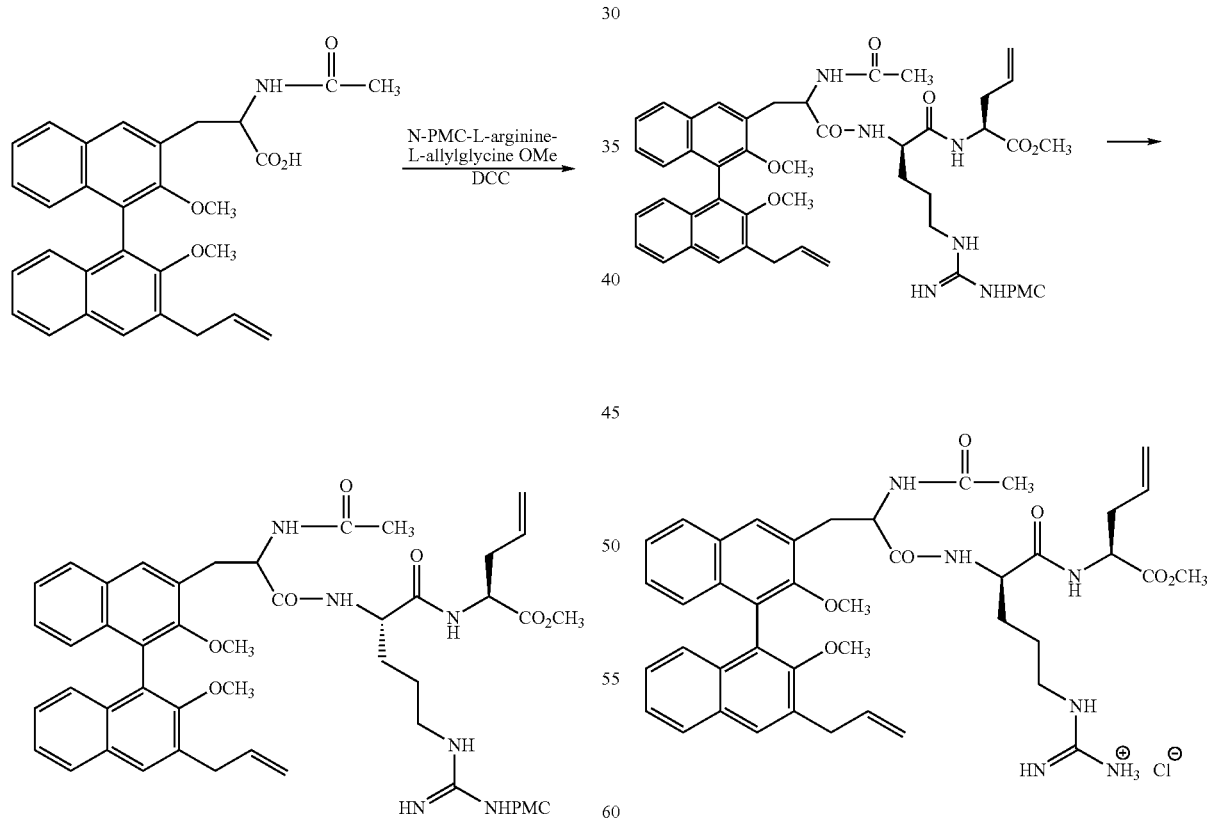

The binaphthyl derivative obtained in Example 12 (0.127 g, 0.26 mmol) and Nω-PMC-L-arginine-L-allylglycine methyl ester (freshly deprotected) (0.150 g, 0.27 mmol)

Similarly to the procedures described above the D-arginyl version of Example 19 was prepared. This was deprotected according to the procedure of Example 21 and isolated as a pale yellow solid.

Example 20

Preparation of the Protected Cyclic Peptoid

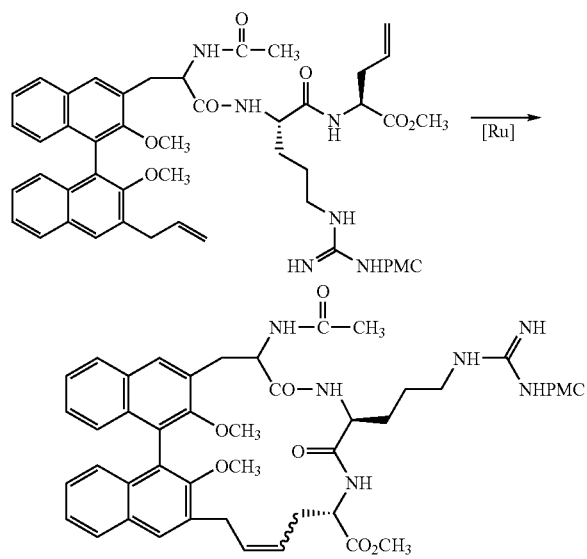

The binaphthyl derivative obtained in Example 19 (0.176 g, 0.17 mmol) was dissolved in dichloromethane (50 mL). The solution was deoxygenated with argon gas for 10 min before the addition of benzylidene-bis(tricyclohexylphosphine)dichlororuthenium (0.015 g, 0.017 mmol). The reaction mixture was heated to reflux for 20 h. The cooled reaction mixture was evaporated to dryness and the resulting residue purified by flash column chromatography (4% methanol/dichloromethane) to give the cyclic peptoid product as a light brown glass (0.132 g, 77%).

m/z (ES, +ve) 1011 (M+Na$^+$) and 989 (M+H$^+$). $C_{54}H_{64}N_6O_{10}S+H^+$ requires 989.

Example 21

Preparation of (aR/S,7S,10S)-4-acetamido-6,9-diaza-7-(3-guanidinopropyl)-10-methoxycarbonyl-1 (1,3),2(1,3)-di(2-methoxynaphthalena)-5,8-dioxocyclotetradecaphane-12-ene hydrochloride

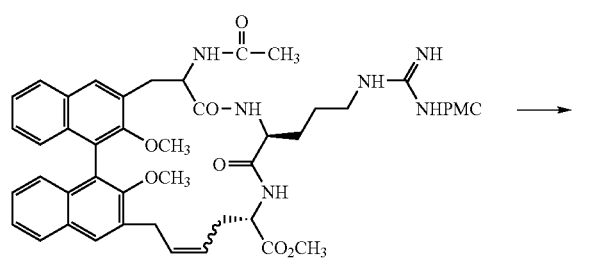

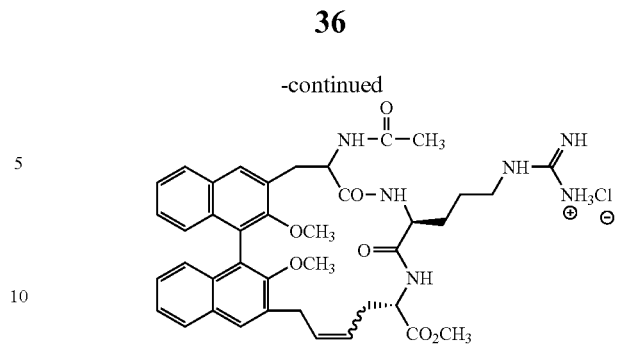

The cyclic peptoid obtained in Example 20 (0.047 g, 0.05 mmol) was dissolved in dichloromethane (2 mL) then trifluoroacetic acid (2 mL) was added. The mixture was stirred at room temperature for 25 min. The mixture was evaporated to dryness, the residue taken up in dichloromethane and evaporated to dryness again. This was repeated twice more. The residue was taken up in dichloromethane (3 mL) and a solution of 1.0 M hydrogen chloride in diethyl ether (1 mL) was added. The resulting mixture was stirred at room temperature for 10 min before being evaporated to dryness. The residue was taken up in dichloromethane and evaporated to dryness again. This was repeated twice more. The deprotected product was crystallised from the residue with diethyl ether and dichloromethane. The deprotected product was isolated using centrifugation and yielded an off white solid (0.021 g, 58%).

m/z (ES, +ve) 724 (100%). $C_{40}H_{46}N_6O_7+H^+$ requires m/z 723.3506. Found 723.3488.

Example 21A

Preparation of (aR/S,7R,10S)-4-acetamido-6,9-diaza-7-(3-guanidinopropyl)-10-methoxycarbonyl-1 (1,3),2(1,3)-di(2-methoxynaphthalena)-5,8-dioxocyclotetradecaphane-12-ene hydrochloride

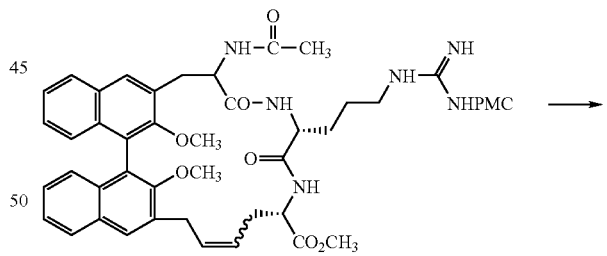

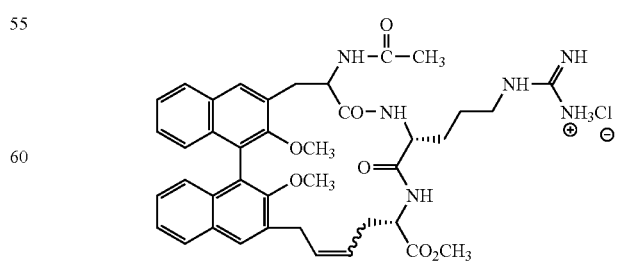

Similarly to the procedures described above the D-arginyl version of Example 21 was prepared and the isomers of the deprotected cyclic peptoid that contains a D-arginine residue were isolated as an off-white solid and a pale yellow solid respectively.

m/z (ES, +ve) 723 (M+H$^+$, 15), 316 (28), 288 (78), 217 (100), 199 (79), 111 (41) and m/z (ES, +ve) 723 (M+H$^+$, 30), 316 (51), 288 (100), 217 (34) and 199 (45) respectively.

Example 21B

Preparation of (aR/S,7R,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane hydrochloride Preparation of a Reduced Cyclic Peptoid that Contains an D-Arginine Residue

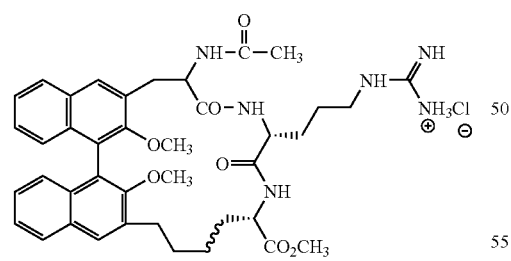

The cyclized peptoid of Example 21A was dissolved in methanol (2 mL). To this solution was added 10% Pd/C (0.012 g, 0.01 mmol) and the reaction vessel was sealed. The reaction mixture was stirred and the atmosphere inside the reaction vessel removed and replaced with an atmosphere of hydrogen. This procedure was repeat twice. The reaction was stirred at room temperature for several days before removal of all solid material by passing the reaction mixture through a plug of celite (filter aid). The filtrate was evaporated and gave the reduced cyclic peptoid as a light brown solid.

m/z (ES, +ve) 725 (M+H$^+$, 19%), 394 (13), 316 (71), 288 (100), 180 (37) and 111 (47).

Example 22

Preparation of Cyclic Tetra Peptoid

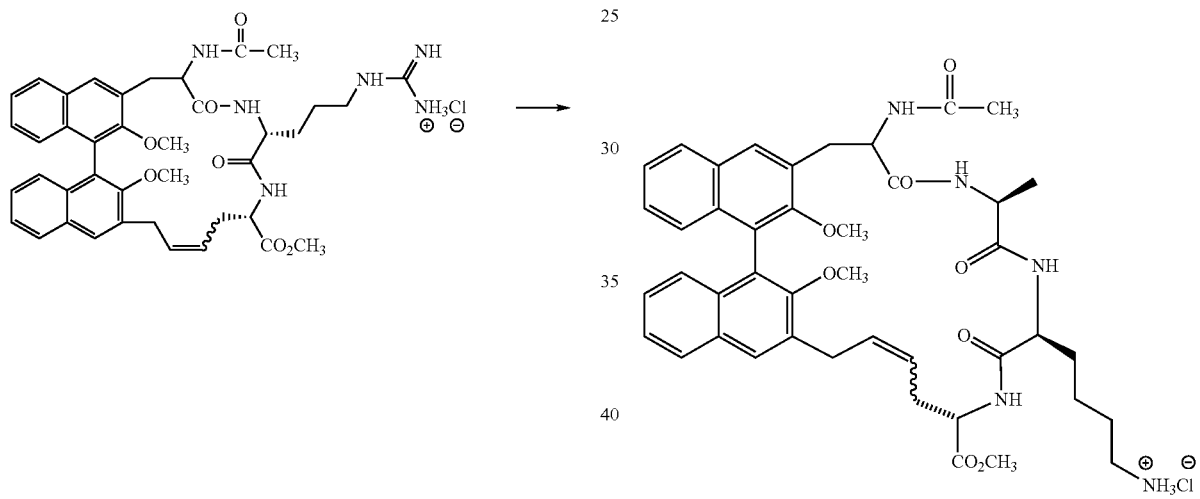

This compound was prepared in a similar manner to the compound of Example 18 but the aminoacyl moiety used in the coupling reaction contained an additional alanine residue.

m/z (ES, +ve) 766.5 (100%), 767 (79) and 767.5 (58). $C_{43}H_{51}N_5O_8$+H$^+$ requires m/z 766.3816. found 766.3740.

Compounds Based on a 3,6-Substituted Carbazole Nucleus

The preparation of 6-acetamido-8,11-diaza-14-ene-9-(3-guanidinopropyl)-12-methoxycarbonyl-7,10-dioxo-[12](3,6)-1H-carbazolophane HCl described in Examples 23 to 35 is shown schematically in Scheme 1.

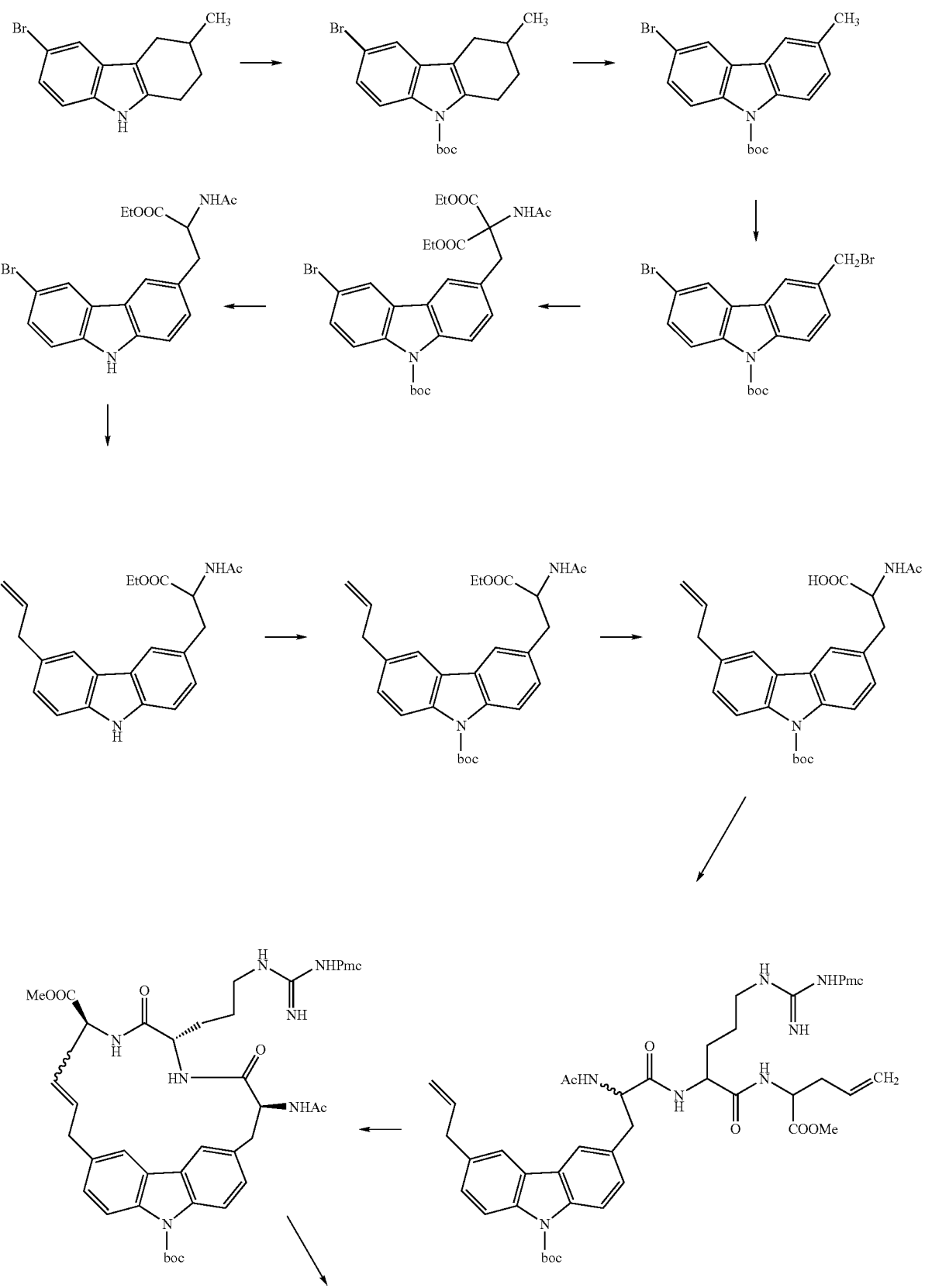

-continued

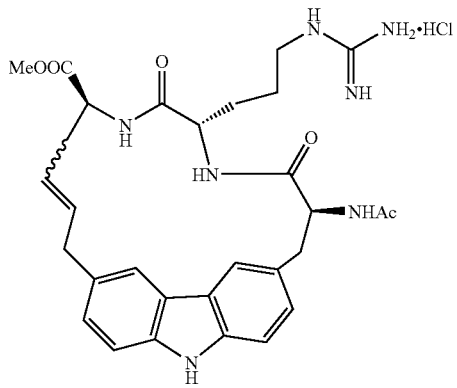

Nomenclature for Carbazole Based Cyclic Peptoids 6-acetamido-8,11-diaza-9-(3-guanidinopropyl)-12-methoxycarbonyl-7,10-dioxo-[12](3,6)-1H-carbazolophane

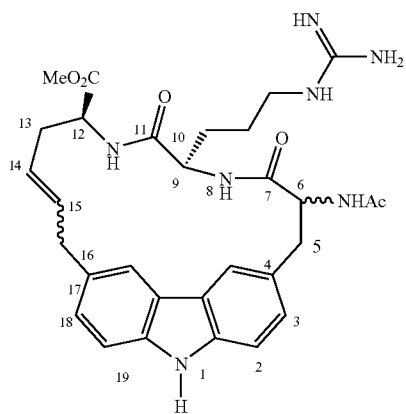

These compounds are named as carbozolophanes with the numbering of the cyclophane structure as shown above. The notation [12] refers to the length of the atom chain attached to the heteroaromatic scaffold and the notation (3,6) refers to where this 12-atom chain is attached to the parent 9H-carbazole unit.

Note: For examples 23–44, where samples exhibited several isomers [diastereoisomers, (E) or (Z) isomers and/or rotamers], the minor form is indicated by an asterisk in their NMR spectra.

Example 23

Preparation of 6-bromo-3-methyl-1,2,3,4-tetrahydrocarbazole

To a solution of 4-methylcyclohexanone (5.47 mL, 44.6 mmol), cyclohexane (70 mL) and glacial acetic acid (50 mL) was added 4-bromophenylhydrazine hydrochloride (10.0 g, 44.6 mmol) and the reaction mixture was refluxed for 23 h under a nitrogen atmosphere. The cooled reaction mixture was filtered and the filtrate was evaporated. Diethyl ether was added and the mixture was washed with a saturated sodium bicarbonate solution and then water; the ether solution was dried and evaporated. The crude product was recrystallised from ethanol over an ice bath, filtered, washed with cold PS and dried in vacuo to afford 6-bromo-3-methyl-1,2,3,4-tetrahydrocarbazole (8.73 g, 33.1 mmol, 74%) as an off-white solid, mp 108–110° C.

$^1$H NMR, 400 MHz, $(D_6)$benzene, δ7.78, d, J=2 Hz, 1H, H-5; 7.41, dd, J=8, 2 Hz, 1H, H-7; 6.77, d, J=8 Hz, 1H, H-8; 6.23, bs, 1H, NH; 2.53, dd, J=15, 5 Hz, 1H, H-4; 2.32–2.15, m, 2H, H-1, H-2; 2.01, dd, J=15, 9 Hz, 1H, H-4; 1.73–1.61, m, 2H, H-2, H-3; 1.29, m, 1H, H-1; 0.99, d, J=7 Hz, 3H, CH$_3$.

Example 24

Preparation of 6-bromo-9-tert-butoxycarbonyl-3-methyl-1,2,3,4-tetrahydrocarbazole A solution of 6-bromo-3-methyl-1,2,3,4-tetrahydrocarbazole obtained from Example 23 (7.0 g, 26.5 mmol) in dry THF (25 mL) was added to sodium hydride (1.17 g, 29.2 mmol) under a nitrogen atmosphere and the mixture was stirred for 0.5 h at room temperature. A solution of di-tert-butyl-dicarbonate (8.67 g, 39.8 mmol) in dry THF (55 mL) was added and the reaction mixture was stirred for 20.5 h. The reaction solvent was evaporated, ether was added and the ether mixture was washed with water, dried and evaporated. The crude product was dissolved in ethanol, the solvent evaporated to a minimal volume and the product recrystallised over an ice bath. The recrystallised solid was filtered, washed with cold MeOH and dried in vacuo to afford 6-bromo-9-tert-butoxycarbonyl-3-methyl-1,2,3,4-tetrahydrocarbazole (8.33 g, 22.9 mmol. 86%) as an off-white solid, mp 122° C.

$^1$H NMR, $(D_6)$benzene, δ8.27, d, J=8.7 Hz, 1H, H-8; 7.61, d, J=2.1 Hz, 1H, H-5; 7.44, dd, J=8.7, 2.1 Hz, 1H, H-7; 3.06–2.94, m, 1H, H-1; 2.85–2.70, m, 1H, H-2; 2.36, dd, J=16, 5 Hz, 1H, H-4; 1.90–1.78, m, 1H, H-4; 1.65, m, 2H, H-2 and H-3; 1.38, s, 9H, C(CH$_3$)$_3$; 1.30–1.16, m, 1H, H-1; 0.96, d, J=6.6 Hz, 3H, CHC$\underline{H}$$_3$.

Example 25

Preparation of 3-bromo-9-tert-butoxycarbonyl-6-methylcarbazole

To a mixture of 6-bromo-9-tert-butoxycarbonyl-3-methyl-1,2,3,4-tetrahydrocarbazole obtained in Example 24 (2.0 g, 5.49 mmol), 2,3-dichloro-4,5-dicyano-1,4-benzoquinone (2.62 g, 11.5 mmol) and activated 3 Å molecular sieves was added anhydrous benzene (17 mL) under a nitrogen atmosphere, and the mixture was refluxed for 20 h. The cooled reaction mixture was filtered and the filtrate evaporated. The crude product was chromatographed (PS with gradient elution up to PS:DCM 3:1) to afford 3-bromo-9-tert-butoxycarbonyl-6-methylcarbazole (1.64 g, 4.56 mmol, 83%) as a colourless solid. By-products were also obtained—6-bromo-9-tert-butoxycarbonyl-4-ethoxy-3-methylcarbazole (12 mg, 0.030 mmol, 0.5%) was obtained as a colourless oil, and 6-bromo-9-tert-butoxycarbonyl-1,2-dihydro-3-methylcarbazol-4-(3H)-one (52 mg, 0.14 mmol, 2.5%) was obtained as a pale yellow solid.

3-bromo-9-tert-butoxycarbonyl-6-methylcarbazole: mp 96° C. Rf: 0.66 in PS:DCM (2:1). $^1$H NMR, δ8.14, d, J=9 Hz, 1H, H-1; 8.10, d, J=8.7 Hz, 1H, H-8; 7.99, d, J=2.1 Hz, 1H, H-4; 7.65, bs, $W_{1/2}$ 4 Hz, 1H, H-5; 7.50, dd, J=8.9, 2 Hz, 1H, H-2; 7.27, dd, J=8.4, 1.8 Hz, 1H, H-7; 2.48, s, 3H, ArCH$_3$; 1.74, s, 9H, C(CH$_3$)$_3$.

6-bromo-9-tert-butoxycarbonyl-4-ethoxy-3-methylcarbazole: Rf: 0.58 in PS:DCM (2:1). $^1$H NMR, δ8.32, d, J=2.1 Hz, 1H, H-4; 8.16, d, J=9 Hz, 1H, H-1; 7.91, d, J=8.4 Hz, 1H, H-8; 7.51, dd, J=8.9, 2 Hz, 1H, H-2; 7.27, d, J=8.7 Hz, 1H, H-7; 4.06, q, J=7.2 Hz, 2H, OC$\underline{H}_2$CH$_3$; 2.40, s, 3H, ArCH$_3$; 1.72, s, 9H, C(CH$_3$)$_3$; 1.55, t, J=7.2 Hz, 3H, OCH$_2$C$\underline{H}_3$. 6-bromo-9-tert-butoxycarbonyl-1,2dihydro-3-methylcarbazol-4-(3H)-one: mp 137° C.

Example 26

Preparation of 3-bromo-6-bromomethyl-9-tert-butoxycarbonylcarbazole

A suspension of 3-bromo-9-tert-butoxycarbonyl-6-methylcarbazole obtained from Example 25 (653 mg, 1.81 mmol) and recrystallised N-bromosuccinimide (355 mg, 2.00 mmol) in carbon tetrachloride was refluxed under nitrogen with irradiation from a 150 W halogen lamp for 2.5 h. The reaction mixture was cooled over an ice bath and filtered, and the filtrate evaporated. The crude product was chromatographed (PS with gradient elution to PS:DCM 1:1) to afford 3-bromo-6-bromomethyl-9-tert-butoxycarbonylcarbazole (551 mg, 1.26 mmol, 69%) as a colourless solid, mp 150° C. (dec).

$^1$H NMR, 400 MHz, δ8.22, d, J=8.4 Hz, 1H, H-8; 8.16, d, J=8.8 Hz, 1H, H-1; 8.07, d, J=2 Hz, 1H, H-4; 7.93, d, J=1.6 Hz, 1H, H-5; 7.54, dd, J=8.8, 2 Hz, 1H, H-2; 7.50, dd, J=8.8, 2 Hz, 1H, H-7; 4.66, s, 2H, CH$_2$; 1.73, s, 9H, CH$_3$.

Example 27

Preparation of diethyl 2-acetamido-2-[3'-(6'-bromo-9'-tert-butoxycarbonyl)-carbazolylmethyl]-propanedioate A solution of diethyl acetamidomalonate (225 mg, 1.04 mmol) in anhydrous DMSO (6 mL) was added to sodium hydride (44 mg, 1.09 mmol) under a nitrogen atmosphere and the mixture was stirred at room temperature for 1.5 h. After this period, 3-bromo-6-bromomethyl-9-tert-butoxycarbonylcarbazole obtained from Example 26 (500 mg, 1.14 mmol) was added and the reaction mixture was stirred at room temperature for 0.5 h. The reaction mixture was diluted with diethyl ether, the ether mixture was washed with brine and water several times. The water layers were extracted with diethyl ether, and the ether extracts were washed with water. Both ether solutions were combined, dried and evaporated to afford diethyl 2-acetamido-2-[3'-(6'-bromo-9'-tert-butoxycarbonyl)-carbazolylmethyl]-propanedioate (448 mg, 0.78 mmol, 75%) as a yellow solid, mp 158° C.

$^1$H NMR, 400 MHz, δ8.14, d, J=8 Hz, 2H, H-1' and H-8' (direct overlap); 7.95, d, J=1.6 Hz, 1H, H-5'; 7.54, d, J=2 Hz, 1H, H-4'; 7.53, dd, J=8.8, 2 Hz, 1H, H-7'; 7.10, dd, J=8.6, 2 Hz, 1H, H-2'; 6.53, s, 1H, NH; 4.28, q, J=7.2 Hz, 4H, OC$\underline{H}_2$CH$_3$; 3.79, s, 2H, ArCH$_2$; 2.05, s, 3H, COCH3; 1.72, s, 9H, C(CH$_3$)$_3$; 1.31, t, J=7.2 Hz, 6H, OCH$_2$C$\underline{H}_3$.

Example 28

Preparation of ethyl 2-acetamido-3-[3'-(6'-bromocarbazole)]propanoate

A suspension of diethyl 2-acetamido-2-[3'-(6'-bromo-9'-tert-butoxycarbonyl)-carbazylmethyl]-propanedioate obtained from Example 27 (310 mg, 0.54 mmol), lithium chloride (23 mg, 0.54 mmol), distilled water (0.02 mL, 1.08 mmol) and DMSO (5 mL) was refluxed under a nitrogen atmosphere for 2 h. The cooled reaction mixture was diluted with ether, the ether mixture was washed with brine and then water. The ether layer was dried and evaporated to afford ethyl 2-acetamido-3-[3'-(6'-bromocarbazole)]propanoate (181 mg, 0.45 mmol, 83%) as a yellow solid, mp 175° C.

$^1$H NMR, δ8.49,s, 1H, NH; 8.05, d, J=1.8 Hz, 1H, H-5'; 7.69, s, $W_{1/2}$ 4 Hz, 1H, H-4'; 7.43, dd, J=8.6, 1.8 Hz, 1H, H-7'; 7.25, d, J=9 Hz, 1H, H-1'; 7.23, d, J=8.4 Hz, 1H, H-8'; 7.12, dd, J=8.3, 1.5 Hz, 1H, H-2'; 6.05, d, J=7.5 Hz, 1H, NH; 4.90, dt, J=7.8, 6 Hz, 1H, CHN; 4.16, q, J=7.2 Hz, 2H, OC$\underline{H}_2$CH$_3$; 3.27, dd, J=14.1, 6.3 Hz, 1H, ArCH$_2$; 3.20, dd, J=14, 5.9 Hz, 1H, ArCH$_2$; 1.96, s, 3H, COCH$_3$; 1.22, t, J=7.2 Hz, 3H, OCH$_2$C$\underline{H}_3$.

Example 29

Alternative One-Pot Preparation of ethyl 2-acetamido-3-[3'-(6'-bromocarbazole)]propanoate A solution of diethyl acetamidomalonate (368 mg, 1.70 mmol) in anhydrous DMSO (10 mL) was added to sodium hydride (71 mg, 1.78 mmol) under a nitrogen atmosphere and the mixture was stirred at room temperature for 1.5 h. After this period, 3-bromo-6-bromomethyl-9-tert-butoxycarbonylcarbazole obtained in Example 26 (820 mg, 1.87 mmol) was added and the reaction mixture was stirred at room temperature for 0.5 h. Lithium chloride (71 mg, 1.70 mmol) and distilled water (0.06 mL, 3.40 mmol) were added and the reaction mixture was refluxed for 1.75 h. The reaction mixture was diluted with ether, the ether mixture was washed with brine and then water, the combined water layers were extracted with ether, and these extracts were washed with wafer. The combined ether layers were dried and evaporated and the crude product was chromatographed (PS with gradient elution to DCM and finally EtOAc) to afford ethyl 2-acetamido (6'-bromo-9'-ethyl)-3-carbazolepropanoate (56 mg, 0.13 mmol, 8%) as a dark yellow oil, and ethyl 2-acetamido-3-[3'-(6'-bromocarbazole)]propanoate (481 mg, 1.19 mmol, 70%) as a pale yellow solid.

Ethyl 2-acetamido-3-[3'-(6'-bromo-9'-ethylcarbazole)] propanoate: $^1$H NMR, δ8.11, d, J=1.8 Hz, 1H, H-5'; 7.73, s, $W_{1/2}$ 4.7 Hz, 1H, H-4'; 7.51, dd, J=8.5, 2 Hz, 1H, H-7'; 7.30, d, J=8.4 Hz, 1H, H-1'; 7.24, d, J=8.4 Hz, 1H, H-8'; 7.20, dd, J=8.4, 1.8 Hz, 1H, H-2'; 5.98, d, J=7.5 Hz, 1H, NH. 4.91, dt, J=7.8, 6 Hz, 1H, CHN; 4.29, q, J=7.2 Hz, 2H, NC$\underline{H}_2$CH$_3$; 4.18, q, J=7.2 Hz, 2H, OC$\underline{H}_2$CH$_3$; 3.27, d, J=5.7 Hz, 2H, ArCH$_2$; 1.98, s, 3H, COCH$_3$; 1.38, t, J=7.2 Hz, 3H, NCH$_2$CH$_3$; 1.24, t, J=7.2 Hz, 3H, OCH$_2$CH$_3$.

Example 30

Preparation of ethyl 2-acetamido-3-[3'-(6'-allylcarbazole)]propanoate

To a glass, high-pressure tube containing ethyl 2-acetamido-(6'-bromo)-3-carbazolepropanoate obtained in Examples 28 or 29 (1.0 g, 2.48 mmol), palladium chloride (22 mg, 0.124 mmol) and triphenylphosphine (130 mg, 0.496 mmol) was added anhydrous DMF (10 mL) followed by allyltributyltin (0.92 mL, 2.98 mmol). The tube was sealed under nitrogen and the reaction mixture heated in a 110° C. oil bath for 22 h. The cooled reaction mixture was diluted with diethyl ether, the ether mixture was washed with brine and then water, and the ether layer was dried and evaporated. The crude product was chromatographed (PS with gradient elution to DCM:EtOAc 2:1) to afford ethyl 2-acetamido-3-[3'-(6'-allylcarbazole)]propanoate (823 mg, 2.26 mmol, 91%) as a pale yellow solid, mp 100° C.

$^1$H NMR, δ8.13, bs, 1H, ArNH; 7.80, s, W$_{1/2}$ 4.8 Hz, 1H, H-5'; 7.76, s, W$_{1/2}$ 4.8 Hz, 1H, H-4'; 7.32, d, J=8.7 Hz, 1H, H-8'; 7.29, d, J=8.4 Hz, 1H, H-1'; 7.22, dd, J=8.7, 1.2 Hz, 1H, H-7'; 7.10, dd, J=8.4, 1.5 Hz, 1H, H-2'; 6.05, ddt, J=17, 10, 6.6 Hz, 1H, CH$_2$CH=CH$_2$; 5.96, d, J=8.4 Hz, 1H, NHAc; 5.11, dd, J=15, 1.8 Hz, 1H, CH$_2$CH=CH$_2$; 5.08, d, J=8.1 Hz, 1H, CH$_2$CH=CH$_2$; 4.90, dt, J=7.8, 6.3 Hz, 1H, CHN; 4.17, q, J=7.2 Hz, 2H, OCH$_2$CH$_3$; 3.54, d, J=6.6 Hz, 2H, CH$_2$CH=CH$_2$; 3.26, d, J=5.7 Hz, 2H, ArCH$_2$; 1.97, s, 3H, COCH$_3$; 1.23, t, J=7.2 Hz, 3H, OCH$_2$CH$_3$.

Example 31

Preparation of ethyl 2-acetamido-3-[3'-(6'-allyl-9'-tert-butoxycarbonylcarbazole)]propanoate A suspension of ethyl 2-acetamido-3-[3'-(6'-allylcarbazole)]propanoate obtained in Example 30 (823 mg, 2.26 mmol) and cesium carbonate (1.47 g, 4.52 mmol) in anhydrous DMF (20 mL) was stirred at room temperature under a nitrogen atmosphere for 15 min before a solution of di-tert-butyl-dicarbonate (739 mg, 3.39 mmol) in anhydrous DMF (6 mL) was added. The reaction mixture was stirred at room temperature for 20 h. After this period the reaction mixture was diluted with ether, and the ether mixture was washed with brine followed by water, and then dried and evaporated. The crude product was chromatographed (PS with gradient elution to DCM:EtOAc 5:1) to afford ethyl 2-acetamido-3-[3'-(6'-allyl-9'-tert-butoxycarbonylcarbazole)]propanoate (820 mg, 1.77 mmol, 78%) as a pale yellow solid, mp 125° C.

$^1$H NMR, δ8.18, d, J=8.1 Hz, 1H, H-8'; 8.16, d, J=8.1 Hz, 1H, H-1'; 7.71, d, J=1.2 Hz, 1H, H-4'; 7.68, d, J=1.5 Hz, 1H, H-5'; 7.27, dd, J=8.5, 1.5 Hz, 1H, H-2'; 7.17, dd, J=8.5, 1.8 Hz, 1H, H-7'; 6.03, ddt, J=16.5, 9.9, 6.9 Hz, 1H, CH$_2$CH=CH$_2$; 5.11, dd, J=17.7, 1.8 Hz, 1H, CH$_2$CH=CH$_2$; 5.10, dd, J=10.2, 1.8 Hz, 1H, CH$_2$CH=CH$_2$; 4.90, dt, J=7.5, 6 Hz, 1H, CHN; 4.17, q, J=7.2 Hz, 2H, OCH$_2$CH$_3$; 3.52, d, J=6.6 Hz, 2H, CH$_2$CH=CH$_2$; 3.28, dd, J=14, 5.7 Hz, 1H, ArCH$_2$; 3.22, dd, J=14.1, 5.7 Hz, 1H, ArCH$_2$; 1.98, s, 3H, COCH$_3$; 1.72, s, 9H, C(CH$_3$)$_3$; 1.23, t, J=7.2 Hz, 3H, OCH$_2$CH$_3$.

Example 32

Preparation of 2-acetamido-3-[3'-[6'-allyl-9'-tert-butoxycarbonylcarbazole)]propanoic acid To an ice-cold solution of ethyl 2-acetamido-3-[3'-(6'-allyl-9'-tert-butoxycarbonylcarbazole)]propanoate obtained in Example 31 (787 mg, 1.70 mmol) in THF (50 mL) was added a solution of lithium hydroxide (440 mg, 10.5 mmol) in distilled water (20 mL), and the reaction mixture was stirred at 0° C. for 3.5 h. After this period the THF portion of the solvent was evaporated, the aqueous mixture remaining was diluted with distilled water and washed with ether. The aqueous layer was acidified to pH<2 with a 10% HCl solution and the product was extracted with diethyl ether, after adding a sufficient amount of solid sodium chloride to the acidified mixture to dissolve it. Finally, the ether extracts were dried and evaporated to afford 2-acetamido-3-[3'-(6'-allyl-9'-tert-butoxycarbonylcarbazole)]propanoic acid (666 mg, 1.53 mmol, 90%) as a colourless solid, mp 177° C.

$^1$H NMR, (D$_6$)acetone, δ8.21, d, J=8.4 Hz, 1H, H-8'; 8.20, d, J=8.7 Hz, 1H, H-1'; 7.96, d, J=1.2 Hz, 1H, H-4'; 7.89, d, J=0.9 Hz, 1H, H-5'; 7.39, dd, J=8.4, 1.5 Hz, 2H, H-2' and NH (concealed under ArH signal); 7.33, dd, J=8.5, 1.8 Hz, 1H, H-7'; 6.07, ddt, J=16.9, 9.9, 6.9 Hz, 1H, CH$_2$CH=CH$_2$; 5.14, dd, J=17.2, 1.5 Hz, 1H, CH$_2$CH=CH$_2$; 5.07, dd, J=9.9, 1.5 Hz, 1H, CH$_2$CH=CH$_2$; 4.80, m, 1H, CHN; 3.55, d, J=6.9 Hz, 2H, CH$_2$CH=CH$_2$; 3.34, dd, J=13.8, 5.4 Hz, 1H, ArCH$_2$; 3.15, dd, J=13.8, 8.1 Hz, 1H, ArCH$_2$; 1.89, s, 3H, COCH$_3$; 1.76, s, 9H, C(CH$_3$)$_3$.

Example 33

Preparation of a Carbazole Peptoid Derivative

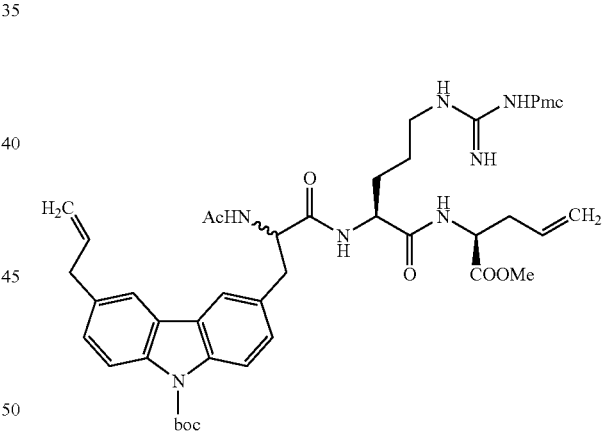

To a mixture of 2-acetamido-3-[3'-(6'-allyl-9'-tert-butoxycarbonylcarbazole)]propanoic acid (84 mg, 0.192 mmol), methyl L-arg(Pmc)allylglycinate (106 mg, 0.192 mmol) and 4-dimethylaminopyridine (1 crystal) was added dry DCM (3 mL) and anhydrous acetonitrile (5 mL). The mixture was warmed and stirred vigorously under nitrogen to give a translucent solution before 1-[3-(dimethylamino)propyl]-3-ethylcarbodiimide hydrochloride (37 mg, 0.192 mmol) was added. The reaction mixture was stirred at room temperature under nitrogen for 19.5 h. After this period the reaction solvent was evaporated, DCM was added and the mixture was washed with brine followed by water. The DCM layer was dried and evaporated and then chromatographed (PS with gradient elution to DCM:MeOH 10:1). The purified product was triturated with PS from DCM to give the carbazole peptoid derivative as a cream solid, mp 141–143° C. Rf: 0.60 in 10% MeOH in DCM.

$^1$H NMR, δ8.12, d, J=8.4 Hz, 1H, ArH; 8.10, d, J=8.4 Hz, 1H, ArH; 7.78, s, W$_{1/2}$ 6 Hz, 1H, ArH; 7.66, s, W$_{1/2}$ 4 Hz, 1H, ArH; 7.59, d, J=7.5 Hz, 1H, NH; 7.29–7.19, m, 2H, ArH; 6.93, d, J=6.9 Hz, 1H, NH; 6.76, d, J=7.2 Hz, 1H, NH; 6.33, bs, 1H, NH; 6.26, bs, 1H, NH; 5.97, m, 1H, ArCH$_2$CH=CH$_2$; 5.63, m, 1H, CH$_2$CH=CH$_2$; 5.14–4.95, m, 4H, CH$_2$CH=CH$_2$; 4.80, m, 1H, CHN; 4.71, dt, J=7.2, 7.2 Hz, 1H, CHN; 4.56–4.40, m, 2H, NH and CHN; 3.62, s, 3H, OCH$_3$; 3.46, d, J=8.1 Hz, 1H, ArCH$_2$CH=CH$_2$; 3.43, d, J=7.2 Hz, 1H, ArCH$_2$CH=CH$_2$; 3.32–2.94, m, 6H, NHCH$_2$CH$_2$CH$_2$ and ArCH$_2$; 2.54, s, 3H, ArCH$_3$ (ortho to SO$_2$ attach); 2.51, s, 3H, ArCH$_3$ (ortho to SO$_2$ attach); 2.44, m, 4H, CH$_2$CH=CH$_2$ and ArCH$_2$CH$_2$; 2.06, s, 3H, ArCH$_3$; 1.90, s, 3H, COCH$_3$; 1.74, t, J=6.3 Hz, 2H, ArCH$_2$CH$_2$; 1.68, s, 9H, C(CH$_3$)$_3$; 1.58, m, 2H, NHCH$_2$CH$_2$CH$_2$, 1.26, s, 6H, C(CH$_3$)$_2$.

Example 34

Preparation of Protected Cyclised Carbazole Peptoid Product

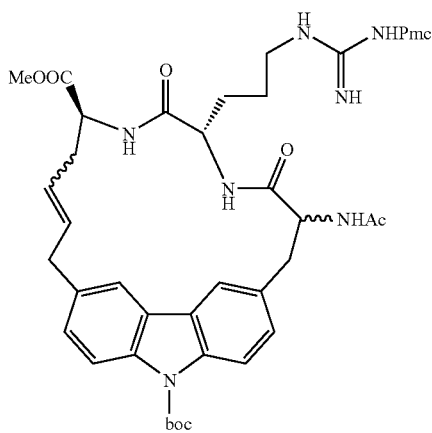

To a solution of the compound obtained in Example 33 (110 mg, 0.113 mmol) in dry DCM (28 mL) was added Grubbs' ruthenium catalyst (9 mg, 0.0113 mmol) and the reaction mixture was refluxed under a nitrogen atmosphere for 23 h. After this period the reaction solvent was evaporated, and the crude product was chromatographed (PS with gradient elution to DCM:MeOH 10:1) and then triturated with diethyl ether/PS from DCM to give a cyclised carbazole peptoid derivative (107 mg, 0.113 mmol, 100%) as a cream solid, mp 190° C. (dec). Rf: 0.37 in 10% MeOH in DCM. Mass spectrum (ES$^+$), m/z 942 (30%) [MH$^+$].

Example 35

Preparation of 6-acetamido-8,11-diaza-14-ene-9-(3-guanidinopropyl)-12-methoxycarbonyl-7,10-dioxo-[12](3,6)-1H-carbazolophane HCl

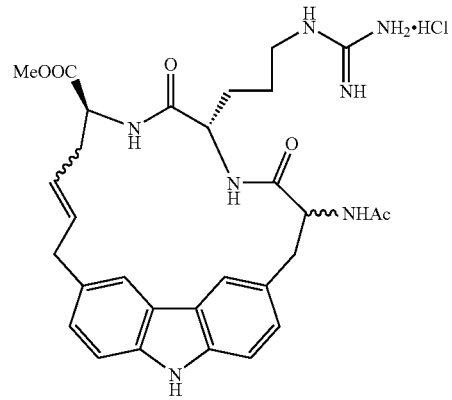

A solution of the cyclic carbazole derivative obtained in Example 34 (20 mg, 0.0212 mmol) in TFA (2 mL) was stirred at room temperature under a nitrogen atmosphere for 1.5 h. The TFA was removed by co-evaporation with several portions of DCM. The crude product was dissolved in MeOH, a 1M HCl-in-ether solution (0.04 mL, 0.0425 mmol) was added and the reaction mixture was stirred for 15 min. After this period the solvent was evaporated to a minimal volume and the product recrystallised from ether/PS over an ice bath to give 6-acetamido-8,11-diaza-14-ene-9-(3-guanidinopropyl)-12-methoxycarbonyl-7,10-dioxo-[12](3,6)-1H-carbazolophane HCl (12 mg, 0.0196 mmol, 92%) as a pale brown solid, mp 222–224° C. (dec). Mass spectrum (ES$^+$), m/z 576 (100%) [MH$^+$]. HRMS calcd for C$_{30}$H$_{37}$N$_7$O$_5$+H: 576.2934. found: 576.2902.

Example 36

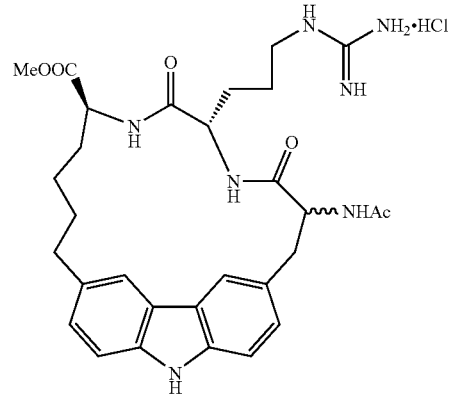

6-Acetamido-8,11-diaza-9-(3-guanidinopropyl)-12-methoxycarbonyl-7,10-dioxo-[12](3,6)-1H-carbazolophane HCl (9S,12S) was prepared by hydrogenation of the compound of Example 35.

Example 37

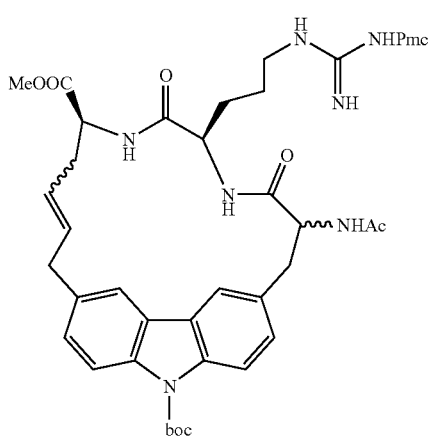

6-Acetamido-8,11-diaza-14-ene-9-(3-guanidinopropyl)-12-methoxycarbonyl-7,10-dioxo-[12](3,6)-1H-carbazolo-phane HCl (9R,12S) was prepared according to the procedure for Example 35 except the precursor containing a D-arginyl residue was used.

Example 38

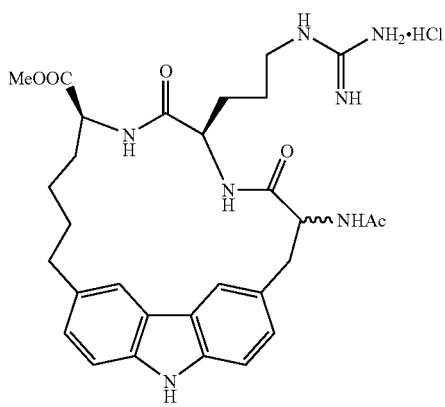

6-Acetamido-8,11-diaza-9-(3-guanidinopropyl)-12-methoxycarbonyl-7,10-dioxo-[12](3,6)-1H-carbazolophane HCl (9R,12S) was prepared by hydrogenation of the compound of Example 37.

Example 39

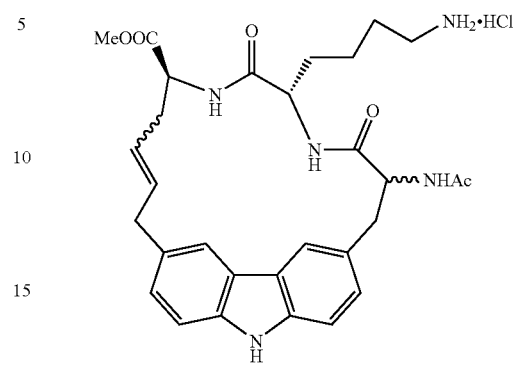

6-Acetamido-9-(4-aminobutyl)-8,11-diaza-14-ene-12-methoxycarbonyl-7,10-dioxo-[12](3,6)-1H-carbazolophane HCl (9S,12S) was prepared similarly to Example 35 from the corresponding protected Fmoc-Lys-Pmb protected carbozole derivative with the initial deprotection using anisole/TFA followed by piperidine

Example 39A

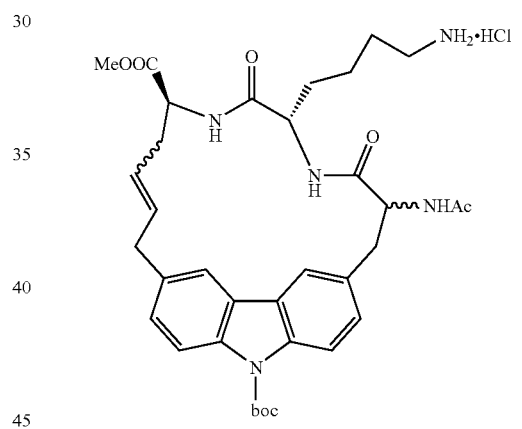

6-Acetamido-9-(4-aminobutyl)-8,11-diaza-1-tert-butoxycarbonyl-14-ene-12-methoxycarbonyl-7,10-dioxo-[12](3,6)-1H-carbazolophane HCl (9S,12S) was prepared similarly to Example 39 but deprotection of the lysine side chain was conducted using piperidine in dry THF at room temperature. The free base was converted to its hydrochloride salt using HCl in ether with the compound isolated as a cream solid, mp ca 230° C. (dec). $^1$H NMR, [500 MHz, (CD$_3$)$_2$SO] δ 8.84*, br d, J 7.5 Hz, NH-11; 8.82*, br d, J 8.0 Hz, NH-11; 8.70, br d, J 7.5 Hz, NH-11; 8.63, br d, J 7.5 Hz, NH-11; 8.49*, br d, J 10.0 Hz, NH-8; 8.47, br d, J 9.5 Hz, NHAc; 8.41*, br d, J 8.5 Hz, NH-8; 8.38–8.28, m, NHAc; 8.24–8.16*, m, NH-11; 8.14–7.93, m, 2H, ArH-2 and ArH-19; 8.04, br s, NH$_2$; 7.97*, br s, NH$_2$; 7.83–7.77*, m, NH-8; 7.69, br d, J 8.0 Hz, NH-8; 7.57*, s, ArH-21; 7.55, s, ArH-20; 7.53, s, ArH-20; 7.50*, s, ArH-20; 7.49*, br d, J 8.5 Hz, NHAc; 7.41, s, ArH-21; 7.38–7.30*, m, ArH-3; 7.30, br d, J 8.0 Hz, ArH-18; 7.22, br d, J 6.5 Hz, NHAc; 7.16*, br d, J 8.0 Hz, ArH-3; 7.10, br d, J 8.0 Hz, ArH-3; 5.89–5.79, m, ArCH$_2$CH=CH (E isomer); 5.81–5.70, m, ArCH$_2$CH=CH* (Z isomer) and CHCH$_2$CH=CH; 5.72–5.62, m, CHCH₂CH=CH; 5.65–5.42, m, CHCH₂CH=CH; 4.84*, br s, NCH-6; 4.62*, br d, J 3.5 Hz, NCH-6 and NCH-9; 4.46, br d, J 3.5 Hz, NCH-9 and NCH-12; 4.31*, br d, J 8.0 Hz, NCH-12; 4.28*, br d, J 7.5 Hz, NCH-12; 4.18, br s, NCH-6; 3.72–3.36, m, ArCH₂CH=CH; 3.65, s, OCH₃; 3.60*, s, OCH₃; 3.57*, s, OCH₃; 3.22, –2.84, m, 2H, ArCH₂-5; 2.78–2.50, m, 2H, NCH₂(CH₂)₃; 2.59, br d, J 11.0 Hz, CHC H₂CH=CH; 2.42–2.28, m, CHCH₂CH=CH; 2.33, br d, J 11.0 Hz, CHCH₂CH=CH; 1.90, s, COCH₃; 1.87, s, COCH₃; 1.84–1.45, m, 2H, N(CH₂)₃CH₂; 1.77*, s, COCH₃; 1.73*, s, COCH₃; 1.67, s, 9H, C(CH₃)₃; 1.62–1.40, m, 2H, NCH₂CH₂(CH₂)₂; 1.32, m, N(CH₂)₂CH₂CH₂; 1.21, m, N(CH₂)₂CH₂CH₂.

Example 40

6-Acetamido-9-(4-aminobutyl)-8,11-diaza-12-methoxycarbonyl-7,10-dioxo-[12](3,6)-1H-carbazolophane HCl (9S, 12S) was prepared by hydrogenation of the compound of Example 39.

Example 41

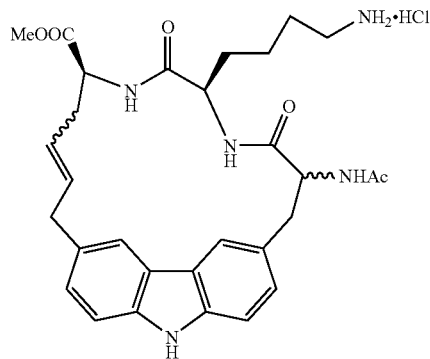

6-Acetamido-9-(4-aminobutyl)-8,11-diaza-14-ene-12-methoxycarbonyl-7,10-dioxo-[12](3,6)-1H-carbazolophane HCl (9R,12S) was prepared in the same manner as Example 39 except that an amino acyl moiety containing a protected D-lysine residue was utilised.

Example 42

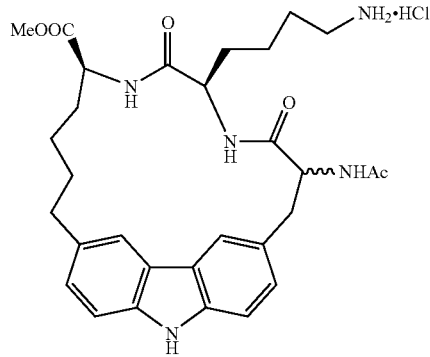

6-Acetamido-9-(4-aminobutyl)-8,11-diaza-12-methoxycarbonyl-7,10-dioxo-[12](3,6)-1H-carbazolophane HCl (9R,12S) was prepared by hydrogenation of the compound of Example 41

Example 43

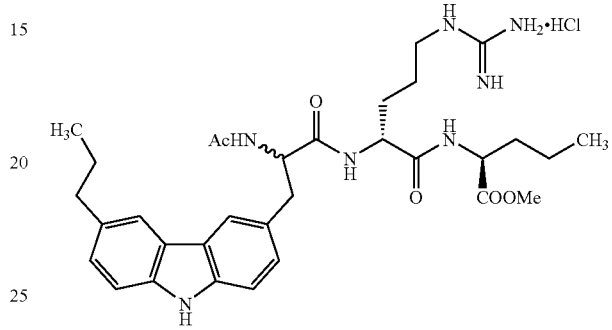

Methyl 8-acetamido-3,6-diaza-5-[3-guanidinopropyl]-4,7-dioxo-2-propyl-9-[3-(6-propyl)-9H-carbazole]nonanoate HCl (2S,5R) was prepared by hydrogenation and deprotection of the ring opened diene precursor of Example 37.

Hydrogenation of the compound obtained in Example 33 gave the corresponding compound where the allyl groups had been reduced to propyl groups. This was deprotected according to the procedure of Example 35 to provide a cream solid, mp 210° C.

¹H NMR, [500 MHz, (CD₃)₂SO, isomer ratio 69:31] δ 11.16*, br s, 0.3H, ArNH; 10.99, br s, 0.7H, ArNH; 8.33, br d, J 8.0 Hz, 0.7H, NH-6; 8.30, br d, J 6.5 Hz, 0.7H NHAc; 8.25*, br d, J 7.5 Hz, 0.3H, NH-3; 8.21–8.11*, m, 0.6H, NH-6 and NHAc; 8.07, br d, J 7.5 Hz, 0.7H, NH-3; 7.94, s, 1H, ArCH-4; 7.81, s, 1H, ArCH-5; 7.62–7.53*, m, 0.3H, N HCH₂; 7.45, br s, 0.7 NHCH₂; 7.35, m, 2H, ArH-1 and ArH-8; 7.26, d, J 8.5 Hz, 1H, ArH-2; 7.17, d, J 8.0 Hz, 1H, ArH-7; 6.85, v br s, 3H, NH(C=NH)NH₂; 4.56, m, 1H, NCH-8; 4.37*, dt, J 6.0, 7.5 Hz, 0.3H, NCH-5; 4.30–4.16, m, 1.7H, NCH-2 and NCH-5; 3.61, s, 3H, OCH₃; 3.20–3.11*, m, 0.3H, ArCHH-9; 3.15–3.05*, m, 0.6H, NC H₂(CH₂)₂; 3.11–3.03, m, 0.7H, ArCHH-9; 2.98–2.88, m, 0.7H, ArCHH-9; 2.93–2.83, m, 1.4H, NCH₂(CH₂)₂; 2.88–2.82*, m, 0.3H, ArCHH-9; 2.69, t, J 7.5 Hz, 2H, ArC H₂CH₂CH₃; 1.77, s, 2.1H, COCH₃; 1.75*, s, 0.9H, COCH₃; 1.68–1.54, m, 2H, CHCH₂CH₂CH₃; 1.67–1.58*, m, 0.6H, C(CH₂)₂CH₂; 1.65, m, 2H, ArCH₂CH₂CH₃; 1.52–1.38*, m, 0.6H, NCH₂CH₂CH₂; 1.48–1.36, m, 1.4H, N(CH₂)₂CH₂; 1.34–1.17, m, 2H, CHCH₂CH₂CH₃; 1.25–1.13, m, 1.4H, NCH₂CH₂CH₃; 0.91, t, J 7.0 Hz, 3H, Ar(CH₂)₂CH₃; 0.83, t, J 7.0 Hz, 3H, CH(CH₂)₂CH₃.

Example 44

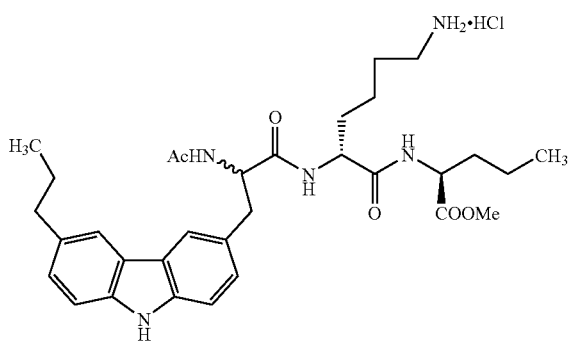

Methyl 8-acetamido-5-[4-aminobutyl]-3,6-diaza-4,7-dioxo-2-propyl-9-[3-(6-propyl)-9H-carbazole]nonanoate HCl (2S,5R) was prepared by hydrogenation and deprotection of the ring opened diene precursor of Example 41.

The uncyclised protected precursor to Example 41, was reduced by hydrogenation and then deprotected in the usual manner to yield a cream solid, mp 160–162° C.

$^1$H NMR, [500 MHz, $(CD_3)_2SO$, isomer ratio 69:31] δ 11.16, br s, 0.7H, ArNH; 11.07*, br s, 0.3H, ArNH; 8.36, br d, J 6.5 Hz, 0.7H, NHAc; 8.32, br d, J 8.0 Hz, 0.7H, NH-6; 8.29*, br d, J 7.5 Hz, 0.3H, NH-3; 8.21*, br d, J 8.0 Hz, 0.3H, NHAc; 8.21*, br d, J 8.5 Hz, 0.3H, NH-6; 8.06*, br s, 0.6H, NH$_2$; 8.02, br d, J 8.0 Hz, 0.7H, NH-3; 7.99, br s, 1.4H, NH$_2$; 7.96*, s, 0.3H, ArH-4; 7.93, s, 0.7H, ArH-4; 7.81, s, 0.7H, ArH-5; 7.79*, s, 0.3H, ArH-5; 7.37*, d, J 8.0 Hz, 0.3H, ArH-8; 7.35, d, J 8.5 Hz, 1.4H, ArH-1 and ArH-8; 7.32*, d, J 8.5 Hz, 0.3H, ArH-1; 7.27*, d, J 8.5 Hz, 0.3H, ArH-2; 7.25, d, J 8.5 Hz, 0.7H, ArH-2; 7.17, d, J 8.0 Hz, 1H, ArCH-7; 4.57*, m, 0.3H, NCH-8; 4.53, dt, J 7.0, 7.5 Hz, 0.7H, NCH-8; 4.34*, dt, J 5.5, 8.0 Hz, 0.3H, NCH-5; 4.22, m, 1H, NCH-2; 4.09, m, 0.7H, NCH-5; 3.60, s, 3H, OCH$_3$; 3.18*, dd, J 13.5, 4.0 Hz, 0.3H, ArCHH-9; 3.05, dd, J 13.2, 7.5 Hz, 0.7H, ArCHH-9; 2.96, dd, J 13.2, 8.5 Hz, 0.7H, ArCHH-9; 2.89*, dd, J 13.2, 10.5 Hz, 0.3H, ArCHH-9; 2.73*, br d, J 5.5 Hz, 0.6H, NCH$_2$(CH$_2$)$_3$; 2.68, t, J 7.5 Hz, 2H, ArCH$_2$CH$_2$CH$_3$; 2.45, br s, 1.4H, NCH$_2$(CH$_2$)$_3$; 1.79, s, 2.1H, COCH$_3$; 1.76*, s, 0.9H, COCH$_3$; 1.71–1.51, m, 2.6H, CHCH$_2$CH$_2$CH$_3$ and N(CH$_2$)$_3$CH$_2$*; 1.69–1.58, m, 2H, ArCH$_2$CH$_2$CH$_3$; 1.61–1.52*, m, 0.6H, NCH$_2$CH$_2$(CH$_2$)$_2$; 1.61–1.48, m, 0.7H, N(CH$_2$)$_3$CH$_2$; 1.41–1.26, m, 2.7H, N(CH$_2$)$_3$CH$_2$, NCH$_2$CH$_2$(CH$_2$)$_2$ and N(CH$_2$)$_2$CH$_2$CH$_2$*; 1.32–1.18, m, 2H, CHCH$_2$CH$_2$CH$_3$; 0.91, t, J 7.0 Hz, 3H, Ar(CH$_2$)$_2$CH$_3$; 0.90–0.82, m, 1.4H, N(CH$_2$)$_2$CH$_2$CH$_2$; 0.82, t, J 7.0 Hz, 2.1H, CH(CH$_2$)$_2$CH$_3$; 0.81*, t, J 7.0 Hz, 0.9H, CH(CH$_2$)$_2$CH$_3$.

Compounds Based on a 1,4-Substituted Phenyl Nucleus

General Synthetic Procedures

N-Boc & Pmc Deprotection (Procedure A)

The N-Boc or Pmc protected amine (1 equiv.) was stirred for 3 hours in 1:1 DCM/TFA solution at room temperature. The solvent was removed under reduced pressure, and the residue was resuspended in a minimal volume of methanol. The solution was then treated with an excess of 1M HCl/ether solution and the solvent again evaporated. The crude product was purified by recrystallization/precipitation from DCM &/or MeOH by addition of ether.

Peptide Coupling (Procedure B)

To a solution of the acid (1 equiv.) in DMF at room temperature was added HOBt (1.1 equiv.), EDCI (1 equiv.) and the amine (1.2 equiv.). If the amine was a hydrochloride salt, DIPEA (1 equiv.) was also added. The mixture was allowed to stir for 16 hours before the reaction was quenched with water until precipitation occurred. The solid was collected by vacuum filtration, and washed thoroughly with water. The amorphous product was dried over P$_2$O$_5$ to yield the desired peptide.

N-Fmoc Deprotection (Procedure C)

The Fmoc Protected amine (1 equiv.) was stirred in 1% piperidine/acetonitrile for 3 hours at room temperature. The solvent was removed under reduced pressure and the crude product was purified by flash column chromatography (15:1, DCM/MeOH) to yield the free amine.

Macrocyclization by Olefin Metathesis (Procedure D)

To a solution of the precursor tripeptide (1 equiv.) in DCM (to 0.004 M) was added Grubb's ruthenium catalyst (15 mol %) and the resulting solution was heated at reflux for 48 hours before the solvent was removed by evaporation and the product isolated by flash column chromatography (15:1, DCM/MeOH) to yield the corresponding macrocycle.

Example 45

Methyl (2S)-2{(1S)-1-[(1S)-2-(4-allyloxyphenyl)-1-methylcarboxamidoethylcarboxamido]-5-tert-butoxycarboxamidopentylcarboxamido}-4-pentenoate

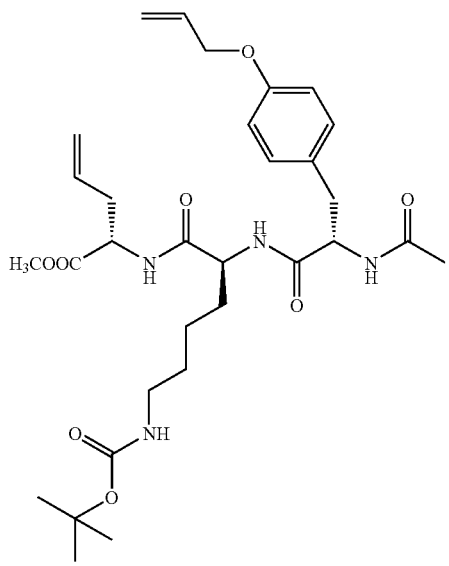

To a solution of methyl (2S)-2-[(1S)-1-amino-5-tert-butoxycarboxamido]-4-pentenoate (782 mg, 2.19 mmol) and (2S)-3-(4-allyloxyphenyl)-2-methylcarboxamidopropanoic acid (576 mg, 2.19 mmol) in DCM (10 mL) was added EDCI (420 mg, 2.19 mmol) and a catalytic quantity of DMAP. The resulting mixture was allowed to stir at room temperature for 16 hours before the reaction was quenched by the addition of DCM (25 mL). The organic layer was washed with brine (2×25 mL) and water (2×25 mL) and dried over MgSO$_4$, before being concentrated by evaporation. The crude product was purified by flash column chromatography (25:1 DCM/MeOH) to afford methyl (2S)-2{(1S)-1-[(1S)-2-(4-allyloxyphenyl)-1-methylcarboxamidoethylcarboxamido]-5-tert-butoxycarboxamidopentylcarboxamido}-4-pentenoate (664 mg, 1.10 mmol, 50%) as a white solid. Mass Spectrum (ES, +ve) m/z 503.4 (100%) [MH$^+$ (less t-boc)], 603.4 (35%) [MH$^+$]. HRMS calcd for $C_{31}H_{47}N_4O_8$ 603.3394. found 603.3397.

Example 46

(5S)-5-[(1S)-2-(4-Allyloxyphenyl)-1-methylcarboxamidoethylcarboxamido]-5-[(1S)-1-methyloxycarbonyl-3-butenylcarbamoyl]pentylammonium chloride

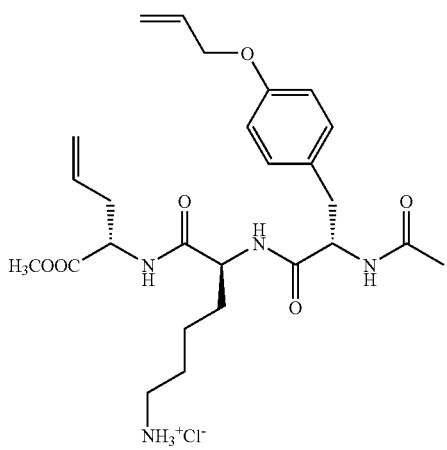

This ammonium salt was synthesized using the general N-Boc deprotection procedure (Procedure A), from methyl (2S)-2{(1S)-1-[(1S)-2-(4-allyloxyphenyl)-1-methylcarboxamidoethylcarboxamido]-5-tert-butoxycarboxamidopentylcarboxamido}-4-pentenoate (104 mg, 0.170 mmol) to yield (5S)-5-[(1S)-2-(4-allyloxyphenyl)-1-methylcarboxamidoethylcarboxamido]-5-[(1S)-1-methyloxycarbonyl-3-butenylcarbamoyl]pentylammonium chloride (55 mg, 0.10 mmol, 60%) as a yellow solid. Mass Spectrum (ES, +ve) m/z 503.3 (100%) [M$^+$ less Cl$^-$]. HRMS calcd for $C_{26}H_{39}N_4O_6$ 503.2870. found 503.2894.

Example 47

Methyl (7S,13S,10S)-10-(4-tert-butoxycarboxamidobutyl)-13-methylcarboxamido-9,12-dioxo-2-oxa-8,11-diazabicyclo[13.2.2]nonadeca-1(17),4,15,18-tetraene-7-carboxylate

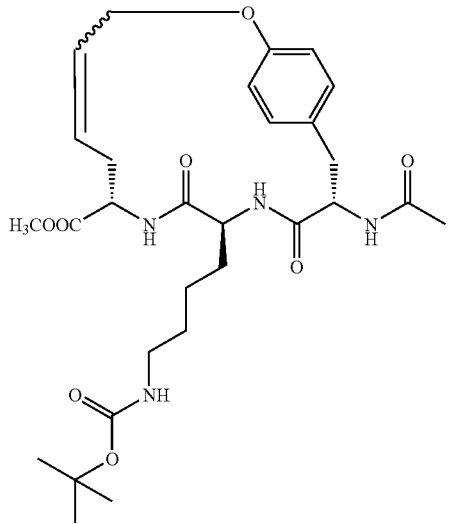

The macrocyclic peptide was prepared using the general procedure for olefin metathesis (Procedure D) using methyl (2S)-2{(1S)-1-[(1S)-2-(4-allyloxyphenyl)-1-methylcarboxamidoethylcarboxamido]-5-tert-butoxycarboxamidopentylcarboxamido}-4-pentenoate (311 mg, 0.52 mmol) to yield methyl (7S,13S,10S)-10-(4-tert-butoxycarboxamidobutyl)-13-methylcarboxamido-9,12-dioxo-2-oxa-8,11-diazabicyclo[13.2.2]nonadeca-1(17),4,15,18-tetraene-7-carboxylate (228 mg, 0.40 mmol, 76%) as a brown solid. Mass Spectrum (ES, +ve) m/z 475.3 (40%) [MH$^+$ (less t-boc)], 575.3 (25%) [MH$^+$].

Example 48

4-[(3S,9S,6S)-3-Methylcarboxamido-9-methyloxycarbonyl-4,7-dioxo-14-oxa-5,8-diazabicyclo[13.2.2]nonadeca-1(17),11,15,18-tetraen-6-yl]butylammmonium chloride

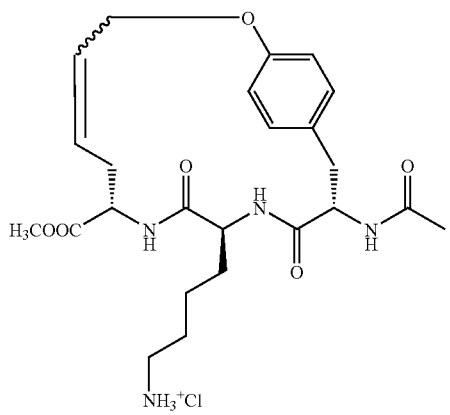

This ammonium salt was synthesized using the general N-Boc deprotection procedure (Procedure A) using methyl (7S,13S,10S)-10-(4-tert-butoxycarboxamidobutyl)-13-methylcarboxamido-9,12-dioxo-2-oxa-8,11-diazabicyclo[13.2.2]nonadeca-1(17),4,15,18-tetraene-7-carboxylate (220 mg, 0.380 mmol) to yield 4-[(3S,9S,6S)-3-methylcarboxamido-9-methyloxycarbonyl-4,7-dioxo-14oxa-5,8-diazabicyclo[13.2.2]nonadeca-1(17),11,15,18-tetraen-6-yl]butylammmonium chloride (152 mg, 0.300 mmol, 79%) as a dark yellow solid. Mass Spectrum (ES, +ve) m/z 475.4 (100%) [M+ (less Cl−)].

Examples 49

Methyl (2S)-2-[(1S)-1-[(1S)-2-(4-allyloxyphenyl)-1-methylcarboxamidoethylcarboxamido]-5-di(tert-butoxycarboxamido)methyleneaminopentylcarboxamido]-4-pentenoate

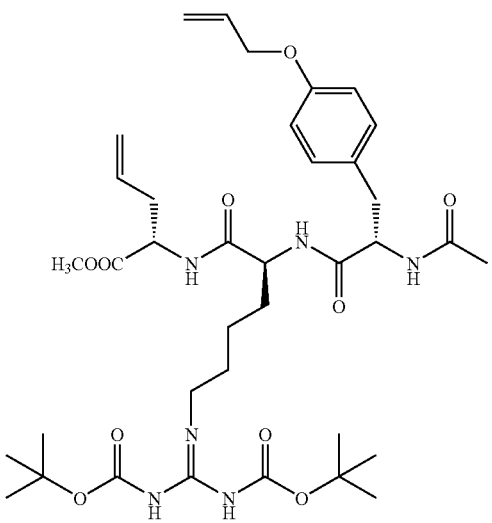

To a solution of (5S)-5-[(1S)-2-(4-allyloxyphenyl)-1-methylcarboxamidoethylcarboxamido]-5-[(1S)-1-methyloxycarbonyl-3-butenylcarbamoyl]pentylammonium chloride (41 mg, 0.081 mmol) in DCM (2 mL) N,N'-diBoc-N"-triflylguanidine (35 mg, 0.089 mmol), triethylamine (0.1 mL) and DCM (2 mL). The resulting solution was allowed to stir overnight in a nitrogen atmosphere. The solvent was evaporated and the crude product was purified by flash column chromatography (15:1, DCM/MeOH) to yield methyl (2S)-2-[(1S)-1-[(1S)-2-(4-allyloxyphenyl)-1-methylcarboxamidoethylcarboxarnido]-5-di(tert-butoxycarboxamido)methyleneaminopentylcarboxamido]-4-pentenoate (45 mg, 0.060 mmole, 74%) as an orange/yellow solid. ¹H NMR (CDCl₃, 300 MHz): δ 8.26 (bs, 1H); 7.08 (t, J 8.4 Hz, 2H); 6.97 (m, 1H); 6.83 (t, J 8.4 Hz, 2H); 6.73 (d, J 8.0 Hz, 1H); 6.57 (t, J 9.3 Hz, 1H); 6.03 (m, 1H); 5.66 (m, 1H); 5.39 (d, J 17.3 Hz, 1H); 5.26 (d, J 10.1 Hz, 1H); 5.10 (m, 2H); 4.51 (m, 5H); 3.74 (s, 3H); 3.33 (bs, 2H); 2.96 (ddd, J 6.7, 7.2, 14.0 Hz, 2H); 2.52 (m, 2H); 1.97 (s, 3H); 1.47 (m, 6H); 1.54 (s, 3H); 1.49 (s, 18H). ¹³C NMR (CDCl₃, 300 MHz): δ 171.7; 171.3; 171.2; 170.9; 170.6; 163.2; 157.5; 156.0; 153.1; 151.4; 133.1; 132.0; 130.1; 128.2; 119.2; 119.0; 117.5; 114.8; 83.2; 79.5; 68.7; 55.2; 53.1; 53.0; 52.4; 40.7; 40.5; 37.2; 36.1; 32.0; 28.6; 28.3; 22.9. Mass Spectrum (ES, +ve) m/z 745.2 (100%) [MH+]. HRMS calcd for C₃₇H₅₇N₆O₁₀ 745.4136. found 745.4105.

Example 50

(5S)-5-[(1S)-2-(4-Allyloxyphenyl)-1-methylcarboxamidoethylcarboxamido]-5-[(1S)-1-methyloxycarbonyl-3-butenylcarbamoyl]pentylguanidinium chloride

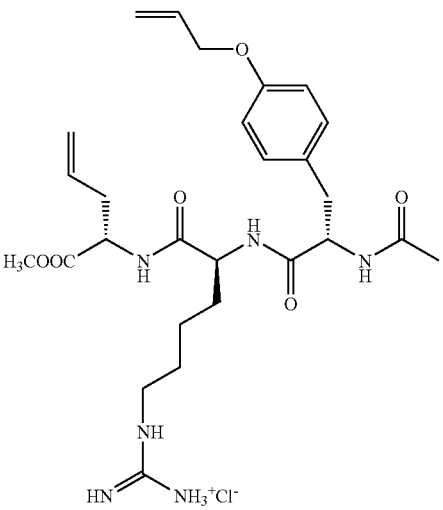

This salt was synthesized using the general N-Boc deprotection procedure (Procedure A) on the compound of Example 49. Mass Spectrum (ES, +ve) m/z 545.3 (100%) [M+]. HRMS calcd for C₂₇H₄₁N₆O₆ 545.3088. found 545.3066.

Example 51

Methyl (7S,13S,10S)-10-[4-di(tert-butoxycarboxamido)methyleneaminobutyl]-13-methylcarboxamido-9,12-dioxo-2-oxa-8,11-diazabicyclo[13.2.2]nonadeca-1(17),4,15,18-tetraene-7-carboxylate

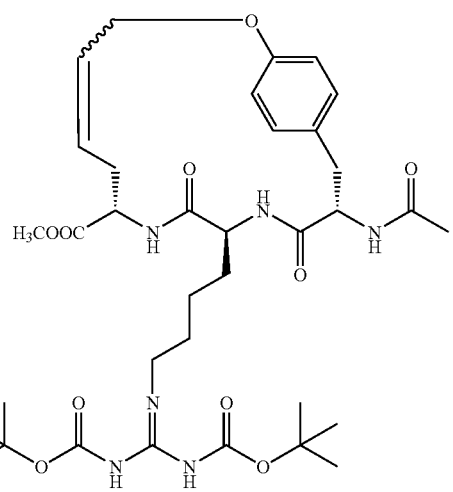

In an anlogous manner to Example 49, the compound of Example 48 was converted to its protected guanidine analogue. Isolated as an orange/yellow solid. Mass Spectrum (ES, +ve) m/z 717.4 (100%) [MH$^+$]. HRMS calcd for $C_{35}H_{53}N_6O_{10}$ 717.3823. found 545.3806.

Example 52

Imino{4-[(3S,6S,9S)-3-methylcarboxamido-9-methyloxycarbonyl-4,7-dioxo-14oxa-5,8-diazabicyclo[13.2.2]nondeca-1(17),11,15,18-tetraen-6-yl]butylamino}methylammonium chloride

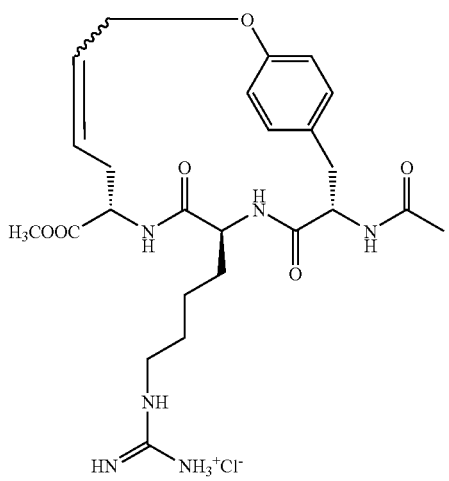

Deprotection procedure (Procedure A) of Example 51 gave the desired compound as a yellow solid. Mass Spectrum (ES, +ve) m/z 517.4 (100%) [M$^+$ (less Cl$^-$)]. HRMS calcd for $C_{25}H_{37}N_6O_6$ 517.2775. found 517.2765.

Examples 53–60

In an analogous manner, the series of compounds corresponding to the compounds of Examples 45–52 but where the L-lysine was replaced with D-lysine were prepared.

Examples 61–64

A series of compounds corresponding to the compounds of Examples 45–48 but where the L-allyl glycine was replaced with D-allyl glycine, and L-lysine was replaced with D-arginine were prepared in an analogous manner to the compounds of Examples 45–48. The arginine was Pmc protected.

Examples 65–68

In an analogous manner, the series of compounds corresponding to the compounds of Examples 61–64 but where the D-arginine was replaced with L-arginine were prepared.

Compounds Based on a 1,3-Substituted Indole Nucleus

Nomenclature of cyclic peptoids based on a 1,3-substituted indole nucleus. These compounds are named as bridged compounds with the metheno bridge between the atoms 1 and 15. The macrocyle is then label and numbered as illustrated below.

Methyl 1,2,5,6,7,9,10,12,13,14-octahydro-1,15-metheno-7,10-diaza-8,11-dioxo-9-4'(tert-butoxycarbonylamino)butyl-1-benzazacyclododecine-6-carboxylate

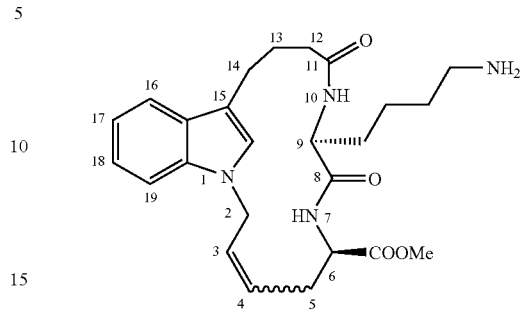

Example 69

Preparation of 1-Prop-2-enyl 1-(1-prop-2-enyl)-indole-3-acetate and 1-Prop-2-enyl 1H-indole-3-acetate

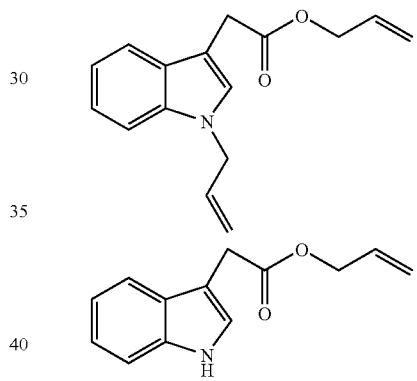

Sodium hydride (1.0 g, 25.1 mmol, 2.2 molar equiv., 60% in paraffin) was washed with petroleum spirit twice under a N$_2$ atmosphere before dry DMF was added. A solution of 1H-indole-3-acetic acid (2.0 g, 11.4 mmol) in DMF under N$_2$ was added to this suspension at room temperature and the mixture was stirred for half an hour. Allyl bromide (2.5 mL, 28.6 mmol, 2.5 molar equiv) was added dropwise and the reaction mixture was stirred overnight at room temperature. The DMF was evaporated and the residue was partitioned between diethyl (20 mL) and water (20 mL). The diethyl layer was separated and the aqueous layer was extracted further with diethyl ether. The combined diethyl ether layers were washed with water, dried (Na$_2$SO$_4$) and evaporated. The crude product was chromatographed on a flash silica gel column (20% DCM in petroleum spirit as eluent) to produce the diallyl derivative as an oil (1.9 g, 95%) and the allylester (90 mg) upon elution with 50% DCM in petroleum spirit. For 25: MS (CI) m/z 256 (100% MH$^+$). HRMS (CI) calcd for $C_{16}H_{18}NO_2$: 256.1338. found: 256.1338.

For the diallyl derivative: MS (CI) m/z 216 (100% MH$^+$). HRMS (CI) calcd for $C_{13}H_{14}NO_2$: 216.1024. found: 216.1021.

Example 70

Preparation of 1-(1-prop-2-enyl)-1H-indole-3-acetic acid

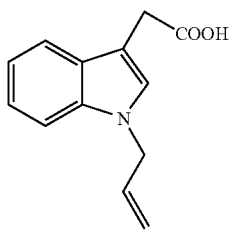

To a solution of the diallyl from example 69 (1.8 g, 7.2 mmol) was added lithium hydroxide (0.3 g, 0.15M) dissolved in a ratio of 2.5:1 THF/water (35 mL). The reaction mixture was placed in ice and stirred at 0° C. for 3 hours. The solvent of THF was evaporated and the crude was extracted with diethyl and water. The aqueous layer was separated with diethyl layer and extracted with water. The combined aqueous layers were acidified by 10% hydrochloride acid to pH less than 2. The aqueous layer was then saturated with sodium chloride and extracted with DCM (20 mL), dried ($Na_2SO_4$) and evaporated. The titled compound (1.1 g, 74%) was obtained as an oil. $^1$H NMR ($CDCl_3$) δ=7.60 (d, J=8 Hz, 1 H, ArH-4), 7.30 (d, J=8 Hz, 1 H, ArH-7), 7.22 (dt, J=8, 1 Hz, 1 H, ArH-6), 7.13 (dt, J=8, 1 Hz, 1 H, ArH-5), 7.08 (s, 1 H, ArH-2), 5.98 (ddt, J=17, 11, 5 Hz, 1 H, C$\underline{H}$=$CH_2$), 5.20* (dd, J=9, 1 Hz, 2 H, CH=C$\underline{H}_2$), 5.11 (dd, J=16, 1 Hz, 2 H, CH=C$\underline{H}_2$), 4.68 (dd, J=5, 1 Hz, 2H, NC$\underline{H}_2$CH=$CH_2$), 3.80 (s, 2 H, $CH_2$C=O); $^{13}$C NMR δ=177.5 (C=O), 136.1 (ArC), 133.2 ($\underline{C}$H=$CH_2$), 127.6 (ArC), 126.8, 121.8 and 119.3 (ArCH), 118.9 (CH=$\underline{C}H_2$), 117.4 and 109.6 (ArCH), 106.4 (ArC), 48.8 ($NCH_2$), 31.0 ($CH_2$); MS (CI) m/z 216 (100% MH$^+$). HRMS (CI) calcd for $C_{13}H_{14}NO_2$: 216.1024. found: 216.1039.

Example 71

Preparation of N-[(1S)-1-[[[(1S)-1-methoxycarbonyl-3-butenyl]amino]carbonyl]-5(tert-butoxycarbonylamino)pentyl]-1-(1-prop-2-enyl)-1H-indole-3-acetamide

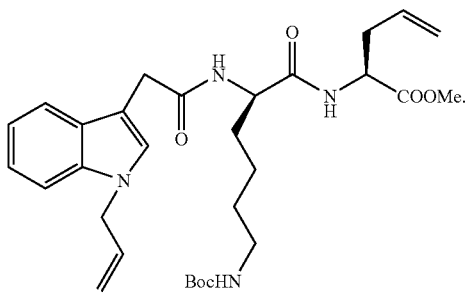

The compound of Example 70 (0.05 g, 0.2 mmol) in DCM (3 mL) was coupled to N-Boc-D-lysine-L-allylglycine methyl ester (0.08 g, 0.2 mmol) in the standard manner to produce the titled compound (0.08 g, 100%) as a solid. $^1$H NMR ($CDCl_3$) δ=7.52 (d, J=8 Hz, 1 H, ArH-4), 7.29 (d, J=8 Hz, 1 H, ArH-7), 7.20 (t, J=8 Hz, 1 H, ArH-6), 7.10 (t, J=8 Hz, 1 H, ArH-5), 7.06 (s, 1 H, ArH-2), 6.78 (d, J=8 Hz, 1 H, NH-3'), 6.21 (d, J=8 Hz, 1 H, NH-6'), 5.97 (ddt, J=17, 11, 5 Hz, 1 H, NCH$_2$C$\underline{H}$=$CH_2$), 5.61 (m, 1 H, CHCH$_2$C$\underline{H}$=$CH_2$), 5.18 (d, J=10 Hz, 1 H, CH=C$\underline{H}$H), 5.09–5.04 (m, 3 H, CH=$CH_2$+CH=CH$\underline{H}$), 4.69 (d, J=6 Hz, 2 H, NC$\underline{H}_2$—CH=$CH_2$), 4.53 (m, 1 H, αCH-2'), 4.43 (m, 1 H αCH-5'), 3.72 (s, 2 H, $CH_2$-8'), 3.68 (s, 3 H, $OCH_3$), 2.93 (d, J=5 Hz, 2 H, NC$\underline{H}_2$($CH_2$)$_3$), 2.53–2.35 (m, 2 H, CHC$\underline{H}_2$CH=$CH_2$), 1.77–1.66 (m, 1 H, N($CH_2$)$_3$C$\underline{H}_2$) 1.41 (s, 9 H, Boc), 1.45–1.27 (m, 4 H, N($CH_2$)$_3$$CH_2$+NCH$_2$C$\underline{H}_2$($CH_2$)$_2$), 1.15–1.08 (m, 2 H, N($CH_2$)$_2$C$\underline{H}_2$$CH_2$).

Example 72

Preparation of N-[(1S)-1-[[[(1S)-1-methoxycarbonyl-3-butenyl]amino]carbonyl]-5'-amino-pentyl]-1-(1-prop-2-enyl)-1H-indole-3-acetamide

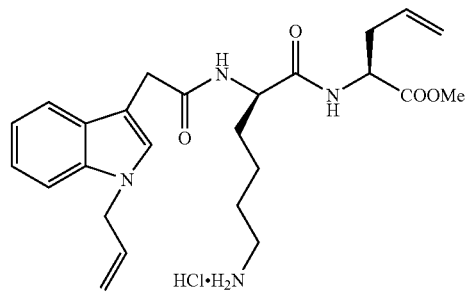

The compound of Example 71, was deprotected in the standard manner to provide the titled compound as a brown solid. mp 103–106° C.; MS (ES) m/z 455 (100% MH$^+$), 326 (79% M$^+$-(NHCH($CH_2$CH=$CH_2$)COOCH$_3$). HRMS (ES) calcd for $C_{25}H_{35}N_4O_4$: 455.2658. found: 455.2663.

Example 73

Preparation of methyl-1,2,5,6,7,9,10,12-octahydro-1,13-metheno-7,10-diaza-8,11-dioxo-9-4'(tert-butoxycarbonylamino)butyl-1-benzazacyclododecine-6-carboxylate

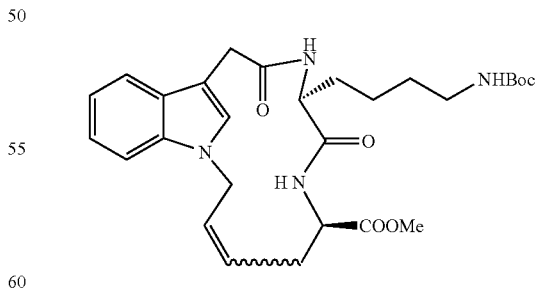

Ring closure of the compound of Example 71 in the standard manner gave the cyclic compound as a brown amorphous solid. MS (ES) m/z 527 (45% MH$^+$), 471 (56% MH$^+$—CMe$_3$), 453 (74% M$^+$-OC($CH_3$)$_3$), 427 (100% MH$^+$-Boc). HRMS (ES) calcd for $C_{23}H_{31}N_4O_4$: 527.2870. found: 527.2870.

Example 74

Preparation of methyl-1,2,5,6,7,9,10,12-octahydro-1,13-metheno-7,10-diaza-8,11-dioxo-9-4'-aminobutyl-1-benzazacyclododecine-6-carboxylate

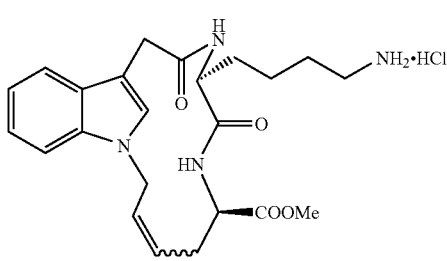

Deprotection of the compound of Example 73 in the standard manner gave the titled compound as a brown solid. mp 168–170° C.; $^1$H NMR (CD$_3$OD, 500 MHz) δ=7.39 (d, J=8 Hz, 1 H, ArH-14″), 7.27* (d, J=8 Hz, ArH-17″), 7.21 (d, J=8 Hz, 1 H, ArH-17″), 6.98 (t, J=8 Hz, 1 H, ArH-16″), 6.93 (s, 1 H, ArH-18″), 6.88 (t, J=8 Hz, 1 H, ArH-15″), 5.78* (dd, J=10, 5 Hz, CH-3″), 5.52 (dt, J=15, 5 Hz, 1 H, CH-3″), 5.40* (dd, J=10, 5 Hz, CH-4″), 4.88–4.83 (dt, J=15, 8 Hz, 1 H, CH-4″), 4.59 (dd, J=9, 3 Hz, 1 H, CHH-2″), 4.36 (dd, J=9, 6 Hz, 1 H, CHH-2″), 4.20 (t, J=7 Hz, 1 H, CH-9″), 4.10 (dd, J=9, 5 Hz, 1 H, CH-6″), 3.67 (d, J=9 Hz, 1 H, CHH-12″), 3.51 (s, 3 H, OCH$_3$), 3.31 (d, J=9 Hz, 1H CHH-12″), 2.74 (dd, 2 H, NCH$_2$(CH$_2$)$_3$), 2.51–2.42* (m, CHH-5″), 2.41–2.34 (m, 1 H, CHH-5″), 2.12 (ddd, J=14, 6 Hz, 1 H, CH H-5″), 1.69–1.49 (m, 2 H, N(CH$_2$)$_3$CH$_2$), 1.58–1.48 (m, 2 H, NCH$_2$CH$_2$(CH$_2$)$_2$), 1.36–1.23 (m, 2 H, N(CH$_2$)$_2$CH$_2$CH$_2$).

Example 75

Preparation of methyl-1,2,5,6,7,9,10,12-1,13-metheno-7,10-diaza-8,11-dioxo-9-4'(ditert-butoxycarbonylamino)pentylguanidine-1-benzazacyclododecine-6-carboxylate

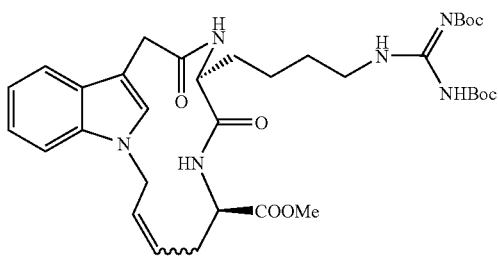

Guanidation of the compound of Example 74 according to the general procedure of Example 49 gave the titled compound. MS (ES) m/z 669 (27% MH$^+$). HRMS (ES) calcd for C$_{34}$H$_{49}$N$_6$O$_8$: 669.3612. found: 669.3624.

Example 76

Preparation of methyl-1,2,5,6,7,9,10,12-octahydro-1,13-metheno-7,10-diaza-8,11-dioxo-9-4'-pentylguanidine-1-benzazacyclododecine-6-carboxylate

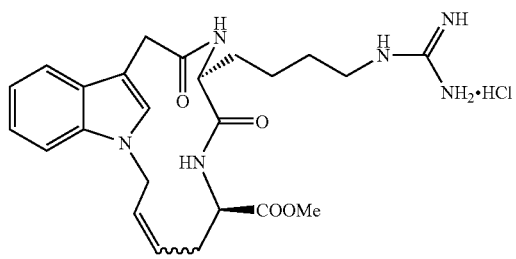

Deprotection of the compound of Example 75 in the standard manner produced the titled compound (0.06 g, 75%) as a brown solid. mp 151–154° C.

Examples 77–84

A series of compounds corresponding to the compounds of Examples 69–76 but where a propanoate was attached at the 3-position of the indole rather than an acetate were prepared in an analogous manner to the compounds of Examples 69–76.

Examples 85–92

A series of compounds corresponding to the compounds of Examples 69–76 but where a butanoate was attached at the 3-position of the indole rather than an acetate were prepared in an analogous manner to the compounds of Examples 69–76.

Compounds Based on a 2,2'-Substituted Binaphthyl Nucleus

Example 93

Synthesis of (aR/S)-2'-allyloxy-1,1'-binaphth-2-ol

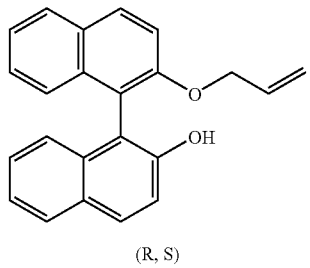

(R, S)

1,1'-binaphthol-2,2'-diol (4.8678 g, 17 mmol) in acetone (20 ml) was stirred with 3 g of anhydrous granules potassium carbonate (3.0 g) and molecular sieve (5.0 g) 3 Å for 1 h under nitrogen prior to the slow addition of allyl bromide (2 ml). The reaction mixture was refluxed for 24 h and then was left to cool. The mixture was filtered off and the solid being washed with acetone until colourless filtrate appeared. The combined filtrate was evaporated to dryness and the residue was taken up in 50 ml of dichloromethane and filtered to remove any remaining potassium salts. The compound was purified by chromatography using dichloromethane/hexane (1:2), $R_f$=0.8. Yield 4.0 g, m.p. 111° C. lit mp: 112.5–114, Nakamura et al., Helvetica Chimica Acta, 58(7), (1975), 214–215.

Example 94

Synthesis of ethyl (aR/S)-(2'-allyloxy-1,1'-binaphth-2-oxy)ethanoate

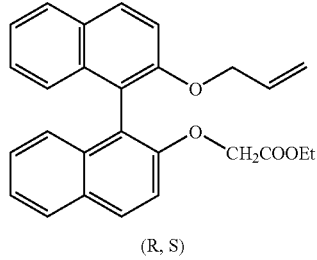

(R, S)

Example 93 (3.631 g, 11.138 mmol) in dry acetone (10 ml) was stirred with anhydrous potassium carbonate (2.35 g) for 1 h under nitrogen prior to the addition of the ethyl bromoacetate (1.86 g, 11.138 mmol, 1.24 ml). After the reaction being stirred overnight the reaction mixture was filtered. The solid being washed repeatedly with acetone. The filtrate was evaporated to dryness and the residue was taken up in chloroform (50 ml) then filtered. The product isolated as a colourless semisolid by using column chromatography chloroform/hexane 20% increase to 60%. Yield: 4.33 g. MS, m/z for $C_{27}H_{24}O_4$: 413 (M+1) 100%; 339 (M$^+$-COOC$_2$H$_5$) 11%.

Example 95

Synthesis of (aR/S)-(2'-allyloxy-1,1'-binaphth-2-oxy)ethanoicacid

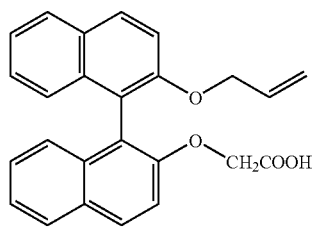

(R, S)

Example 94 (0.1386 g, 0.336 mmol) was dissolved in THF (0.047 M, 4 ml). To this ice-cooled solution was added a solution of lithium hydroxide monohydrate (1.513 mmol, 0.063 g) in water (9 ml). The mixture was allowed to gradually warm to room temperature and was stirred for 5 h. To the reaction mixture was added diethyl ether. The aqueous layer was separated and washed with ether (20 ml×2) and the combined ether layers extracted with water (50 ml×2). The combined aqueous layers were acidified (dilute hydrochloric acid) then extracted with diethyl ether (20 ml×3) then dried over anhydrous magnesium sulfate. The filtrate was evaporated to dryness to afford the required product as off white precipitate, m.p. 77–80° C.

Example 96

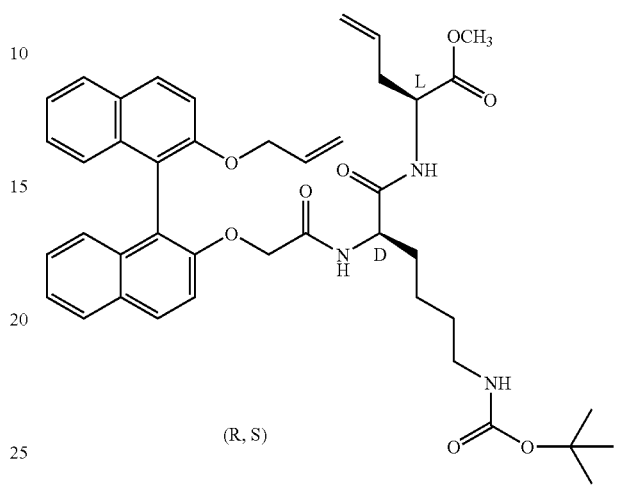

(R, S)

Example 95 (0.2689 g, 0.700 mmol) and N$_\epsilon$-Boc-D-lys-L-allylglycine methyl ester (0.25 g, 0.700 mmol) were coupled in the normal manner to give white solid, m.p. 54–6° C. Yield 0.3 g. $^1$H NMR (CDCl$_3$, 300 MHz) δ 8.015–7.982 (d, 1H, J=5.7 Hz), 7.982–7.955 (d, 1H, J=5.7 Hz), 7.910–7.886 (d, 1H, J=4.2 Hz), 7.886–7.860 (d, 1H, J=4.2 Hz), 7.510–7.469 (d, 1H, J=9.3 Hz), 7.469–7.433 (d, 1H, J=9.0 Hz), 7.396–7.100 (m, 6H), 6.638–6.609 (d, 1H—N, J=7.5 Hz), 6.491–6.461 (d, 1H—N, J=7.8 Hz), 6.182 (dd, 1H, J$_1$=7.8, J$_2$=12.0 Hz), 5.699–5.520 (m, 2H, HC=allyl), 5.109–4.885 (m, 4H), 4.581–4.459 (m, 6H), 4.116–4.060 (m, 1H), 3.685 (s, 3H), 2.980–2.865 (m, 2H), 2.570–2.350 (m, 2H), 1.679 (br, 2H), 1.455 & 1.436 (s, 9H, R, S isomers), 1.350–1.200 (m, 2H), 1.060–0.760 (m, 2H). MS, m/z for $C_{42}H_{49}N_3O_8$: 723 (M$^+$) 25%; 722 (M$^+$–1) 100%; 348 18%.

Example 97:

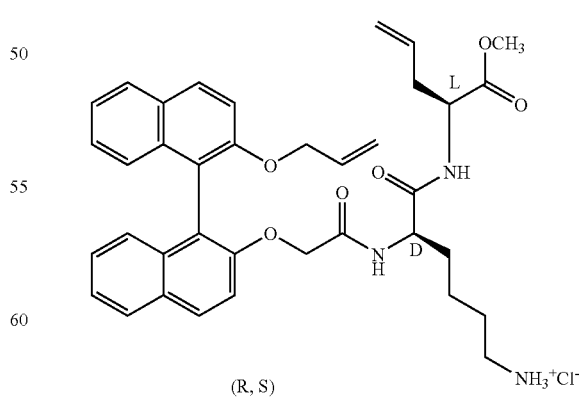

(R, S)

Deprotection of Example 96 in the normal manner provided the product. $^1$H NMR (DMSO-d$_6$, 300 MHz) δ: 8.290–8.216 (m, 1H), 8.055–8.022 (m, 2H), 7.959–7.925

(m, 2H), 7.743 (br, 3H—N) 7.568–7.478 (m, 2H), 7.378–7.305 (m, 2H), 7.269–7.190 (m, 2H), 7.050–6.870 (m, 3H), 5.801–5.605 (m, 2H), 5.120–4.920 (m, 4H), 4.610–4.250 (m, 6H), 3.611, 3.602 (s, 3H, R & S), 2.637 (br, 2H), 2.450–2.310 (m, 2H), 1.500–0.860 (m, 6H). MS, m/z: 625 (M$^+$+1) 100%; 626, 19%; 737 (M$^-$+TFA) 66%.

Example 98

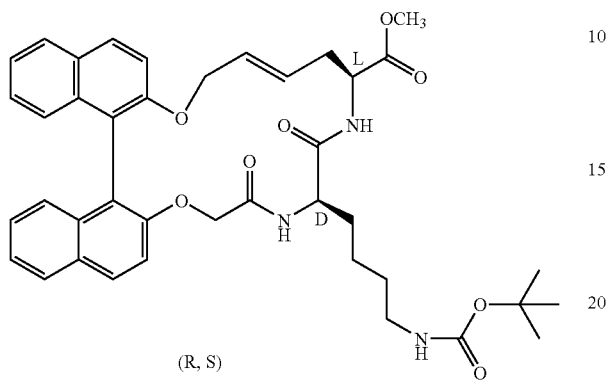

Cyclisation of Example 96 in the usual manner gave the product.

$^1$H NMR (CDCl$_3$, 300 MHz) δ: 8.103–7.810 (br, 1H), 8.04–7.97 (m, 2H), 7.930–7.875 (m, 2H), 7.502 (dd, 1H, J$_1$=4.2, J$_2$=8.7 Hz), 7.390–7.315 (m, 3H), 7.285–7.090 (m, 4H), 6.512 (dd, 1H, J$_1$=7.8, J$_2$=38.7 Hz), 6.135 (dd, 1H, J$_1$=4.2, J$_2$=7.5 Hz), 5.733–5.523 (m, 2H), 5.110–5.880 (m, 4H), 4.583–4.469 (m, 5H), 4.120–4.058 (m, 1H), 3.682 (s, 3H), 3.212 (dd, 2H, J$_1$=7.2, J$_2$=12.6 Hz), 2.577–2.363 (m, 2H), 1.502, 1.486 (2×s, 9H, Boc), 1.458–1.354 (m, 2H), 1.018–0.810 (m, 4H). MS m/z for C$_{40}$H$_{45}$N$_3$O$_8$: 696 (M$^+$+1) 52%; 695 (M$^+$) 44%; 694 (M$^+$–1) 100%.

Example 99

Deprotection of Example 98 in the usual manner the product.

MS m/z for C$_{35}$H$_{38}$ClN$_3$O$_6$: 596 (M$^+$) 100%; 597 40%.

Example 100

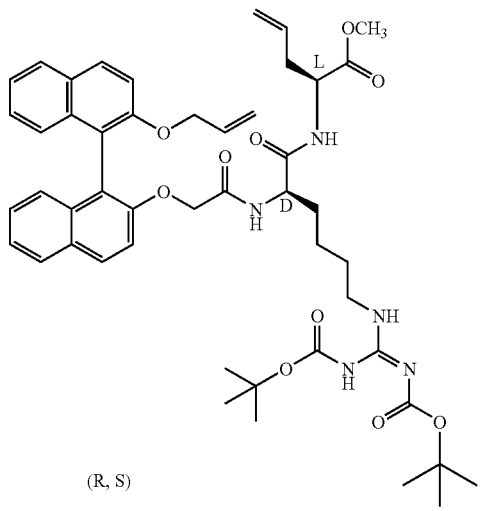

The compound was prepared by guanidation of Example 97 in the usual manner.

$^1$HNMR (CDCl$_3$, 300 MHz) δ: 8.273–8.212 (br, 1H), 8.04–7.97 (m, 2H), 7.930–7.875 (m, 2H), 7.502 (dd, 1H, J$_1$=4.2, J$_2$=8.7 Hz), 7.390–7.315 (m, 3H), 7.285–7.090 (m, 4H), 6.512 (dd, 1H, J$_1$=7.8, J$_2$=38.7 Hz), 6.135 (dd, 1H, J$_1$=4.2, J$_2$=7.5 Hz), 5.733–5.523 (m, 2H), 5.110–5.880 (m, 4H), 4.583–4.469 (m, 5H), 4.120–4.058 (m, 1H), 3.682 (s, 3H, methyl), 3.212 (dd, 2H, J$_1$=7.2, J$_2$=12.6 Hz), 2.577–2.363 (m, 2H), 1.502 (s, 9H, Boc), 1.486 (s, 9H, Boc), 1.458–1.354 (m, 2H), 1.018–0.810 (m, 4H). MS, m/z for C$_{48}$H$_{59}$N$_5$O$_{10}$: 867 (M$^+$+1) 100%; 867 67%; 868 67%.

Example 101

Preparation of methyl (aR/S,2S,5R)-2-allyl-5-[2-({[(2'-allyloxy-1,1'-binaphthoxymethyl]carbonyl}amino)-3-aza-9-guanidino-4-oxononanoate hydrochloride

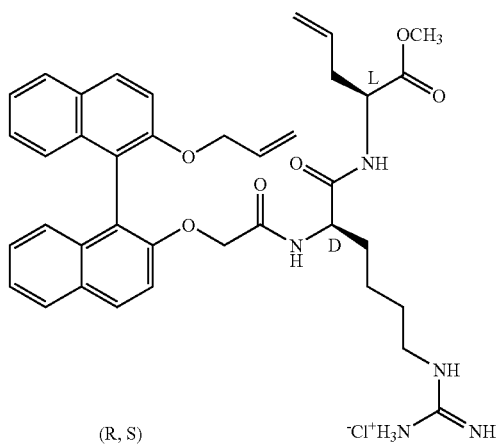

The compound was prepared by deprotection of Example 100 in the usual manner. MS, m/z for C$_{38}$H$_{44}$ClN$_5$O$_6$: 666 (M$^+$+1) 100%; 667 25%; 668 7%; 664 100%; 665 55%.

Example 102

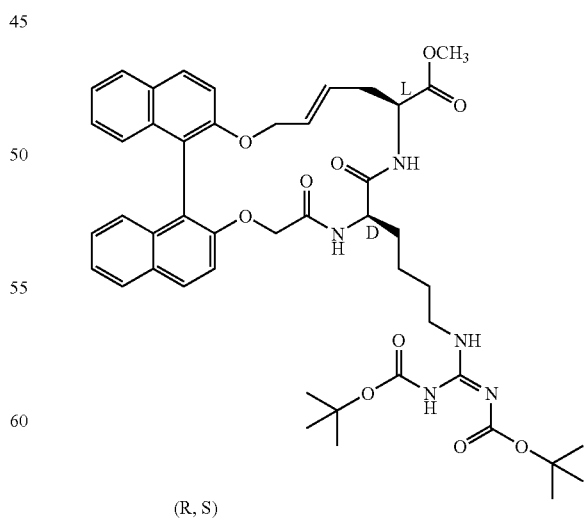

The compound was prepared by guanidation of Example 99 in the usual manner, m.p. 108° C.

Example 103

Preparation of (aR,S,7R,10S)-6,9-diaza-3,15-dioxa-5,8-dioxo-7-(4-guanidinobutyl)-10-methoxycarbonyl-1(1,2),2(1,2)-dinaphthalenacyclopentadecaphane-12-ene hydrochloride

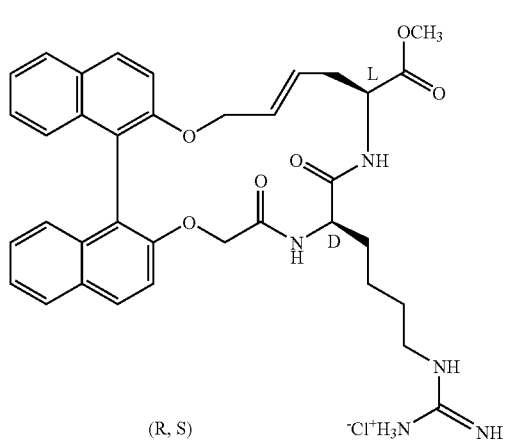

The compound was prepared by deprotection of Example 102 in the usual manner. MS, m/z for $C_{36}H_{40}ClN_5O_6$: 638 (M$^+$+1) 100%; 639 55%.

Examples 104–113

A series of compounds corresponding to the compounds of Examples 94–103 but where the corresponding butanoate was prepared rather than an ethanoate were prepared in an analogous manner to the compounds of Examples 94–103.

Example 104

Synthesis of ethyl (aR/S)-(2'-allyloxy-1,1'-binaphth-2-oxy)butanoate

MS, m/z for $C_{29}H_{28}O_4$: 441 (M$^+$+1) 14.5%; 115 ($CH_2CH_2CH_2COOC_2H_5^+$) 100%.

Example 105

Synthesis of (aR/S)-(2'-allyloxy-1,1'-binaphth-2-oxy)butanoic acid

MS, m/z for $C_{27}H_{24}O_4$: 412 (M$^+$+1) 77.1%; 395 81.5%; 355 (M$^+$–OCH$_2$CHCH$_2$) 12.8%; 87 ($CH_2CH_2CH_2COOH^+$) 100%.

Example 106

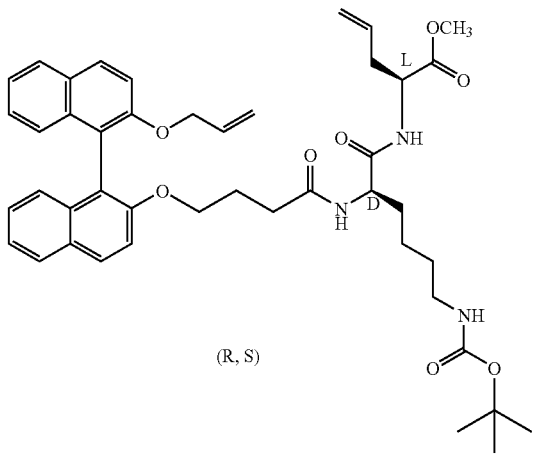

m.p. 90° C. $^1$H NMR (CDCl$_3$, 300 MHz) δ: 7.985–7.850 (m, 4H), 7.466–7.300 (m, 4H), 7.238–7.130 (m, 4H), 6.558 (t, 1H—N, J=7.5 Hz), 5.749–5.591 (m, 2H, HC=allyl), 5.451 (dd, 1H—N, J$_1$=7.5, J$_2$=19.2 Hz), 5.117–4.930 (m, 4H, OCH$_2$), 4.640–4.540 (m, 3H), 4.275–3.840 (m, 3H), 3.725, 3.693 (s, 3H 1:1), 3.08–2.950 (m, 2H), 2.578–2.450 (m, 2H), 1.965–1.570 (m, 10H), 1.442, 1.424 (s, 9H, Boc, 1:1), 1.363–1.080 (m, 2H).

Example 107 methyl (aS/R,2S,5R)-2-allyl-10-(2'-allyloxy-1,1'-binaphth-2-oxy)-5-(4-aminobutyl)-3,6-diaza-4,7-dioxodecanoate hydrochloride

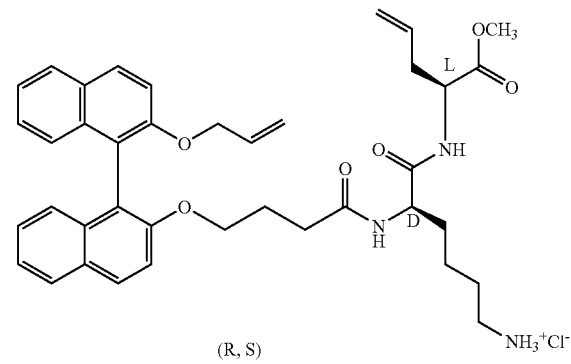

MS, m/z for $C_{39}H_{46}ClN_3O_6$: 652 (M$^+$+1) 100%; 653 81%; 654 44%.

Example 108
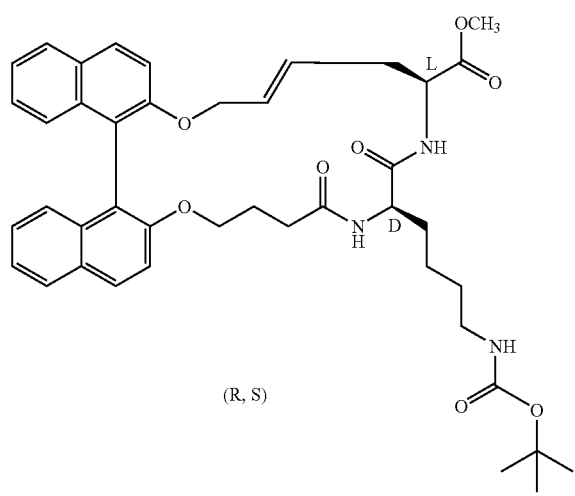
(R, S)
MS, m/z for $C_{42}H_{49}N_3O_8$: 724 (M$^+$+1) 76%; 725 40%; 768 100%; 624 (M$^+$-Boc) 20%; 593 38%; 521 48%.
Example 109
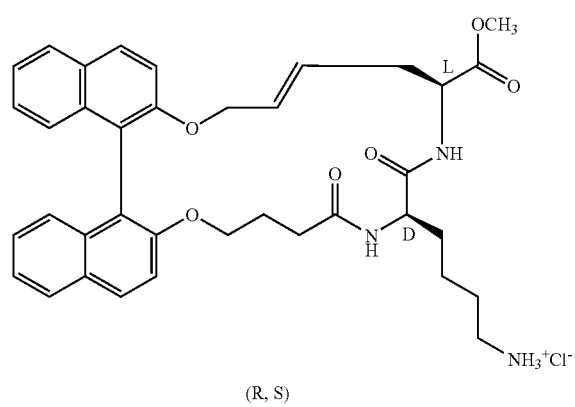
(R, S)
MS m/z for $C_{37}H_{42}ClN_3O_6$: 624 (M$^+$+1) 100%; 625 42%; 622 52%; 623 17%.
Example 110
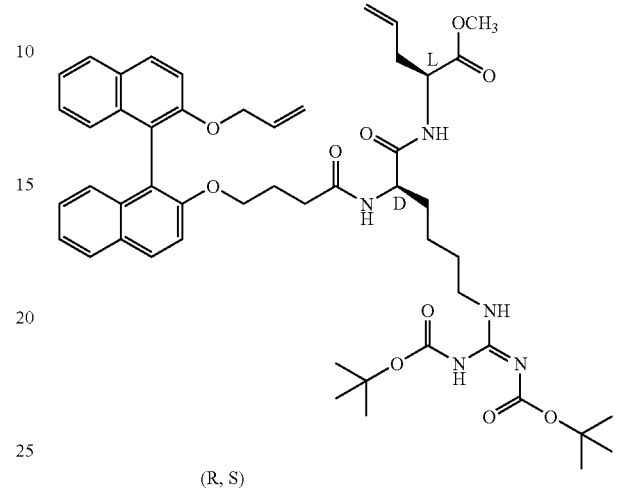
(R, S)
MS, m/z for $C_{50}H_{63}N_5O_{10}$: 894 (M$^+$+1) 100%; 895 70%, 896 20%.
Example 111
Preparation of methyl (aS/R,2S,5R)-2-allyl-10-(2'-allyloxy-1,1'-binaphth-2-oxy)-3,6-diaza-5-(4-guanidinobutyl)-4,7-dioxodecanoate hydrochloride
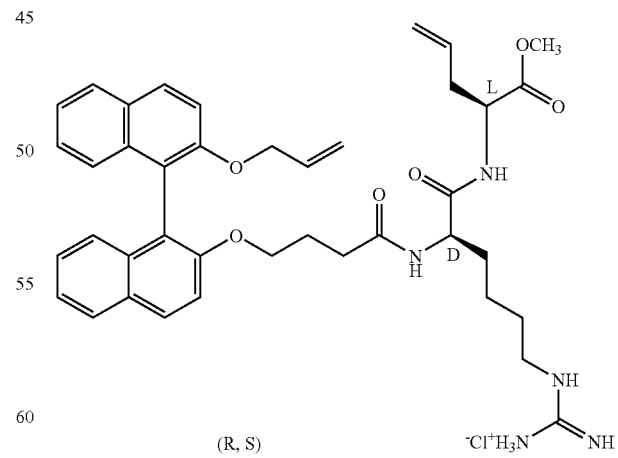
(R, S)
MS, m/z for $C_{40}H_{48}ClN_5O_6$: 694 (M$^+$+1) 92%; 695 15%; 693 22%; 692 35%.

Example 112

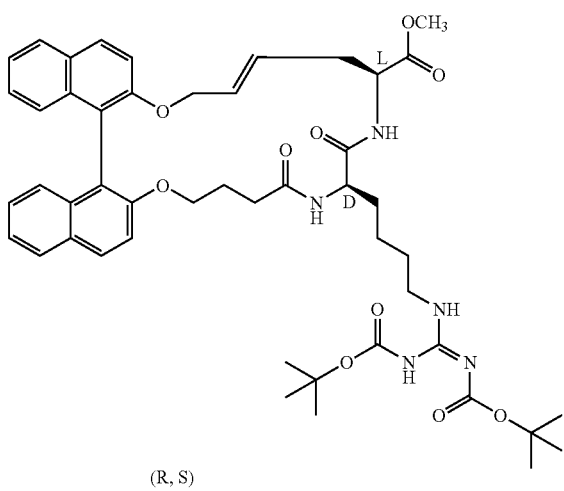

(R, S)

m.p. 95° C. (d). MS, m/z for $C_{48}H_{59}N_5O_{10}$: 866 ($M^+$+1) 100%; 867 45%.

Example 113

Preparation of (aR/S,9R,12S)-8,11-diaza-9-(4-guanidinobutyl)-12-methoxycarbonyl-1(1,2),2(1,2)-dinaphthalena-3,17-dioxa-7,10-dioxoheptadecaphane-15-ene hydrochloride

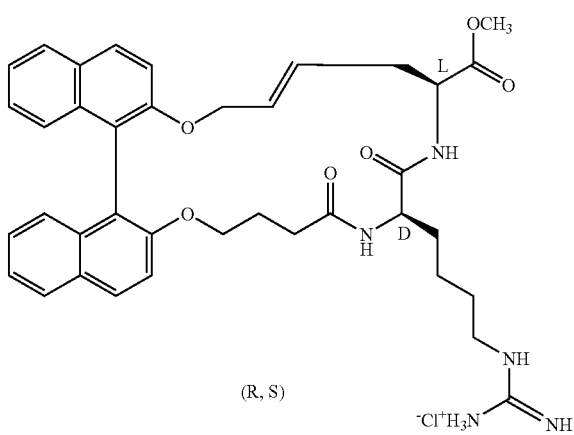

(R, S)

MS, m/z for $C_{38}H_{44}ClN_5O_6$: 666 ($M^+$+1) 100%; 667 40%.

Biological Testing:
General Methods for Antibacterial Screens
Definitions
SA: *Staphylococcus aureus*
PA: *Pseudomonas aeruginosa*
KP: *Klebsiella pneumoniae*
SP: *Streptococcus pneumoniae*
Bacterial Strains Used:
*Staphylococcus aureus* (ATCC 6538P)
*Pseudomonas aeruginosa* (ATCC 27853)
*Klebsiella pneumoniae* (IP103623)
*Streptococcus pneumoniae* (IP53146)

Culture Media

Mueller-Hinton Broth Medium (MMB): MHB (Oxoid CM405) was prepared with final concentrations of 1 µg/mL $MgCl_2$ and 2 µg/mL $CaCl_2$. Culture medium was pre-warmed for approximately 2–3 hours at 37° C. before use.

Mueller-Hinton Agar medium (MHA): MHB containing 1.5% Agar (Merck Agar 1.01614).

Blood Agar (BA): Oxoid PP 2001.

Maintenance of Bacteria

From thawed cryovials, *P. aeruginosa*, *K. pneumoniae* and *S. aureus* were streaked onto Mueller Hinton Agar (MHA), and *S. pneumoniae* was streaked onto Blood Agar (BA), and plates were incubated overnight at 37° C. For each bacterial strain, 10 cryovials were prepared by looping several colonies into 0.5 mL of 20% glycerol solution. The cryovials were immediately stored at −140° C.

Preparation of Seed Cultures

A cryovial was removed from −140° C. storage and thawed at room temperature. An MHA plate was streaked with a loopful of bacterial suspension and incubated overnight at 37° C. to create a parent plate (P1). A daughter plate (D1) was streaked from the parent plate and incubated overnight at 37° C. The parent plate was stored at 4° C. A loop of colony from the daughter plate was used to inoculate a 125 mL flask containing 20 mL of Mueller Hinton Broth (MHB) containing 25 µg/mL $CaCl_2.2H_2O$ and 12.5 µg/mL $MgCl_2.6H_2O$. The flask was shaken at 260 rpm for 18 hours at 37° C. on an orbital incubator shaker. The parent plate (P1) was reused within 9 days to generate another daughter plate (D2), which, in turn, was used to inoculate a broth culture. Parent plates were used twice (to generate D1 and D2 plates) before a new one was prepared from the previously thawed cryovial. The second parent plate (P2) was used to generate two additional daughter plates using the procedure outlined above before being discarded. Cryovials were used twice to prepare parent plates (P1 and P2) before being discarded.

Preparation of Standardised Inocula for Assays

Prepare a 1/10 dilution of Seed Cultures by adding 250 µl of the cultures to 2,250 µl of MHB in a disposable cuvette. Read $OD_{650}$ and multiply $OD_{650}$ by a factor of 10 to calculate the optical density of the undiluted culture. Calculate the required dilution factor by dividing the observed $OD_{650}$ by the standard $OD_{650}$ for each strain (previously determined in assay optimisation studies).

| | |
|---|---|
| *Klebsiella pneumoniae* | standard $OD_{650}$ = 6.16 |
| *Pseudomonas aeruginosa* | standard $OD_{650}$ = 7.14 |
| *Staphylococcus aureus* | standard $OD_{650}$ = 4.75 |
| *Streptococcus pneumoniae* | standard $OD_{650}$ = 5.18 |

Prepare 10 mL of standardised inocula as illustrated by the following example:

Sample calculation—*Klebsiella pneumoniae*

$OD_{650}$=0.652 (1/10 dilution)

10×0.652=6.52

∴6.16/6.52=0.94

Add 0.94 mL of *Klebsiella pneumoniae* seed culture to 9.06 mL of MHB as the first dilution.

Prepare sufficient volumes of the final inoculum cultures in pre-warmed MHB (37° C.) by diluting the standardised cultures to the required final concentration. The final dilutions used for each of the bacterial strains were as follows:
K pneumoniae—$10^6$ dilution;
P. aeruginosa—$10^6$ dilution;
S. aureus—$10^8$ dilution;
S. pneumoniae—$10^4$ dilution.

Assay Procedure (For 96 Well Microtiter Plates)

Add 50 microlitres of liquid medium to each well of a 96 well microtitre plate. Dissolve test samples in liquid medium. Add 50 microlitres of test sample in triplicate to the top row of the microtitre plate, and include a vancomycin control set. Also include a compound negative control well set. Allow inoculated culture medium to incubate at 37° C. for 30 minutes, shaking at 130 rpm. Using a multichannel pipette, mix the contents of the first row and transfer 50 microlitres of mixed broth solutions to the next row, change tips and repeat until the last row contains diluted compound or control and discard 50 microlitres from the last row. Each well should now contain 50 microlitres of diluted compound or negative control medium. Using a multistepper pipette add 50 microlitres of inoculum to each well of the plate, save for one row containing the compound negative control, to this row add 50 microlitres of liquid broth. Incubate plates at 37° C. for 18 hours, shaking at 100 rpm in an environment of approximately 90% relative humidity. Results were recorded as the highest dilution of compound that prevented bacterial growth MIC).

The compounds of the invention showed MIC's of between 1 and 250 μg per mL.

Results of Certain Compounds against S. aureus

| Example | MIC μg/ml |
|---|---|
| 13A | 4 |
| 15 (one isomer) | 8 |
| 15A | 16 |
| 15B | 16 |
| 19A | 4 |
| 21A (one isomer) | 16 |
| 21A (another isomer) | 64 |
| 33A | 32 |
| 36 | 32 |
| 37 | 64 |
| 38 | 32 |
| 39A | 32 |
| 40 | 64 |
| 44 (one isomer) | 32 |
| 44 (another isomer) | 64 |
| 42 | 64 |
| 97 | 4 |
| 99 | 32 |
| 101 | 8 |
| 103 | 8 |
| 107 | 16 |
| 109 | 64 |
| 111 | 8 |
| 113 | 8 |

REFERENCES

1. S. C. Stinson, *Chem. & Eng. News*, 1996, 75.
2. S. J. Brickner, *Chemistry & Industry*, 1997, 131.
3. T Kaneko, R G Linde II, W.-G. Su, Ann. Rep. Med. Chem., 1999, 34, 169
4. P. Groves, M. S. Searle, I. Chicarelli-Robertson, D. H. Williams, *J. Chem. Soc. Perkin I*, 1994, 659.
5. R. J. Dancer, A. C. Try, G. J. Sharman, D. H. Williams, *J. Chem. Soc. Chem. Commun.*, 1996, 1445.
6. D. H. Williams, B Bardsley, Angew. Chem. $2^{nd}$ Ed., 1999, 38, 1173.
7. K. Nakamura et al., *Tetrahedron Lett.*, 1995, 36, 8625 and 8629.
8. M. Ezaki et al., *J. Antibiot.*, 1985, 38, 1453.
9. P. H. Popieniek, P. R. Pratt, *Anal. Biochem.* 1987, 165, 108.
10. D. S. Lingerfelter, R. C. Helgeson, D. J. Cram, J. Org. Chem., 1981, 46, 393

What is claimed is:
1. A compound of the formula (I):

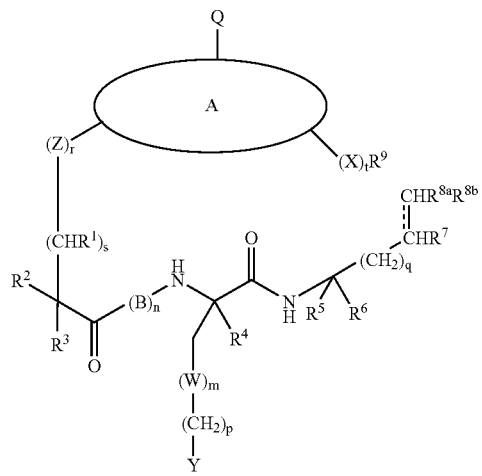

wherein
A is a 2,2'-dimethoxy-1,1'-binapthyl group or a 1,1'-binapthyl group;
X and Z are at the 3 and 3' positions of the binapthyl group, respectively or at the 2 and 2' positions of the binapthyl group respectively;
Q is hydrogen, $C_1$–$C_{12}$ straight chain, branched or cyclic alkyl substituted with one or more hydroxy groups, or a mono- or di-saccharide moiety;
Z is —$CR^{10}R^{11}$—, —$NR^{12}$—, —C(O)O—, —C(O)$NR^{12}$— or —O—, where $R^{10}$ and $R^{11}$ are independently selected from hydrogen, hydroxy, $C_1$–$C_6$ alkyl, $C_6$–$C_{10}$ aryl, $C_1$–$C_6$ alkoxy and —$N(R^{13})_2$ and where each $R^{13}$ is independently selected from hydrogen and $C_1$–$C_6$ alkyl, and where $R^{12}$ is selected from hydrogen and $C_1$–$C_6$ alkyl;
$R^1$ is selected from hydrogen, hydroxy, $C_1$–$C_6$ alkyl, $C_1$–$C_6$ alkoxy, —$N(R^{13})_2$ and —$N(R^{12})$—$COR^{14}$; where $R^{12}$ and $R^{13}$ are as defined above, and where $R^{14}$ is selected from hydrogen, hydroxy, $C_1$–$C_6$ alkyl, $C_1$–$C_6$ alkoxy and —$NR^{12}$;
$R^2$ is selected from hydrogen, hydroxy, $C_1$–$C_6$ alkyl, $C_1$–$C_6$ alkoxy, —$N(R^{13})_2$ and —$N(R^{12})$—$COCHR^{2a}R^{2b}$; where $R^{2a}$ and $R^{2b}$ are selected from hydrogen, hydroxy, $C_1$–$C_6$ alkyl, $C_1$–$C_6$ alkoxy, —$N(R^{13})_2$ and —$N(R^{12})$—$COR^{14}$; where $R^{12}$, $R^{13}$ and $R^{14}$ are as defined above;
$R^3$, $R^4$ and $R^5$ are independently selected from hydrogen, $C_1$–$C_6$ alkyl and α side chains of α-amino acids;

$R^6$ is —$CO_2R^{15}$, —$CONHR^{16}$, —$CONHOR^{16}$, —$CONHNHR^{16}$, —$SO_2N(R^{16})_2$, —$SO_2R^{17}$ or —$P(O)(OR^{18})(OR^{18})$ where each $R^{15}$, $R^{16}$, $R^{17}$ and $R^{18}$ is independently selected from hydrogen, $C_1$–$C_6$ alkyl, $C_3$–$C_7$ cycloalkyl, $C_6$–$C_{10}$ aryl and $C_7$–$C_{10}$ arylalkyl;

B is an α-amino acid residue, a β-amino acid residue or an α,α-disubstituted amino acid residue, such residue forming amide linkages with the adjacent molecules;

W is —O— or $CR^{10}R^{11}$ where $R^{10}$ and $R^{11}$ are as defined above;

Y is an optionally substituted amino group, a moiety containing an optionally substituted amino group or a salt thereof;

----- is a single or double bond;

$R^7$ and $R^{8a}$ are hydrogen or are absent if

----- is a double bond; and $R^{8b}$ and $R^9$ are hydrogen, and X is selected from $(CR^{10}R^{11})_u$, —$(CR^{10}R^{11})_u$—CH=CH—, —$NR^{12}(CR^{10}R^{11})_u$—, —$(CR^{10}R^{11})_uNR^{12}$, —$O(CR^{10}R^{11})_u$—, —$(CR^{10}R^{11})_uO$— or —$O(CR^{10}R^{11})$CH=CH— where $R^{10}$, $R^{11}$ and $R^{12}$ are as defined above; or $R^{8b}$ and $R^9$ together form a covalent bond between X and the carbon to which $R^{8b}$ is attached, and X is selected from $(CR^{10}R^{11})_x$, —$NR^{12}(CR^{10}R^{11})_x$—, —$(CR^{10}R^{11})_xNR^{12}$—, —$O(CR^{10}R^{11})_x$— or —$(CR^{10}R^{11})_xO$—, where $R^{10}$, $R^{11}$ and $R^{12}$ are as defined above;

n, m, r and t are independently selected from 0 or 1;

s is an integer selected from 0 to 3;

p is an integer selected from 0 to 6, provided that when W is —O—, p is at least 1; and u, x and q are independently selected from 0 to 4;

or a pharmaceutically acceptable salt thereof.

2. A compound of claim 1 wherein each $R^1$ is H; and $R^2$ is —NH—COCHR$^{2a}$R$^{2b}$.

3. A compound according to claim 1 wherein Q is hydrogen.

4. A compound according to claim 1 wherein Z is —$CH_2$— or —O—.

5. A compound according to claim 1 wherein s is 0, 1 or 2 and each $R^1$ is independently selected from hydrogen or hydroxy.

6. A compound according to claim 1 wherein $R^2$ is hydrogen, hydroxy or $N(R^{12})COR^{2a}R^{2b}$.

7. A compound according to claim 1 wherein $R^3$ is hydrogen.

8. A compound according to claim 1 wherein B is absent or a D- or L-alanyl residue, a D-lysinyl residue, a D-arginyl residue or a D-homoarginyl residue.

9. A compound according to claim 1 wherein Y is selected from a group consisting of: —$N(R^{13})_2$, —$N(R^{12})$—$COR^{14}$, —$NR^{13}C(=NR^{13})N(R^{13})_2$, —$C(=NR^{13})N(R^{13})_2$, —$NR^{13}C(=O)N(R^{13})_2$, —$N=NC(=NR^{13})N(R^{13})_2$, $NR^{13}NR^{13}C(=O)NHN(R^{13})_2$, —$NR^{13}C(=)NHN(R^{13})_2$, wherein $R^{12}$ and each $R^{13}$ is independently selected from hydrogen and $C_1$–$C_6$ alkyl and $R^{14}$ is selected from hydrogen, hydroxy, $C_1$–$C_6$ alkyl, $C_1$–$C_6$ alkoxy and $NR^{12}$; and a 3–8-membered N-containing cyclogroup.

10. A compound according to claim 9 wherein Y is an unsubstituted amino group or a guanidino group, or their hydrochloride salts.

11. A compound according to claim 1 wherein $R^6$ is $CO_2R^{15}$ where $R^{15}$ is $C_1$–$C_6$ alkyl or $C_7$–$C_{10}$ arylalkyl.

12. A compound according to claim 11 wherein $R^{15}$ is methyl or benzyl.

13. A compound according to claim 1 wherein $R^{8b}$ and $R^9$ are hydrogen and X is —$(CR^{10}R^{11})_u$—, —$O(CH2)_u$-, —CH=CH—, —$O(CR^{10}R^{11})$CH=CH— or —$CR^{10}R^{11}$—CH=CH— where $R^{10}$ and $R^{11}$ are hydrogen and u is an integer selected from 2 or 3.

14. A compound according to claim 1 wherein $R^{8b}$ and $R^9$ together form a covalent bond between X and the carbon to which $R^{8b}$ is attached and X is —$(CR^{10}R^{11})_x$— or —$O(CH2)_x$- wherein $R^{10}$ and $R^{11}$ are hydrogen and x is an integer from 1 to 4.

15. A compound according to claim 1 selected from benzyl (aR/S,2S,5R)-8-acetamido-2-allyl-9-{3-[3'-allyl-2,2'-dimethoxy-1,1'-binaphthyl]}-3,6-diaza-5-(4-{[(tert-butoxy)carbonyl]amino}butyl)-4,7-dioxononanoate;

(aR/S,7R,10S)-4-acetamido-7-(4-aminobutyl)-6,9-diaza-10-methoxycarbonyl-1(1,3),2(1,3)-di(2-methoxynaphthalena)-5,8-dioxocyclotetradecaphane-12-ene hydrochloride;

(aR/S,7R,10S)-4-acetamido-7-(4-aminobutyl)-6,9-diaza-10-methoxycarbonyl-1(1,3),2(1,3)-di(2-methoxynaphthalena)-5,8-dioxocyclotetradecaphane hydrochloride;

(aR/S,7R,10S)-4-acetamido-6,9-diaza-10-benzyloxycarbonyl-7-(4-{[(tert-butoxy)carbonyl]amino}butyl)-1(1,3),2(1,3)-di(2-methoxynaphthalena)-5,8-dioxocyclotetradecaphane-12-ene;

methyl (aR/S,2S,5R)-8-acetamido-2-allyl-9-[3-(3'-allyl-2,2'-dimethoxy-1,1'-binaphthyl)]-3,6-diaza-5-(3-guanidinopropyl)-4,7-dioxononanoate hydrochloride;

(aR/S,7S,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane-12-ene hydrochloride;

(aR/S,7R,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane-12-ene hydrochloride;

(aR/S,7R,10S)-4-acetamido-6,9-diaza-7-(3-guanidinopropyl)-10-methoxycarbonyl-1(1,3),2(1,3)-di(2-methoxynaphthalena)-5,8-dioxocyclotetradecaphane hydrochloride;

methyl (aR/S,2S,5R)-2-allyl-5-[2-({[(2'-allyloxy-1,1'-binaphthoxymethyl]carbonyl}amino)-3-aza-9-guanidino-4-oxononanoate hydrochloride;

(aR/S,7R,10S)-6,9-diaza-3,15-dioxa-5,8-dioxo-7-(4-guanidinobutyl)-10-methoxycarbonyl-1(1,2),2(1,2)-dinaphthalenacyclopentadecaphane-12-ene hydrochloride;

methyl (aS/R,2S,5R)-2-allyl-10-(2'-allyloxy-1,1'-binaphth-2-oxy)-5-(4-aminobutyl)-3,6-diaza-4,7-dioxodecanoate hydrochloride;

methyl (aS/R,2S,5R)-2-allyl-10-(2'-allyloxy-1,1'-binaphth-2-oxy)-3,6-diaza-5-(4-guanidinobutyl)-4,7-dioxodecanoate hydrochloride; or (aR/S,9R,12S)-8,11-diaza-9-(4-guanidinobutyl)-12-methoxycarbonyl-1(1,2),2(1,2)-dinaphthalena-3,17-dioxa-7,10-dioxoheptadecaphane-15-ene hydrochloride.

16. A composition comprising a compound of formula (I) according to claim 1, or a pharmaceutically acceptable salt thereof together with one or more pharmaceutically acceptable carriers or adjuvants.

17. A method of treating a bacterial infection in a mammal comprising administering an effective amount of a compound of formula (I) according to claim 1, or a pharmaceutically acceptable salt thereof.

18. A method according to claim 17 where the mammal is a human.

19. A method according to claim 17 wherein the bacterial infection is caused by Gram positive bacteria.

20. A method according to claim 19 wherein the bacterial infection is caused, by vancomycin resistant *Staphylococcus aureas*.

* * * * *